(12) United States Patent
Nishimae et al.

(10) Patent No.: US 11,505,561 B2
(45) Date of Patent: Nov. 22, 2022

(54) ORGANIC LIGHT EMITTING DEVICE AND MATERIALS FOR USE IN SAME

(71) Applicant: Idemitsu Kosan Co., Ltd., Chiyoda-ku (JP)

(72) Inventors: Yuichi Nishimae, Basel (CH); Natalia Chebotareva, Hagenthal le Bas (FR)

(73) Assignee: Idemitsu Kosan Co., Ltd., Chiyoda-ku (JP)

( * ) Notice: Subject to any disclaimer, the term of this patent is extended or adjusted under 35 U.S.C. 154(b) by 508 days.

(21) Appl. No.: 16/533,839

(22) Filed: Aug. 7, 2019

(65) Prior Publication Data

US 2020/0102329 A1 Apr. 2, 2020

(30) Foreign Application Priority Data

Aug. 7, 2018 (EP) ..................... 18187675

(51) Int. Cl.
- *H01L 51/00* (2006.01)
- *C07D 519/00* (2006.01)
- *H01L 51/50* (2006.01)

(52) U.S. Cl.
CPC ........ *C07D 519/00* (2013.01); *H01L 51/0067* (2013.01); *H01L 51/0072* (2013.01); *H01L 51/0073* (2013.01); *H01L 51/0074* (2013.01); *H01L 51/5048* (2013.01); *H01L 51/5096* (2013.01)

(58) Field of Classification Search
None
See application file for complete search history.

(56) References Cited

U.S. PATENT DOCUMENTS

| | | | |
|---|---|---|---|
| 2017/0077416 A1* | 3/2017 | Kim | H05B 33/20 |
| 2018/0370981 A1* | 12/2018 | Nishimae | C07D 495/06 |
| 2019/0173022 A1* | 6/2019 | Kim | C09K 11/06 |
| 2020/0066994 A1* | 2/2020 | Parham | C07D 495/06 |

FOREIGN PATENT DOCUMENTS

| | | |
|---|---|---|
| EP | 3 168 221 A1 | 5/2017 |
| KR | 10-2015-0111106 A | 10/2015 |
| KR | 10-2016-0039561 A | 4/2016 |
| KR | 10-2016-0056521 A | 5/2016 |
| KR | 10-2016-0143496 A | 12/2016 |
| WO | WO 2017/109727 A1 | 6/2017 |
| WO | WO 2018/104195 A1 | 6/2018 |

\* cited by examiner

*Primary Examiner* — Robert S Loewe
(74) *Attorney, Agent, or Firm* — Oblon, McClelland, Maier & Neustadt, L.L.P.

(57) ABSTRACT

Specifically substituted hetero- or carbon-bridged phenylquinazolines of the general formulae (Ia) and (Ib) and a process for their preparation, an electronic device comprising at least one of these compounds, an emitting layer, preferably present in an electronic device, comprising at least one compound of general formulae (Ia) and (Ib) and the use of compounds according to general formulae (Ia) and (Ib) in an electronic device as a host material, a charge transporting material, charge and/or exciton blocking material, preferably as a host material or an electron transporting material.

14 Claims, 1 Drawing Sheet

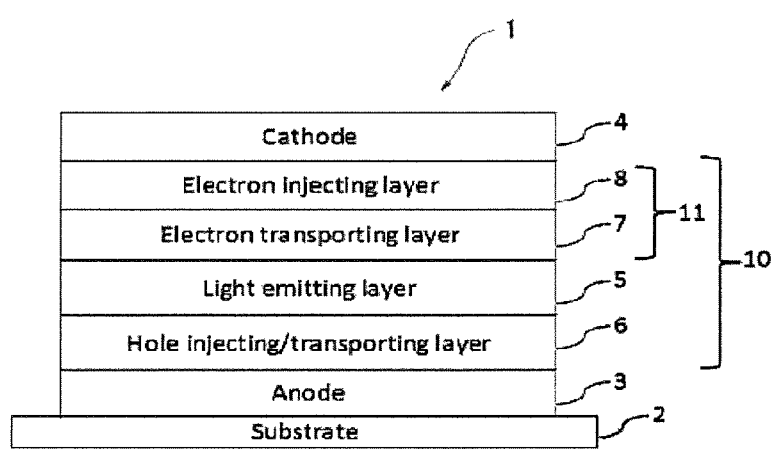

ORGANIC LIGHT EMITTING DEVICE AND MATERIALS FOR USE IN SAME

The present invention relates to specifically substituted hetero- or carbon-bridged phenyl-quinazolines of the general formulae (Ia) and (Ib) and to a process for their preparation, to an electronic device comprising at least one of these compounds, to an emitting layer, preferably present in an electronic device, comprising at least one compound of general formulae (Ia) and (Ib) and to the use of compounds according to general formulae (Ia) and (Ib) in an electronic device as a host material, a charge transporting material, charge and/or exciton blocking material, preferably as a host material or an electron transporting material.

Quinazolines and their use in electronic devices are generally known from the related art.

EP 3 168 221 A1 relates to compounds of formulae 1 and 2 and organic optoelectronic devices comprising the same:

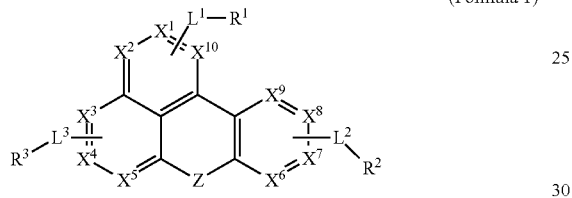

(Formula 1)

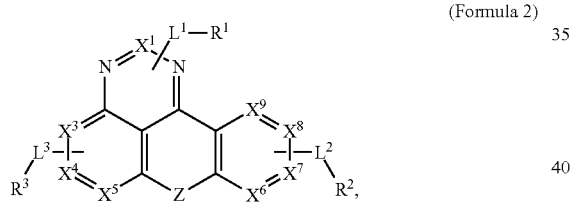

(Formula 2)

wherein -L$^1$-R$^1$ can represent a substituted carbazole-based pentacycle comprising two 5-membered N-heterocycles (Compound 101)

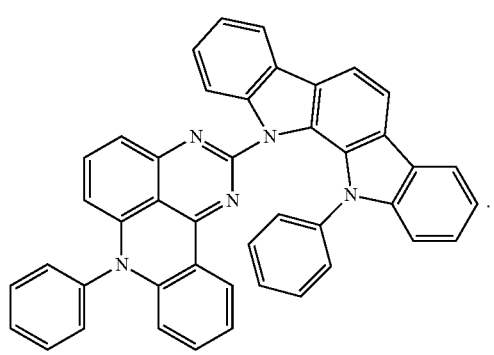

(Compound 101)

KR 20160056521 concerns compounds of formulae (1) and (2), and light emitting elements comprising said compounds as hosts.

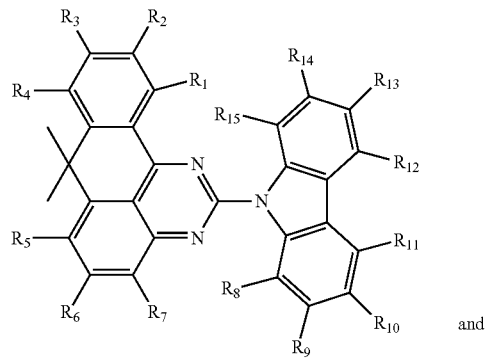

(1)

and (2)

The residues in said compounds may be fused, for example as shown below:

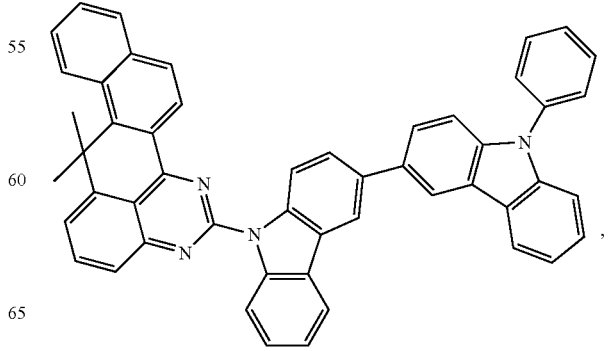

3

-continued

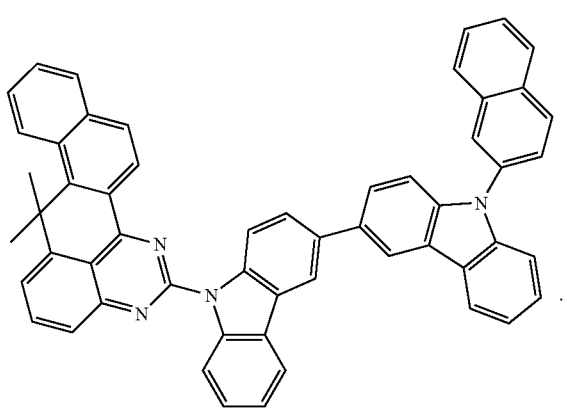

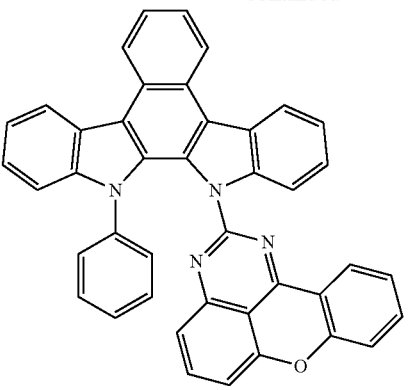

Compound 10

However, in KR 20160056521 no compounds comprising a carbazole-based pentacycle comprising two 5-membered N-heterocycles are disclosed.

WO 2017/109727 A1 relates to compounds of general formula (I)

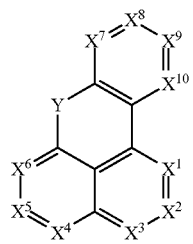

(I)

and their use in electronic devices, for example compounds of the following formulae:

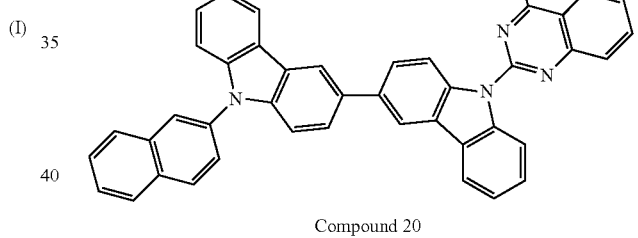

Compound 20

KR20160143496 relates to compounds of the general formula

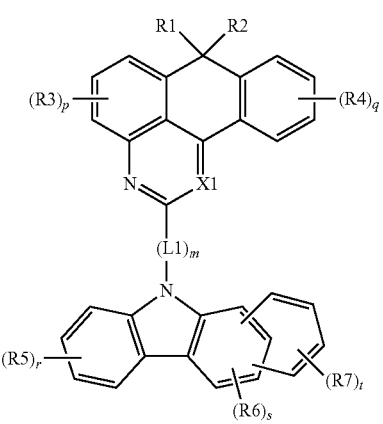

and their use in electronic devices. Exemplary mentioned compounds are for example

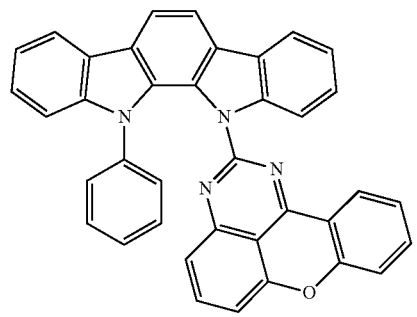

Compound 9

1-83

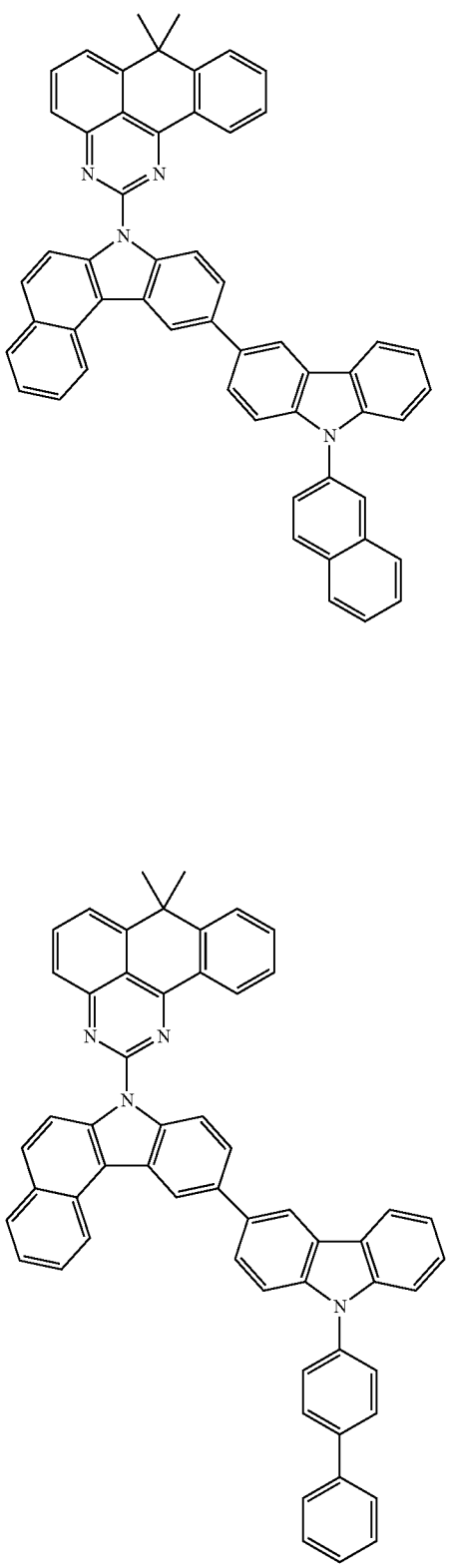

1-85 however, no compounds comprising a carbazole-based pentacycle comprising two 5-membered N-heterocycles are described.

KR 20150111106 A discloses compounds according to the following formulae

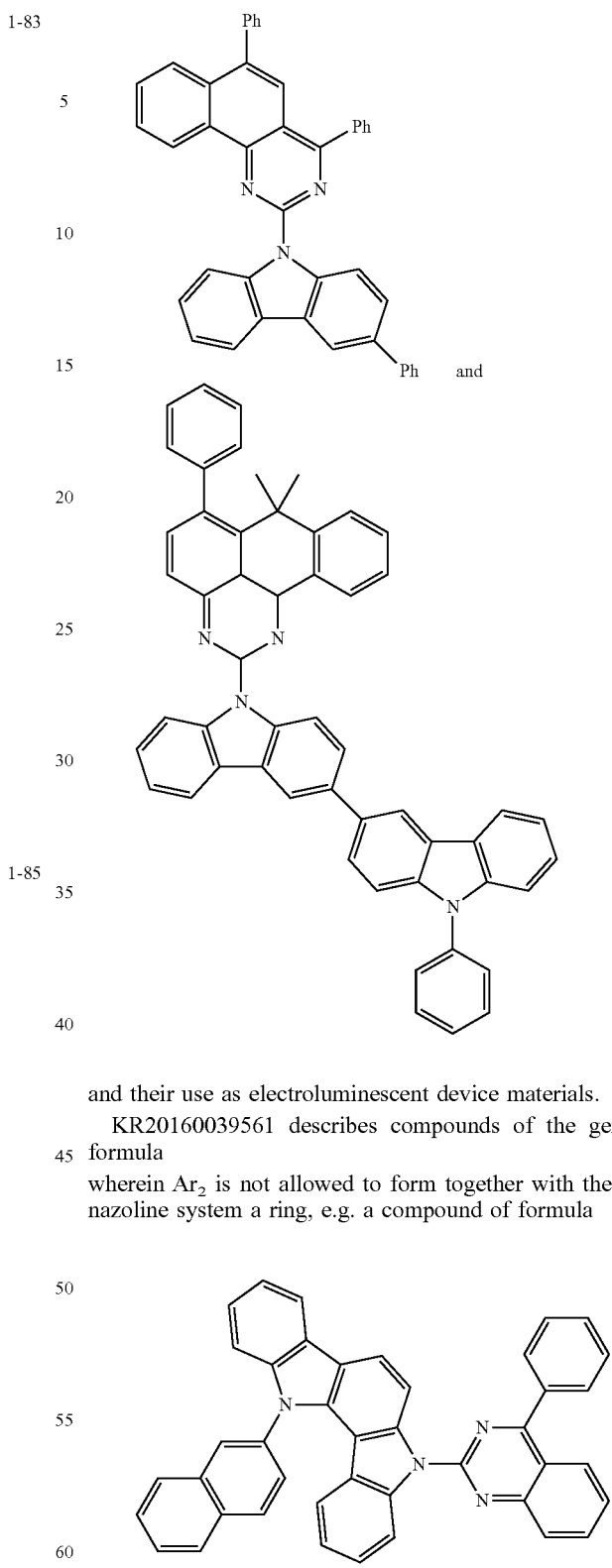

and their use as electroluminescent device materials.

KR20160039561 describes compounds of the general formula
wherein Ar$_2$ is not allowed to form together with the quinazoline system a ring, e.g. a compound of formula Those compounds are comprised in optoelectronic diodes.

WO 2018/104195 A1 relates to nitrogen-containing heterocycles of formula (I) which are substituted with carbazole groups, in particular for use in electronic devices, and to a method for producing the nitrogen-containing heterocycles, and to electronic devices comprising the same,

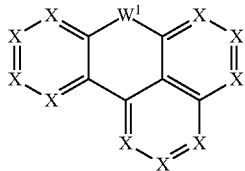

Formel (I)

wherein at least one group X is N, which is adjacent to one group, wherein X is C-(CAB), and CAB is a group of formula CAB-1:

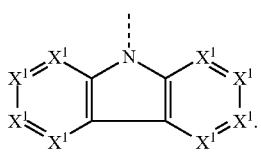

Formel (CAB-1)

It is an object of the present invention to provide electronic devices, preferably OLEDs, comprising new materials, especially as a host material, a charge transporting material, charge and/or exciton blocking material, preferably as a host material, having a good overall performance, especially improved efficiency and/or driving voltage and preferably having a high triplet energy.

This object is solved by a compound of general formula (Ia) or (Ib)

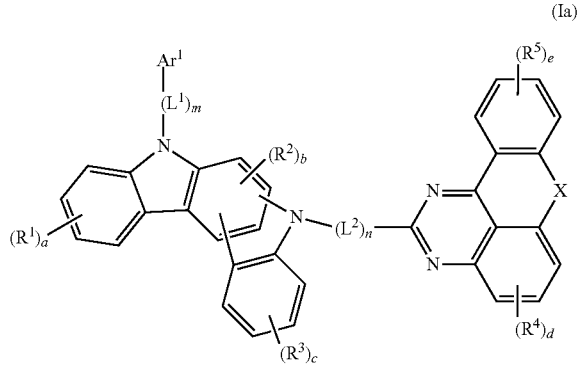

(Ia)

or

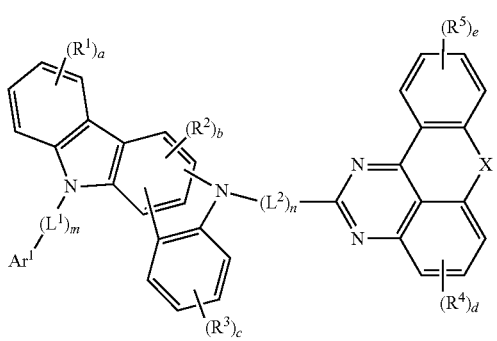

(Ib)

wherein
X is O, S, $NR^{10}$ or $CR^{11}R^{12}$;
$R^1$, $R^2$, $R^3$, $R^4$ and $R^5$ are independently of each other an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, —$OR^{21}$, —$SR^{21}$, —$NR^{17}R^{18}$, —CN, $SiR^{22}R^{23}R^{24}$ or halogen,
and/or
two of $R^1$, $R^2$, and $R^3$ if present at adjacent carbon atoms, together form at least one unsubstituted or substituted $C_6$-$C_{18}$aryl ring,
a, c, and e independently represent 0, 1, 2, 3 or 4;
b is 0, 1 or 2;
d is 0, 1, 2 or 3;
$R^{10}$, $R^{11}$ and $R^{12}$ are independently of each other H, an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group or an unsubstituted or substituted $C_5$-$C_{12}$cycloalkyl group;
m and n independently represent 1 or 2;
$L^1$ and $L^2$ are independently of each other a direct bond, an unsubstituted or substituted $C_6$-$C_{24}$arylene group or an unsubstituted or substituted $C_1$-$C_{24}$ heteroarylene group;
$Ar^1$ is an unsubstituted or substituted $C_{10}$-$C_{24}$aryl group, an unsubstituted or substituted $C_1$-$C_{24}$heteroaryl group;
$R^{17}$ and $R^{18}$ are independently of each other H, a $C_6$-$C_{18}$aryl group which is unsubstituted or substituted by at least one $C_1$-$C_{13}$alkyl group or at least one $C_1$-$C_{18}$alkoxy group, a $C_1$-$C_{18}$alkyl group or a $C_1$-$C_{18}$alkyl group, which is interrupted by at least one O, or
$R^{17}$ and $R^{18}$ together form a five or six membered aliphatic, aromatic or heteroaromatic ring;
$R^{21}$ is H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O;
$R^{22}$, $R^{23}$ and $R^{24}$ are independently of each other a $C_1$-$C_{18}$alkyl group, a $C_6$-$C_{18}$aryl group which is unsubstituted or substituted by at least one $C_1$-$C_{18}$alkyl group.

The compounds of formulae (Ia) and (Ib) are suitable as material for electronic devices, preferably OLEDs, especially as a host material, a charge transporting material, charge and/or exciton blocking material, preferably as a host material, having a good overall performance, especially improved efficiency and/or driving voltage and preferably having a high triplet energy, preferably of >2.0 eV.

The residues and indices mentioned in the specification of the present application generally have the following preferred meanings, if said residues and indices are not further specified in specific embodiments mentioned below:

Halogen is fluorine, chlorine, bromine or iodine.

$C_1$-$C_{25}$alkyl, preferably $C_1$-$C_8$alkyl, is typically linear or, where possible, branched alkyl. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec-butyl, isobutyl, tert-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl.

$C_1$-$C_4$alkyl is typically methyl, ethyl, n-propyl, isopropyl, n-butyl, sec-butyl, isobutyl, tert-butyl.

$C_1$-$C_{18}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec-butoxy, isobutoxy, tert-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec-butoxy, isobutoxy, tert-butoxy.

$C_6$-$C_{60}$aryl, preferably $C_6$-$C_{24}$aryl, particularly preferably $C_6$-$C_{18}$aryl, also particularly preferably $C_{10}$-$C_{24}$aryl, which optionally can be substituted, are typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted. Phenyl, 1-naphthyl and 2-naphthyl are examples of a $C_6$-$C_{10}$aryl group. Biphenylyl is an example for a $C_{12}$aryl group.

$C_1$-$C_{60}$heteroaryl, preferably $C_1$-$C_{30}$heteroaryl, preferably $C_1$-$C_{24}$heteroaryl, preferably $C_1$-$C_{18}$heteroaryl, more preferably $C_8$-$C_{18}$hereoaryl, and particularly preferably $C_8$-$C_{14}$heteroaryl, which optionally can be substituted, represents a ring with five to seven ring atoms or a condensed/fused ring system, wherein nitrogen, oxygen or sulfur are the possible hetero atoms, and is typically a heterocyclic group with preferably 5 to 40 atoms having at least six conjugated π-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazyl, pyrimidyl, pyrazinyl, pyridazinyl, indolizinyl, isoindolyl, indolyl, indazolyl, purinyl, quinolizinyl, quinolyl, isoquinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, benzimidazolo[2,1-b][1,3]benzothiazolyl, carbazolyl, or phenoxazinyl, which can be unsubstituted or substituted. Quinolinyl, Benzimidazo[1,2-a]benzimidazo-5-yl, benzimidazo[1,2-a]benzimidazo-2-yl, carbazolyl, dibenzofuranyl and dibenzothiophenyl are examples of a $C_2$-$C_{14}$heteroaryl group.

$C_7$-$C_{25}$aralkyl, which optionally can be substituted, is for example benzyl, 2-benzyl-2-propyl, β-phenyl-ethyl, α,α,-dimethylbenzyl, ω-phenyl-butyl, ω,ω-dimethyl-ω-phenylbutyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aro-aromatic hydrocarbon group may be unsubstituted or substituted. Preferred examples are benzyl, 2-phenylethyl, 3-phenylpropyl, naphthylethyl, naphthylmethyl, and cumyl.

$C_5$-$C_{12}$cycloalkyl, which optionally can be substituted, is for example cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

The $C_6$-$C_{24}$arylene group is a divalent aromatic hydrocarbon group having 6 to 24 ring carbon atoms may be a non-condensed divalent aromatic hydrocarbon group or a condensed divalent aromatic hydrocarbon group. Specific examples thereof include phenylene group, naphthylene group, phenanthrylene group, biphenyl-diyl group, terphenyl-diyl group, quaterphenyl-diyl group, fluoranthen-diyl group, triphenylenylene-diyl group, phenanthrene-diyl group, fluorene-diyl group, spirofluorene-diyl group, 9,9-diphenylfluorene-diyl group, 9,9'-spirobi[9H-fluorene]-2-diyl group, 9,9-dimethylfluorene-diyl group, benzo[c]phenanthrene-diyl group, benzo[a]triphenylene-diyl group, naphtho[1,2-c]phenanthrene-diyl group, naphtho[1,2-a]triphenylenylene-diyl group, dibenzo[a,c]triphenylenylene-diyl group, and benzo[b]fluoranthene-diyl group, with phenylene group, naphthylene group, biphenyl-diyl group, terphenyl-diyl group, phenanthryl-diyl group, triphenylenylen-diyl group, fluorene-diyl group, spirobifluorene-diyl group, and fluoranthene-diyl group being preferred, and 1,2-phenylene group, 1,3-phenylene group, 1,4-phenylene group, 1,4-naphthylene group, 1,8-naphthylene group, 2,6-naphthylene group, 2,7-naphthylene group, biphenyl-2,2'-diyl group, biphenyl-2,3'-diyl group, biphenyl-2,4'-diyl group, biphenyl-2,5'-diyl group, biphenyl-2,6'-diyl group, biphenyl-3,3'-diyl group, biphenyl-3,4'-diyl group, biphenyl-3,5'-diyl group, biphenyl-3,6'-diyl group, biphenyl-4,4'-diyl group, biphenyl-4,5'-diyl group, biphenyl-4,6'-diyl group, biphenyl-5,5'-diyl group, biphenyl-5,6'-diyl group, biphenyl-6,6'-diyl group, phenanthrene-9,10-diyl group, phenanthrene-2,3-diyl group, phenanthrene-2,7-diyl group, phenanthrene-2,8-diyl group, phenanthrene-2,6-diyl group, phenanthrene-2,9-diyl group, phenanthrene-2,10-diyl group, phenanthrene-3,9-diyl group, phenanthrene-3,10-diyl group, triphenylene-2,3-diyl group, triphenylene-2,5-diyl group, triphenylene-2,6-diyl group, triphenylene-2,7-diyl group, triphenylene-2,8-diyl group, 9,9-dimethylfluorene-2,7-diyl group, 9,9-dimethylfluorene-3,7-diyl group, 9,9-dimethylfluorene-1,4-diyl group, fluoranthene-3,9-diyl group, fluoranthene-3,8-diyl group, fluoranthene-3,4-diyl group, fluoranthene-3,5-diyl group, fluoranthene-3,6-diyl group, fluoranthene-2,9-diyl group, fluoranthene-2,8-diyl group, fluoranthene-2,4-diyl group, fluoranthene-2,5-diyl group, fluoranthene-2,6-diyl group, fluoranthene-1,9-diyl group, fluoranthene-1,8-diyl group, fluoranthene-1,4-diyl group, fluoranthene-1,5-diyl group, fluoranthene-1,6-diyl group being more preferred. The arylene group is substituted or unsubstituted.

The $C_1$-$C_{24}$heteroarylene group is a divalent heterocyclic group having 1 to 24 ring carbon atoms may be a non-condensed heterocyclic group or a condensed heterocyclic group. Specific examples thereof include the divalent residues of pyrrole ring, isoindole ring, benzofuran ring, isobenzofuran ring, dibenzothiophene ring, isoquinoline ring, quinoxaline ring, phenanthridine ring, phenanthroline ring, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadia-oxadiazole ring, benzoxazole ring, thiazole ring, thiadiazole ring, benzothiazole ring, triazole ring, imidazole ring, benzimidazole ring, pyran ring, dibenzofuran ring, and benzo[c]dibenzofuran ring, and the divalent residues of derivatives of these rings, with the divalent residues of dibenzofuran ring, carbazole ring, dibenzothiophene ring, and derivatives of these divalent rings being preferred, and the dibenzofuran-diyl group, 9-phenylcarbazole-diyl group and dibenzothiophene-diyl group being more preferred. The heteroarylene group is substituted or unsubstituted.

The five or six membered aliphatic, aromatic or heteroaromatic ring is a $C_5$-$C_6$cycloalkyl ring, which optionally can be substituted, i.e. cyclopentyl, or cyclohexyl, which may be unsubstituted or substituted; a $C_6$aryl, which optionally can be substituted, i.e. phenyl which may be unsubstituted or substituted or a $C_3$-$C_6$heteroaryl, which optionally can be substituted, wherein nitrogen, oxygen or sulfur are the possible hetero atoms, e.g. furanyl, pyrrolyl, thiophenyl, imidazolyl, pyrazolyl, oxazolyl, isoxazolyl, thiazolyl, pyridinyl, pyrazinyl, pyrimidinyl, triazinyl or pyridazinyl, which may be unsubstituted or substituted.

The abovementioned groups are substituted or unsubstituted. Possible preferred optional substituents of the abovementioned groups are $C_1$-$C_{18}$alkyl, a hydroxyl group, a mercapto group, $C_1$-$C_{18}$alkoxy, $C_1$-$C_8$alkylthio, halogen, halo-$C_1$-$C_8$alkyl, $C_6$-$C_{24}$aryl, $C_2$-$C_{30}$heteroaryl, or a cyano group, preferably $C_1$-$C_{18}$alkyl or $C_1$-$C_{18}$alkoxy.

The optional substituents mentioned above may be further substituted by one or more of the optional substituents mentioned above.

The number of the optional substituents depends on the group which is substituted by said substituent(s). Preferred are 1, 2, 3 or 4 optional substituents, more preferred are 1, 2 or 3 optional substituents, most preferred are 1 or 2 optional substituents. In a further preferred embodiment, the groups mentioned above are unsubstituted.

The "carbon number of a to b" in the expression of "X group having a to b carbon atoms" is the carbon number of the unsubstituted X group and does not include the carbon atom(s) of an optional substituent.

The hydrogen atom referred to herein includes isotopes different from neutron numbers, i.e., light hydrogen (protium), heavy hydrogen (deuterium) and tritium. Therefore, one or more or all of the hydrogen atoms in the residues mentioned above and below may be replaced by protium, deuterium or tritium, preferably by deuterium.

The compounds of formula (Ia) or (Ib)

The present invention relates to compounds of the general formula (Ia) or (Ib)

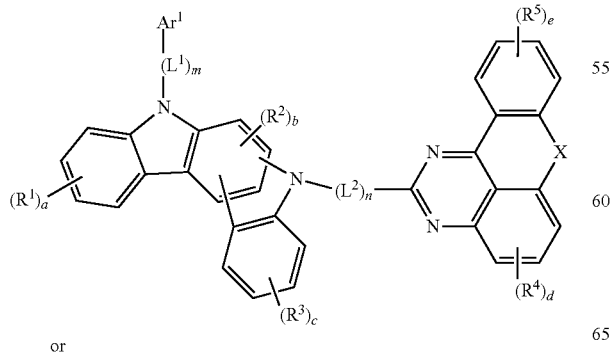

(Ia)

or

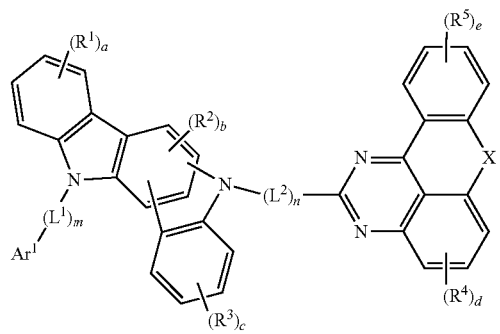

(Ib)

wherein X, $R^1$, $R^2$, $R^3$, $R^4$, $R^5$, a, b, c, d, e, m, n, $L^1$, $L^2$ and $Ar^1$ have the meanings as mentioned above.

The compounds of the above formulae (Ia) and (Ib) therefore comprise a quinazolinyl moiety of formula (Iab*)

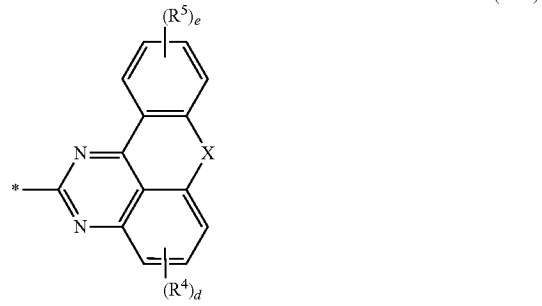

(Iab*)

and an at least pentacyclic moiety of formula (Ia*) or (Ib*)

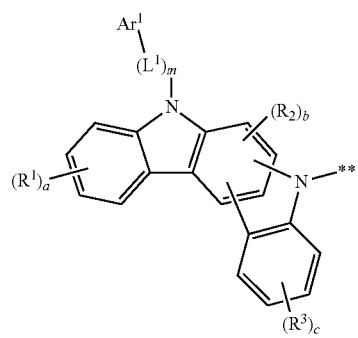

(Ia*)

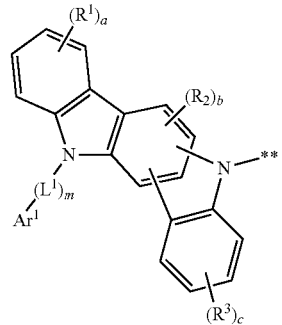

(Ib*)

which are connected with each other via a group **-(L²)ₙ-*
at the * and **-locations.

In more detail, formula (Ia*) represents moieties of one of the following formulae:

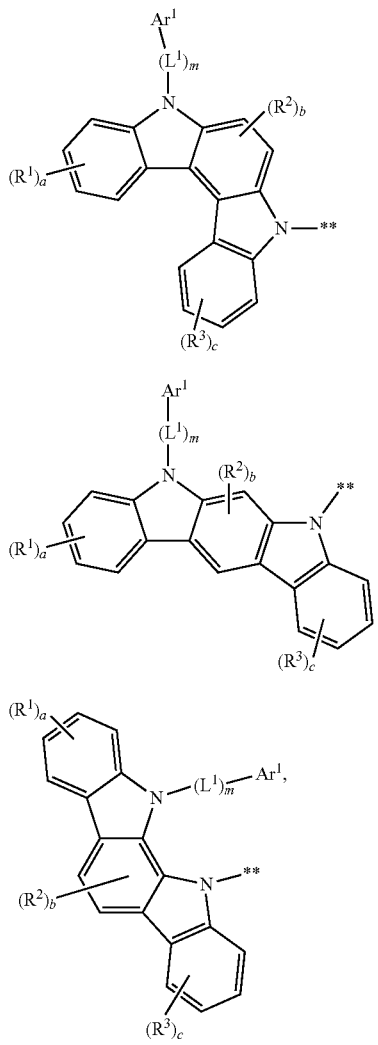

preferably a moiety of formulae (Ia*-2) and (Ia*-3).

Formula (Ib*) represents moieties of the following formulae

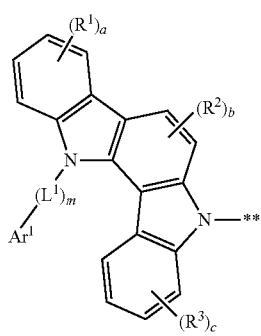

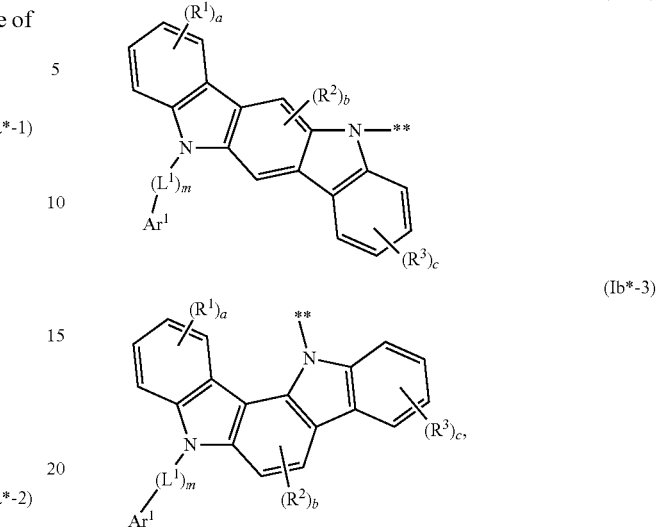

preferably moieties of formula (Ib*-1) or (Ib*-3).

Preferred embodiments for the compounds of formulae (Ia) and (Ib) are explained in the following.

X in the general formula (Ia) or (Ib) is O, S, $NR^{10}$ or $CR^{11}R^{12}$, preferably O, S or $NR^{10}$, more preferably O or S, particularly preferably O.

In the general formula (Ia) or (Ib) $R^1$, $R^2$, $R^3$, $R^4$ and $R^5$ are independently of each other an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group, an unsubstituted or substituted $C_5$-$C_{12}$cycloalkyl group, $-OR^{21}$, $-SR^{21}$, $-NR^{17}R^{18}$, $-CN$, $SiR^{22}R^{23}R^{24}$ or halogen,
and/or
two of $R^1$, $R^2$, and $R^3$ if present at adjacent carbon atoms, together form at least one unsubstituted or substituted $C_6$-$C_{18}$aryl ring.

In a preferred embodiment of the invention $R^1$, $R^2$, $R^3$, $R^4$ and $R^5$ are independently of each other an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, $-OR^{21}$, $-SR^{21}$, $-NR^{17}R^{18}$, $-CN$, $SiR^{22}R^{23}R^{24}$ or halogen,
and/or
two of $R^1$, $R^2$, and $R^3$ if present at adjacent carbon atoms, together form at least one unsubstituted or substituted $C_6$-$C_{18}$aryl ring.

In a more preferred embodiment of the invention $R^1$, $R^2$, $R^3$, $R^4$ and $R^5$ are independently of each other selected from a $C_6$-$C_{24}$aryl group which is unsubstituted, a $C_1$-$C_{30}$ heteroaryl group which is unsubstituted, or a $C_1$-$C_{25}$alkyl group, which is unsubstituted,
and/or
two of $R^1$, $R^2$ and $R^3$, if present at adjacent carbon atoms, together form at least one $C_6$-$C_{18}$aryl ring which is unsubstituted.

Even more preferred $R^1$, $R^2$ and $R^3$ are independently of each other selected from $C_6$-$C_{10}$aryl group which is unsubstituted, $C_1$-$C_8$ heteroaryl group which is unsubstituted, or a $C_1$-$C_6$alkyl group, which is unsubstituted,
and/or two of $R^1$, $R^2$ and $R^3$, preferably two of $R^2$, if present at adjacent carbon atoms, together form at least one $C_6$-$C_{10}$aryl ring which is unsubstituted, preferably a phenyl ring which is unsubstituted.

Preferably, at least one of $R^4$ and $R^5$ is selected from a $C_6$-$C_{24}$aryl group which is unsubstituted, or a $C_1$-$C_{30}$heteroaryl group, which is unsubstituted, preferably a $C_6$-$C_{10}$aryl group which is unsubstituted or a $C_8$-$C_{12}$-heteroaryl group which is unsubstituted, particularly preferably phenyl which is unsubstituted or dibenzofuranyl which is unsubstituted.

In the general formulae (Ia) and (Ib) a, c, and e independently represent 0, 1, 2, 3 or 4, preferably 0, 1 or 2, more preferably 0 or 1 and particularly preferably 0.

In the above formulae b is 0, 1 or 2, preferably 0 or 2 and d is 0, 1, 2, or 3, preferably 0, 1, or 2 and more preferably 0 or 1.

In one preferred embodiment of the invention, a, b, c, d, and e are 0.

In another preferred embodiment a, b, c, and e are 0 and d is 1.

In another preferred embodiment a, c and e are 0, b is 0 or 2 and d is 1.

In another preferred embodiment a, c, d and e are 0 and b is 2, wherein it is particularly preferred that the two of $R^2$ are present at adjacent carbon atoms, and together form at least one $C_6$-$C_{10}$aryl ring which is unsubstituted, preferably a phenyl ring which is unsubstituted.

In the general formulae (Ia) and (Ib) $R^{10}$, $R^{11}$ and $R^{12}$ are independently of each other H, an unsubstituted or substituted $C_6$-$C_{24}$aryl group, an unsubstituted or substituted $C_1$-$C_{30}$heteroaryl group, an unsubstituted or substituted $C_1$-$C_{25}$alkyl group, an unsubstituted or substituted $C_7$-$C_{25}$aralkyl group or an unsubstituted or substituted $C_5$-$C_{12}$cycloalkyl group.

In a preferred embodiment of the invention $R^{10}$ is an unsubstituted or substituted $C_6$-$C_{18}$aryl group, an unsubstituted or substituted $C_1$-$C_{24}$heteroaryl group or an unsubstituted or substituted $C_1$-$C_{25}$alkyl group, more preferably a $C_6$-$C_{10}$aryl group which is unsubstituted, a $C_8$-$C_{12}$heteroaryl group which is unsubstituted or a $C_1$-$C_6$alkyl group, which is unsubstituted. Particularly preferably, $R^{10}$ is phenyl.

Preferably, $R^{11}$ and $R^{12}$ are independently of each other a $C_1$-$C_{25}$alkyl group, which is unsubstituted or substituted by at least one group E, preferably a $C_1$-$C_8$ alkyl group, which is unsubstituted or substituted by at least one group E, preferably $C_1$-$C_{12}$alkyl group, which is unsubstituted, more preferably $C_1$-$C_4$alkyl group which is unsubstituted, and particularly preferably methyl.

m and n independently represent 1 or 2; preferably 1.

$L^1$ and $L^2$ are independently of each other a direct bond, an unsubstituted or substituted $C_6$-$C_{24}$arylene group, or an unsubstituted or substituted $C_1$-$C_{24}$heteroarylene group; preferably $L^1$ and $L^2$ are independently of each other a direct bond or an unsubstituted or substituted $C_6$-$C_{24}$arylene group, more preferably a direct bond or a phenylene group which is unsubstituted and particularly preferably a direct bond.

$Ar^1$ is an unsubstituted or substituted $C_{10}$-$C_{24}$aryl group, or an unsubstituted or substituted $C_1$-$C_{24}$heteroaryl group, preferably an unsubstituted or substituted $C_{10}$-$C_{14}$aryl group or an unsubstituted or substituted $C_8$-$C_{14}$heteroaryl group, more preferably an unsubstituted or substituted $C_{10}$-$C_{14}$aryl group or an unsubstituted or substituted $C_8$-$C_{14}$heteroaryl group and particularly preferably a $C_{10}$-$C_{14}$aryl group which is unsubstituted or a $C_8$-$C_{14}$heteroaryl group which is unsubstituted.

$R^{17}$ and $R^{18}$ are independently of each other H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O, or $R^{17}$ and $R^{18}$ together form a five or six membered aliphatic, aromatic or heteroaromatic ring.

$R^{21}$ is H, a $C_6$-$C_{18}$aryl group which is unsubstituted or substituted by at least one $C_1$-$C_{18}$alkyl group or at least one $C_1$-$C_{18}$alkoxy group, a $C_1$-$C_{18}$alkyl group or a $C_1$-$C_{18}$alkyl group, which is interrupted by at least one O, $R^{22}$, $R^{23}$ and $R^{24}$ are independently of each other a $C_1$-$C_{18}$alkyl group, a $C_6$-$C_{18}$aryl group which is unsubstituted or substituted by at least one $C_1$-$C_{18}$alkyl group.

Preferably, the present invention relates to compounds of formula (Ia) or (Ib) represented by one of the following formulae (II-1), (II-2), (II-3) or (II-4)

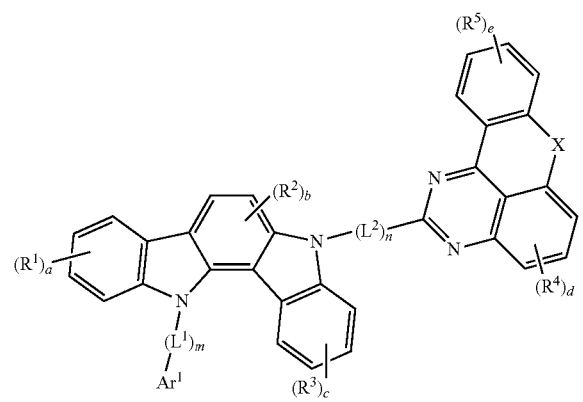

(II-1)

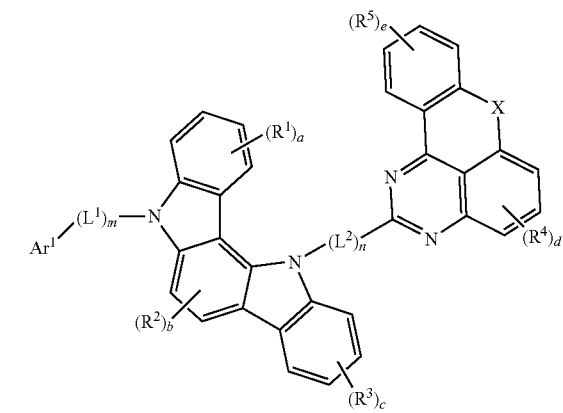

(II-2)

-continued (II-3)
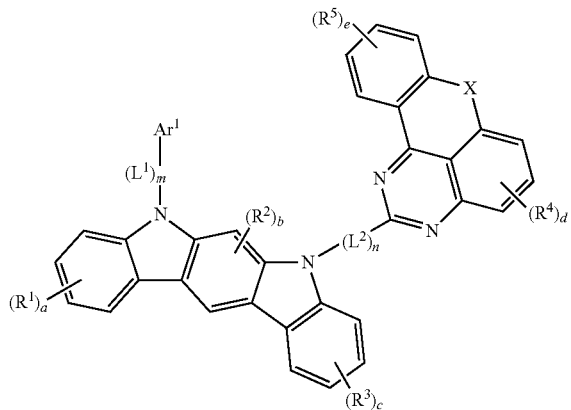

(II-4)
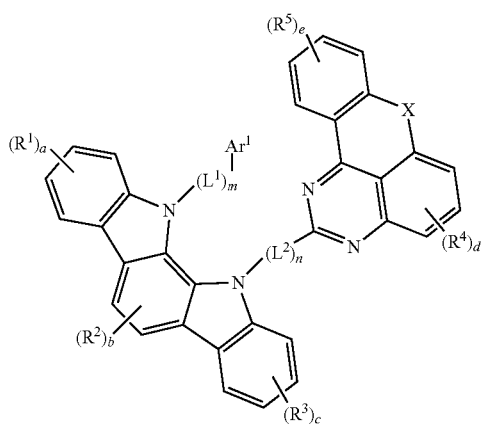

wherein X, $R^1$, $R^2$, $R^3$, $R^4$, $R^5$, a, b, c, d, e, m, n, $L^1$, $L^2$ and $Ar^1$ have the meanings as mentioned above.

In a preferred embodiment of the compounds of formulae (Ia) and (Ib), and the preferred compounds of formulae (II-1)-(II-4) $L^2$ represents a direct bond and n represents 1.

Therefore, the present invention preferably relates to compounds of formulae (Ia) and (Ib) represented by one of the following formulae (III-1), (III-2), (III-3), (III-4)

(III-1)
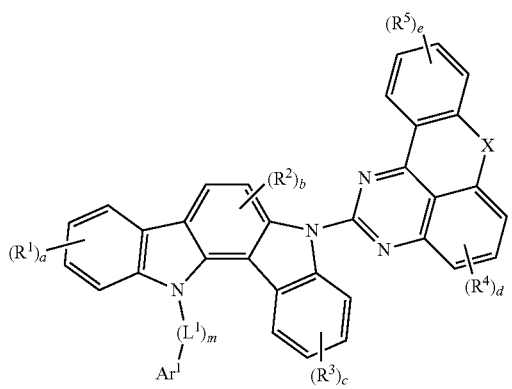

-continued (III-2)
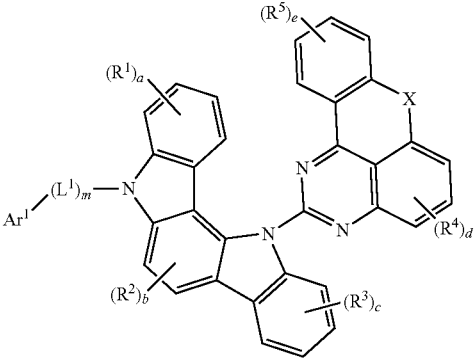

(III-3)
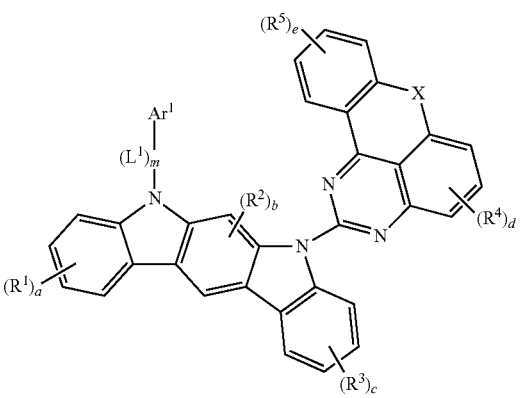

(III-4)
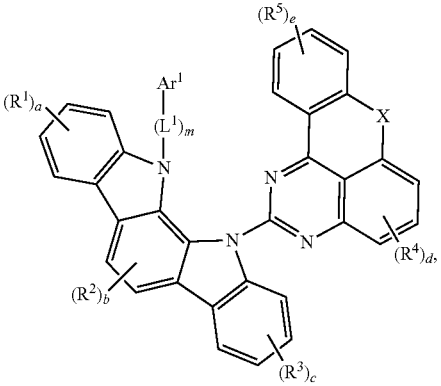

wherein $R^1$, $R^2$, $R^3$, $R^4$, $R^5$, $L^1$, $L^2$, X, $Ar^1$, a, b, c, d, e and m have the same meaning as defined above.

In a particularly preferred embodiment of the compounds (Ia) and (Ib) of the invention, preferably in compounds of formulae (II-1) to (II-4), and particularly preferably of the compounds of formulae (III-1) to (III-4) $L^1$ represents a direct bond and m represents 1.

In a preferred embodiment of the compounds (Ia) and (Ib) of the invention, preferably in compounds of formulae (II-1) to (II-4), and particularly preferably of the compounds of formulae (III-1) to (III-4) $Ar^1$ is an unsubstituted or substituted $C_{10}$-$C_{24}$aryl group or an unsubstituted or substituted $C_8$-$C_{14}$heteroaryl group.

Preferred $C_{10}$-$C_{24}$aryl groups are naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

Preferred $C_8$-$C_{14}$heteroaryl groups are dibenzofuranyl, dibenzothiophenyl, quinolinyl, quinazolinyl and isoquinolinyl, which may be unsubstituted or substituted.

More preferably, $Ar^1$ is selected from the group consisting of naphthyl, biphenylyl, dibenzofuranyl, dibenzothiophenyl and quinolinyl, which is in each case unsubstituted or substituted, preferably unsubstituted.

In a particularly preferred embodiment of the invention $Ar^1$ in the above formulae is represented by one of formulae (XXa*), (XXb*), (XXc*), (XXd*), (XXe*) or (XXf*)

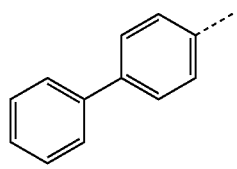
(XXa*)

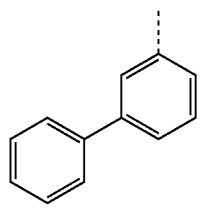
(XXb*)

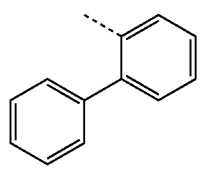
(XXc*)

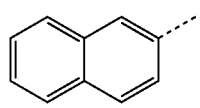
(XXd*)

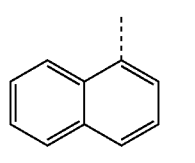
(XXe*)

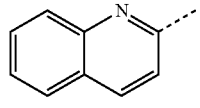
(XXf*)

wherein $Ar^1$ is bonded to the moiety represented by the general formula (Ia) or (Ib) via the*-location.

In a particularly preferred embodiment of the invention $Ar^1$ is represented by naphthyl, which is unsubstituted or biphenylyl, which is unsubstituted, particularly preferred $Ar^1$ is represented by formula (XXa*), (XXd*) or (XXf*).

As described above a, c, and e independently represent 0, 1, 2, 3, or 4, b represents 0, 1 or 2 and d represents 0, 1, 2, or 3. The number given for a, b, c, d and e represents the number of substituents $R^1$, $R^2$, $R^3$, $R^4$ or $R^5$ located on the particular $C_6$-aromatic rings different from H.

In a preferred embodiment of the compounds of the invention at least one of a, b, c, d and e is 0, more preferred at least two of a, b, c, d and e are 0, more preferably at least three of a, b, c, d and e are 0, more preferably at least four of a, b, c, d and e are 0.

In a preferred embodiment a, c and e represent 0.

In one particularly preferred embodiment a, c, d and e are 0 and b represents 2. In this case, it is particularly preferred that the compounds of formulae (Ia) and (Ib) are represented by one of the general formulae (II-1), (II-2) or (II-4), wherein the two of $R^2$ are present at adjacent carbon atoms, and together form at least one $C_6$-$C_{10}$aryl ring, preferably a phenyl ring.

In another particularly preferred embodiment are a, b, c, d and e are 0.

Thus, in a preferred embodiment of the invention the compounds of formula (Ia) or (Ib), preferably in compounds of formulae (II-1) to (II-4), and particularly preferably of the compounds of formulae (III-1) to (III-4) are represented by one of the following formulae (IV-1), (IV-2), (IV-3), (IV-4) or (IV-5)

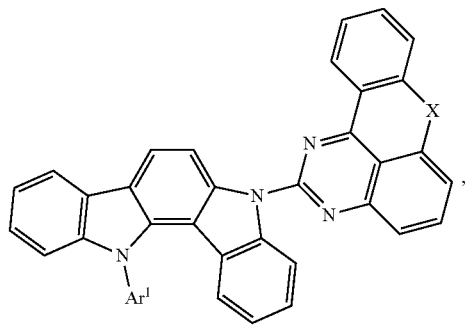
(IV-1)

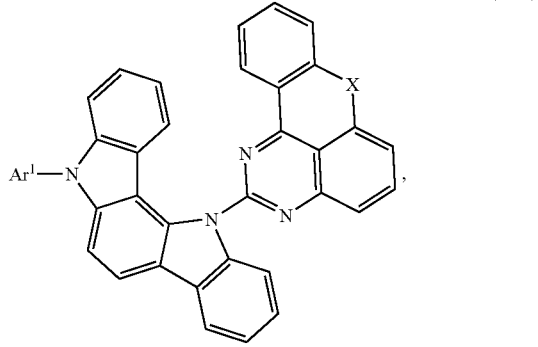
(IV-2)

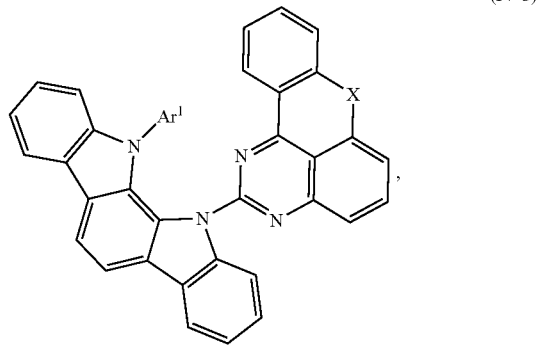
(IV-3)

-continued (IV-4)

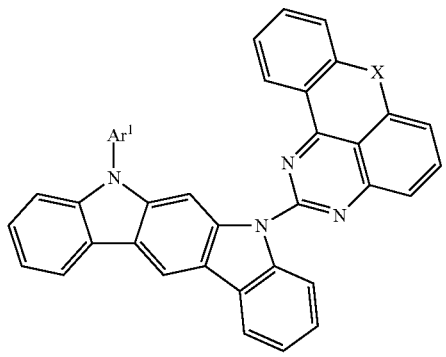

(IV-5)

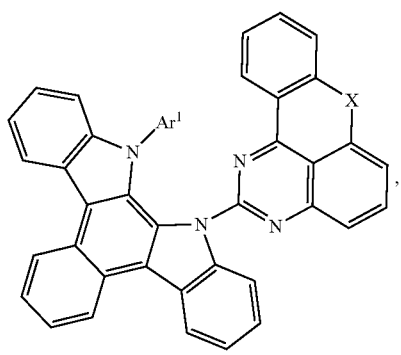

wherein X and Ar¹ have the same meaning as defined above.

As described above, X in the general formula (Ia) or (Ib) is O, S, NR¹⁰ or CR¹¹R¹². It is preferred that X is O, S, NR¹⁰ or CR¹¹R¹², wherein R¹⁰ is an unsubstituted or substituted $C_6$-$C_{18}$aryl group, an unsubstituted or substituted $C_1$-$C_{24}$heteroaryl group or an unsubstituted or substituted $C_1$-$C_{25}$alkyl group, more preferably a $C_6$-$C_{10}$aryl group which is unsubstituted, a $C_8$-$C_{12}$heteroaryl group which is unsubstituted or a $C_1$-$C_6$alkyl group which is unsubstituted, particularly preferably, R¹⁰ is phenyl, and/or R¹¹ and R¹² are independently of each other selected from an unsubstituted or substituted $C_1$-$C_{25}$alkyl group, preferably an unsubstituted or substituted $C_1$-$C_{18}$ alkyl group, preferably a $C_1$-$C_{12}$alkyl group, which is unsubstituted, more preferably a $C_1$-$C_4$alkyl group which is unsubstituted, and particularly preferably methyl.

Thus, it is particularly preferred that X is O, S, N-Ph, or $CMe_2$, more preferably X is O, S or NPh and even more preferably X is O or S, and most preferably X is O.

Preferred compounds of formula (Ia) are selected form particularly preferred compounds of formula (II-4)

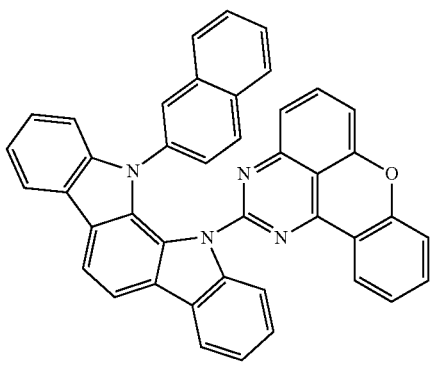

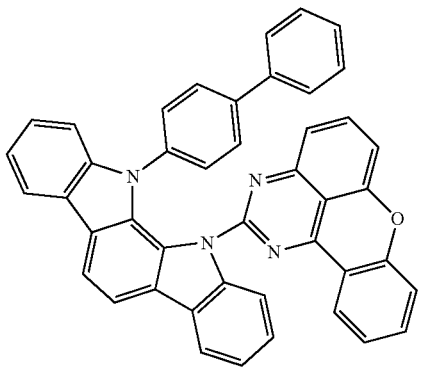

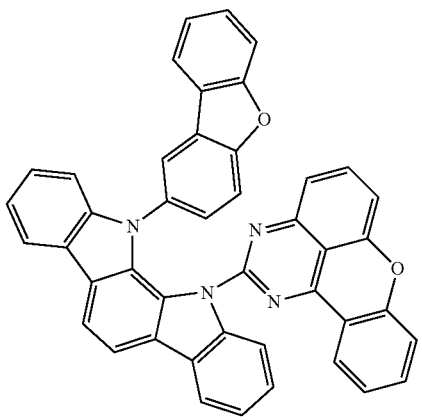

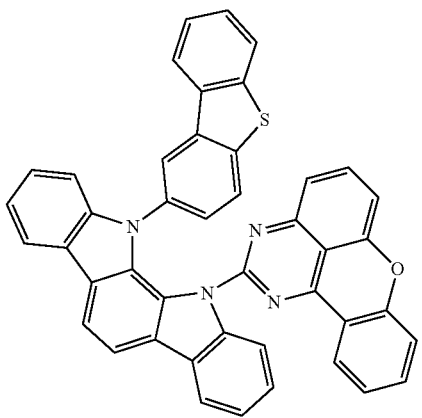

-continued
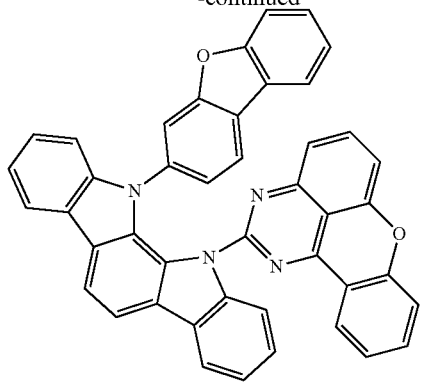
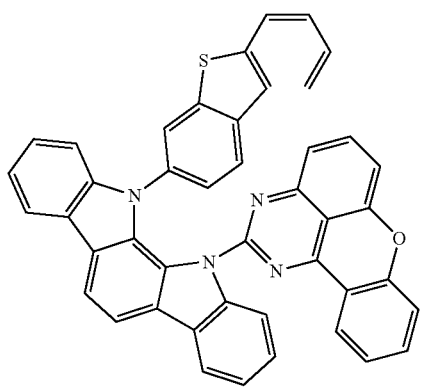
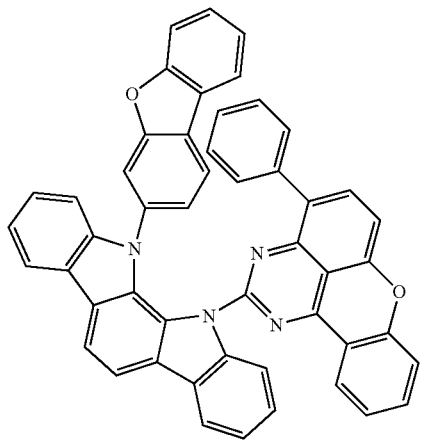
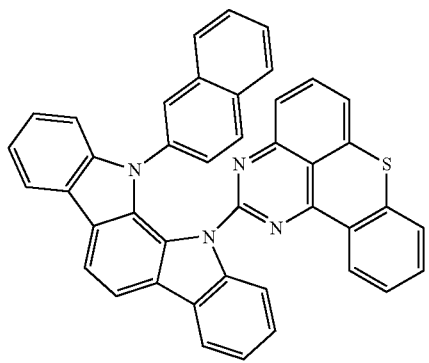
-continued
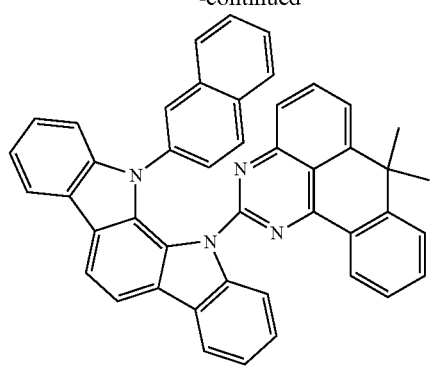
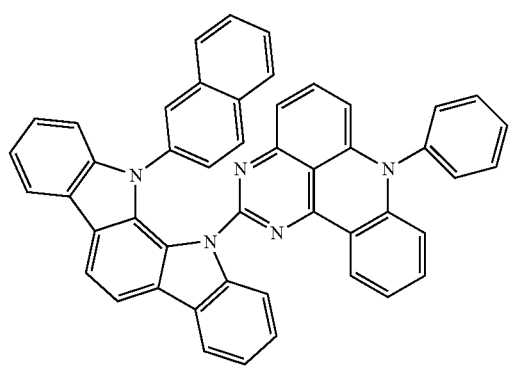
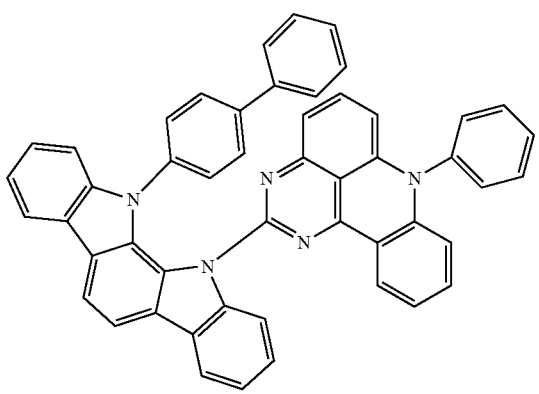
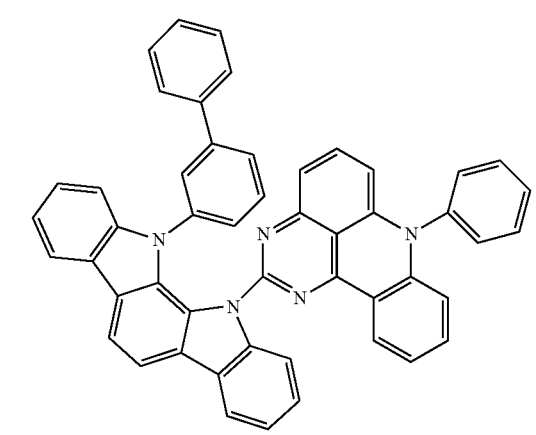

-continued
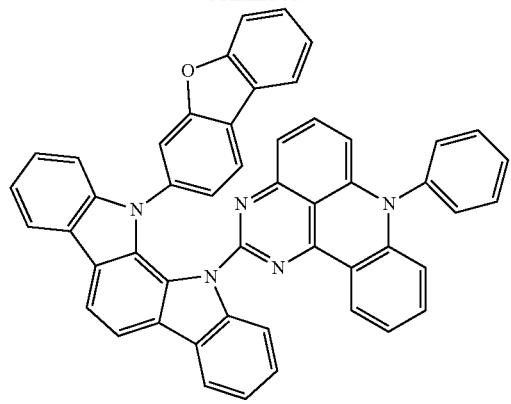
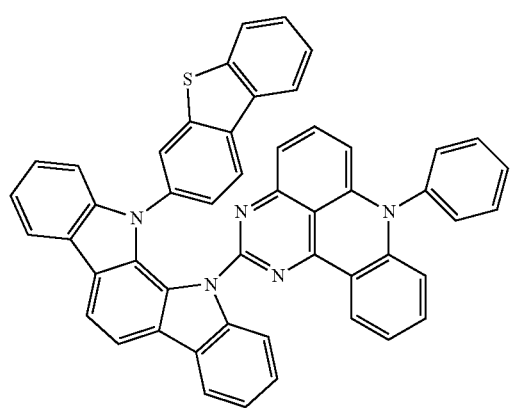
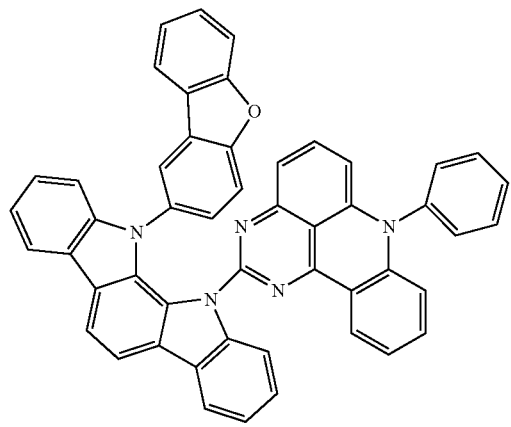
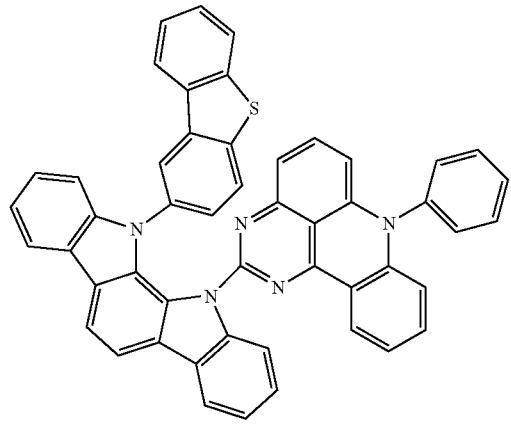
-continued
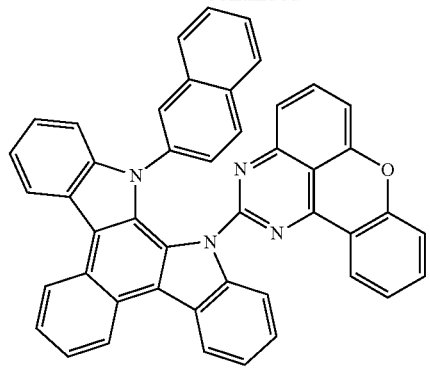 [SMILES: c1ccc2c(c1)Oc1cccc3nc(-n4c5ccccc5c5c6ccccc6c6c7ccccc7n(-c7ccc8ccccc8c7)c6c54)nc-2c13]
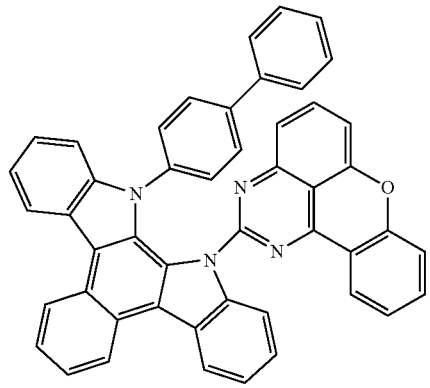
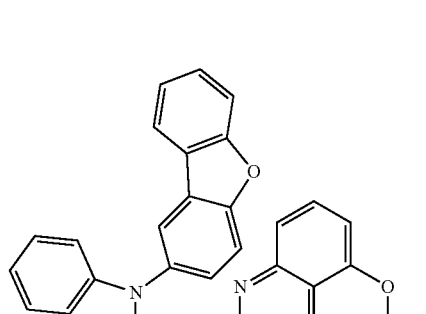
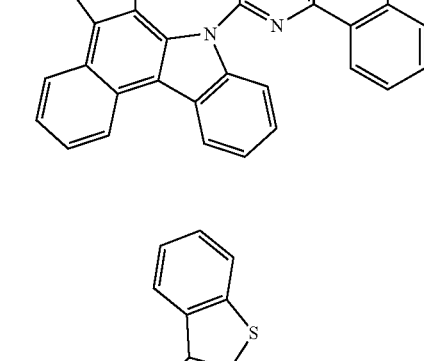
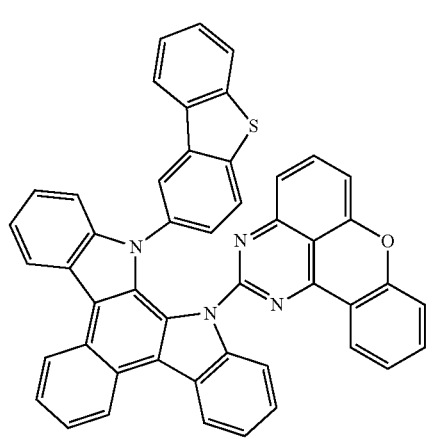

27
-continued
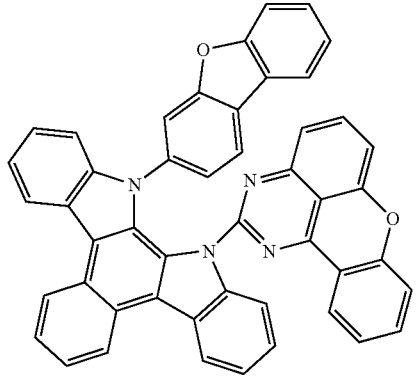
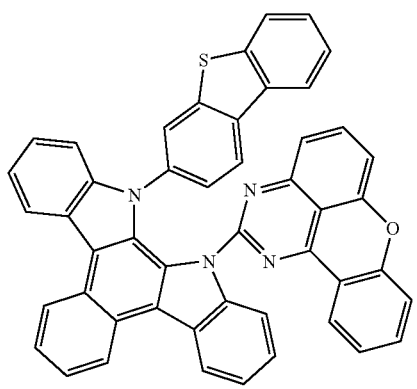
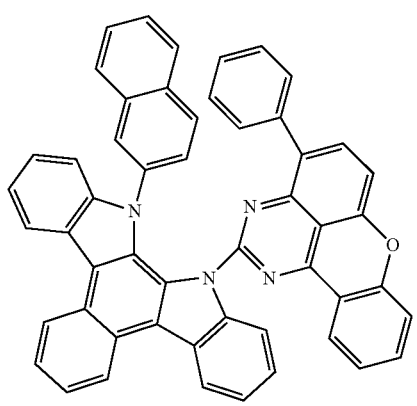
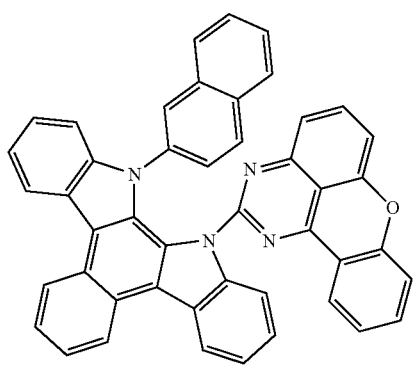
28
-continued
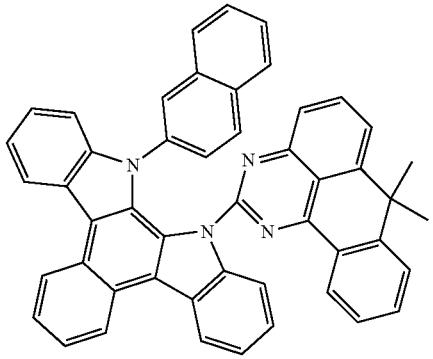
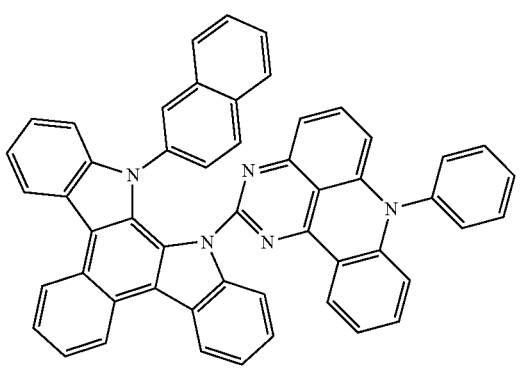
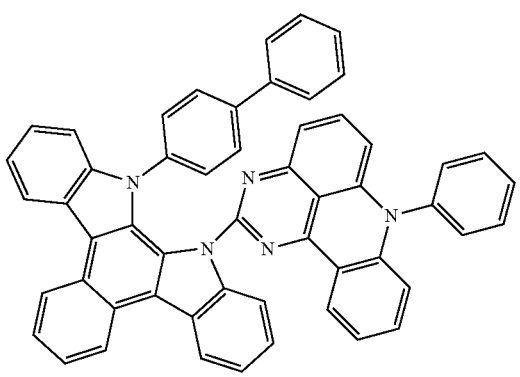
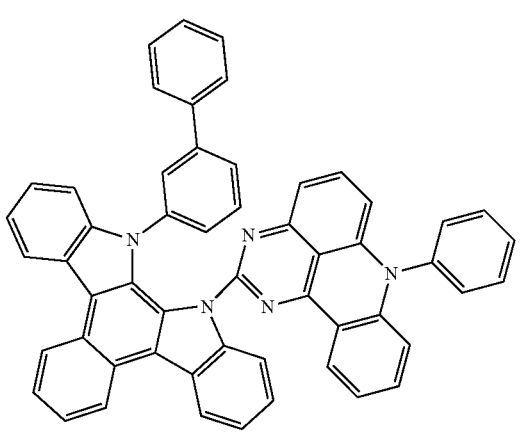

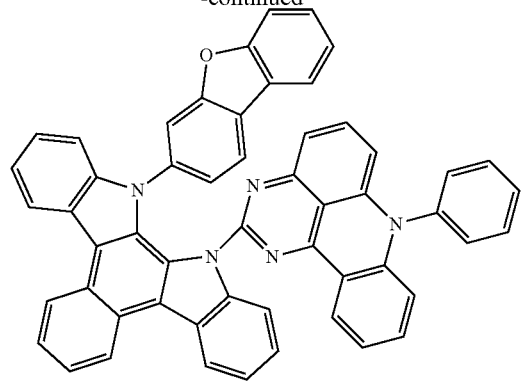
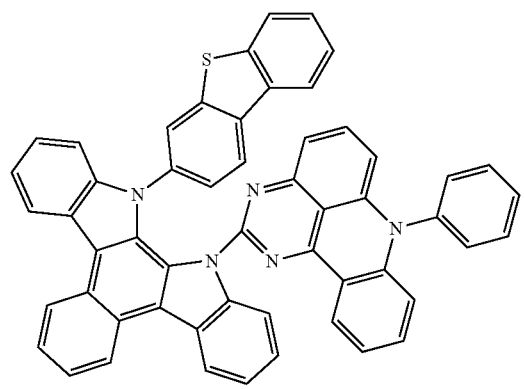
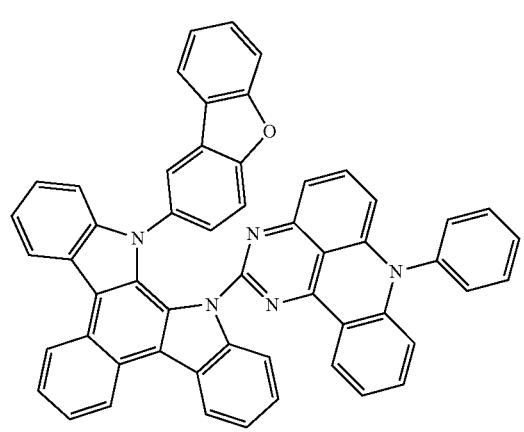
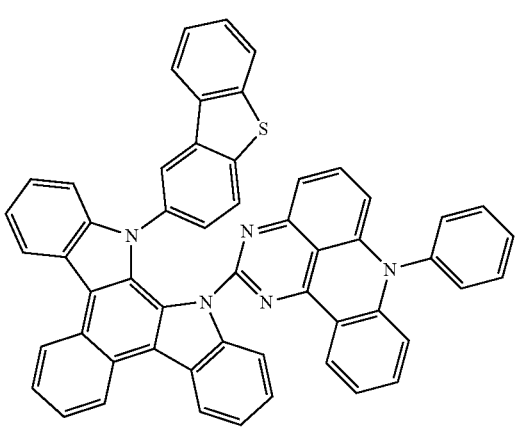
and formula (II-3):
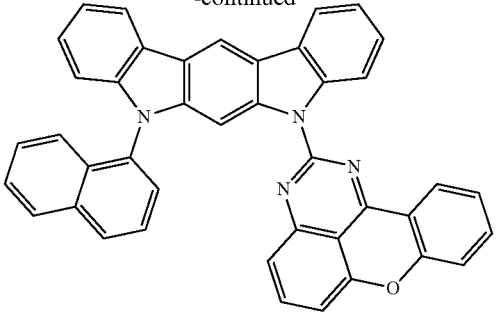
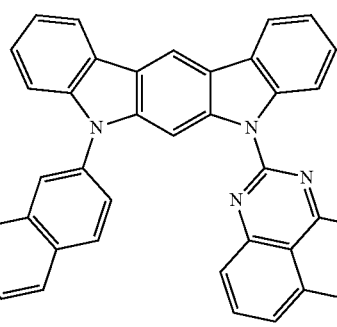
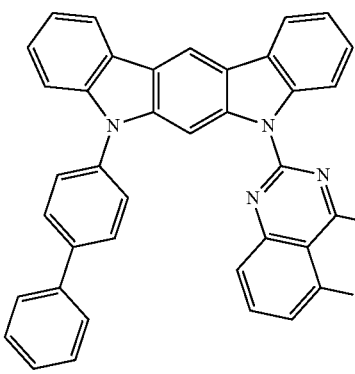
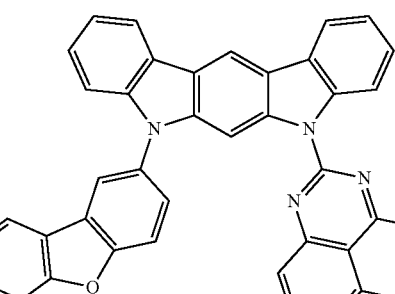
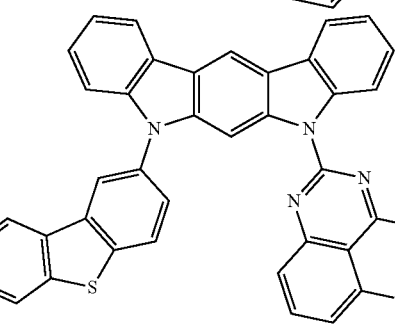

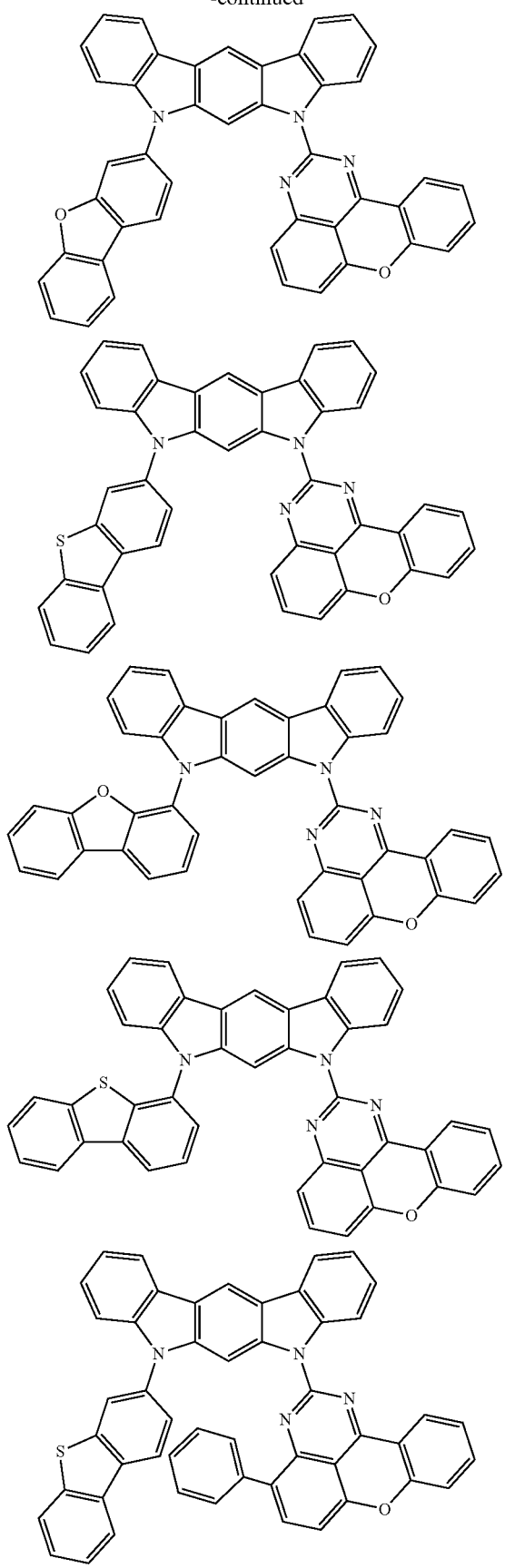
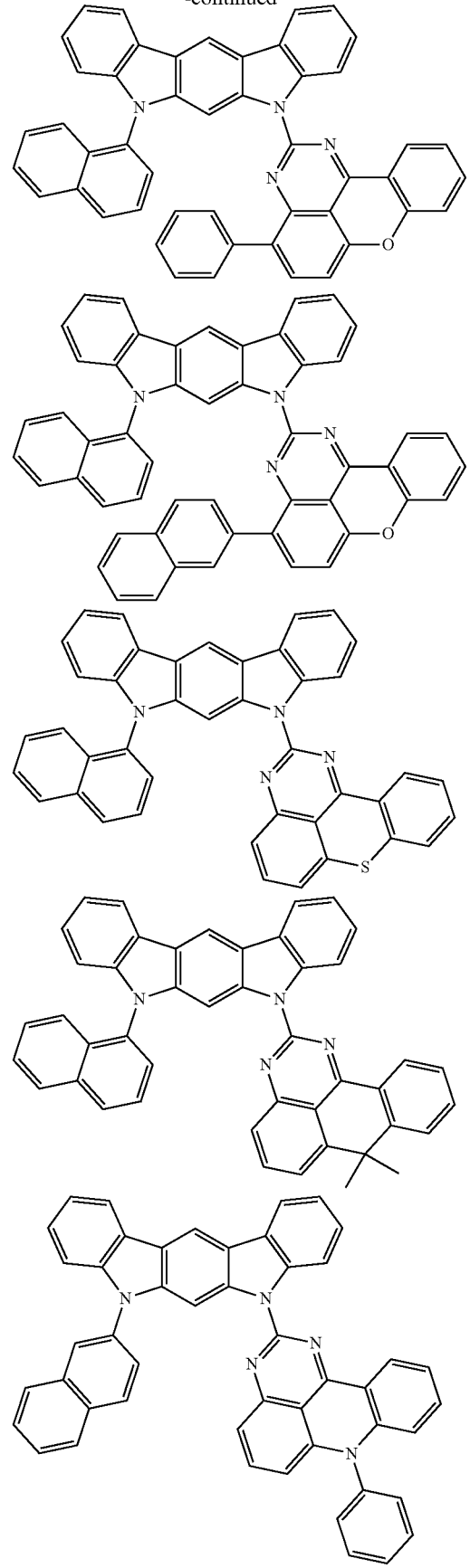

33
-continued
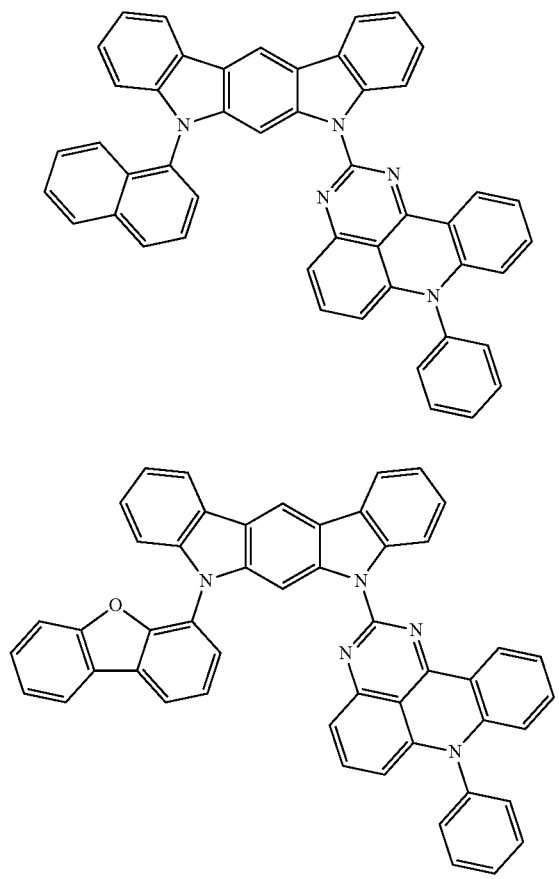
Preferred compounds of formula (Ib) are selected from particularly preferred compounds of formula (II-1)
34
-continued
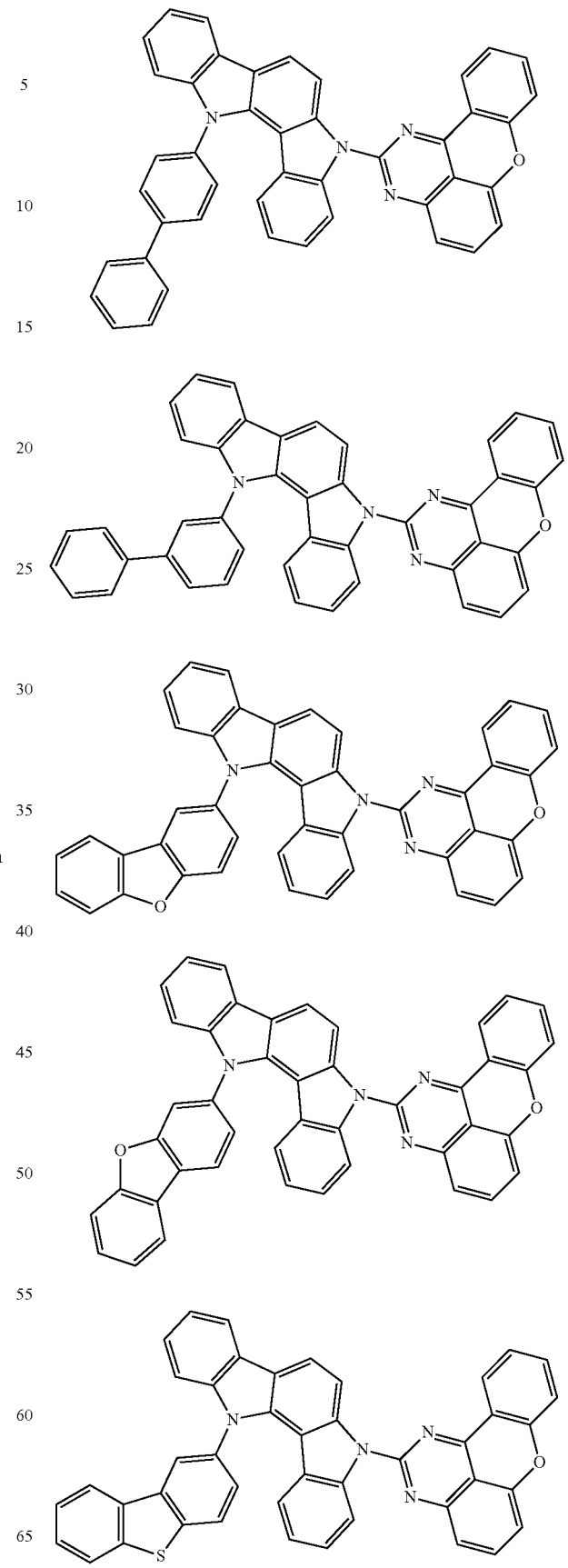

35
-continued
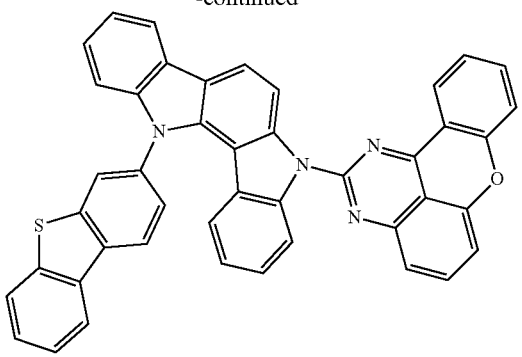
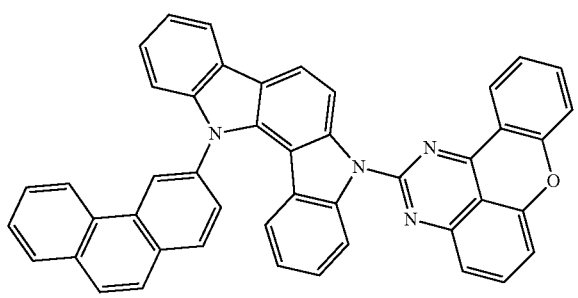
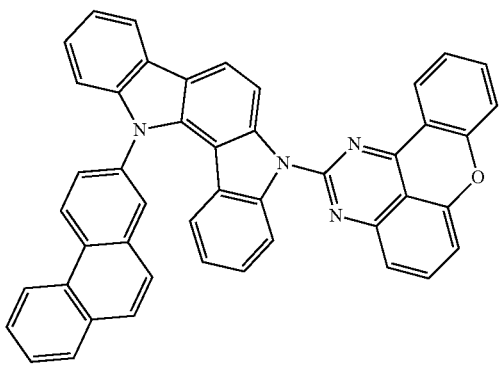
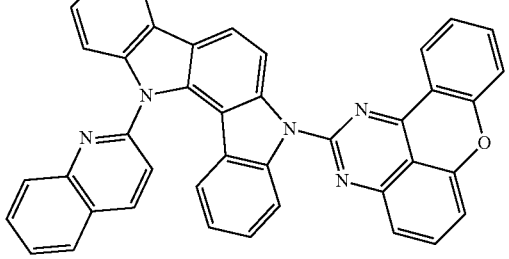
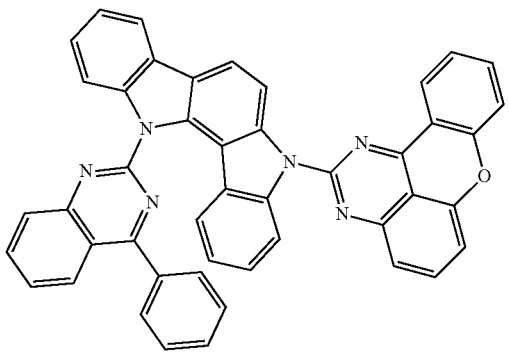
36
-continued
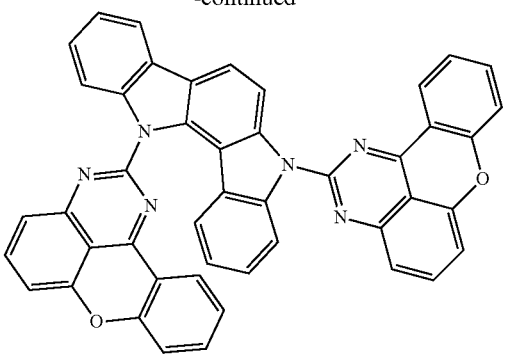
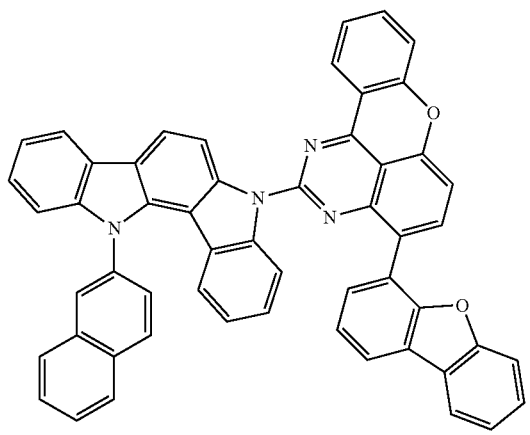
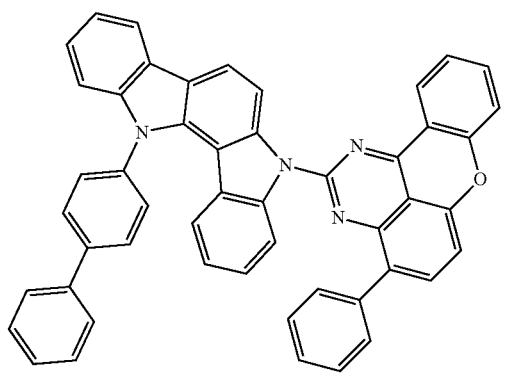
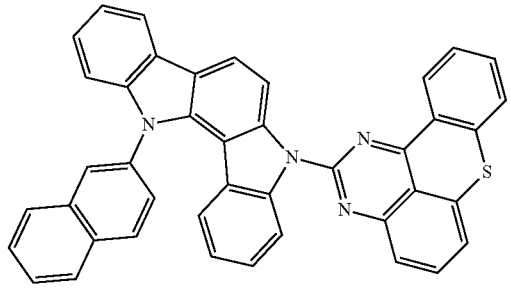

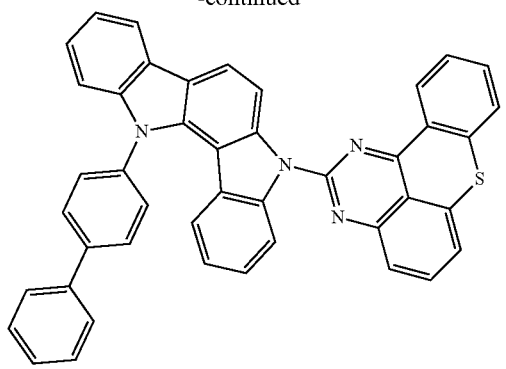
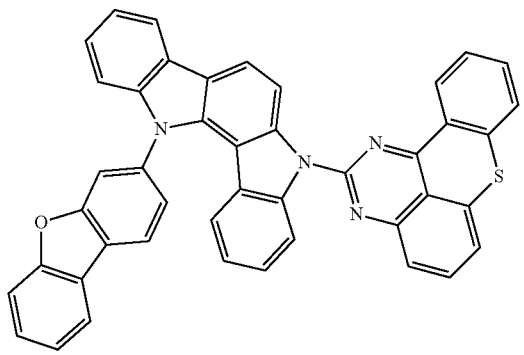
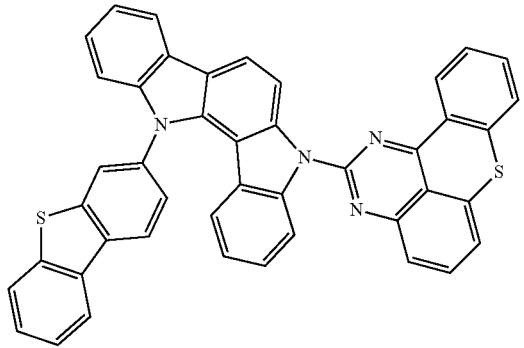
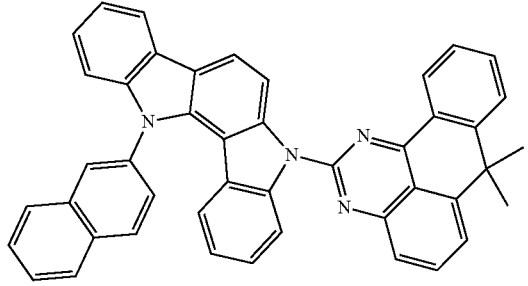
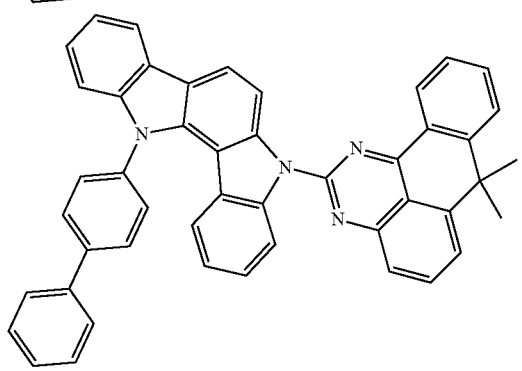
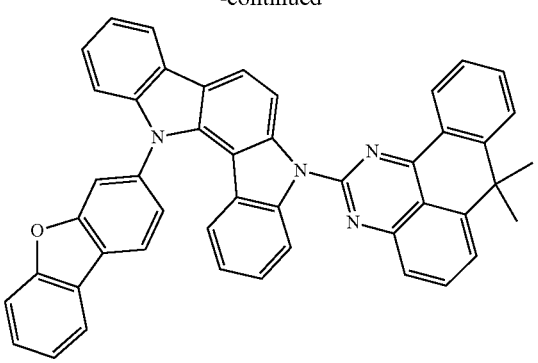
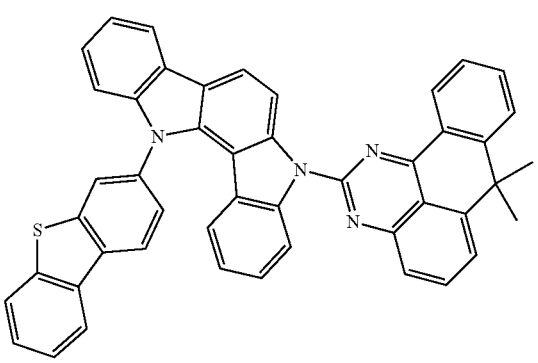
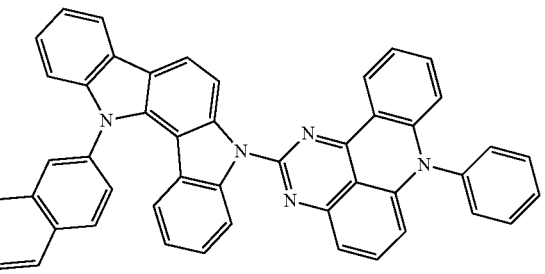
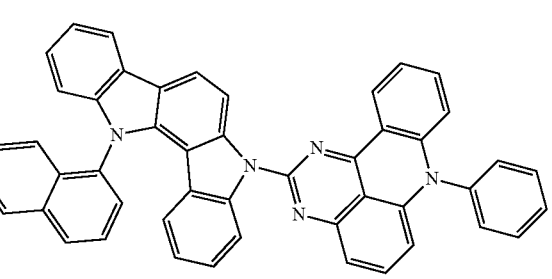
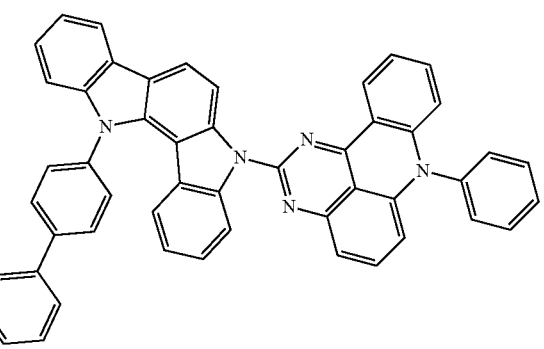

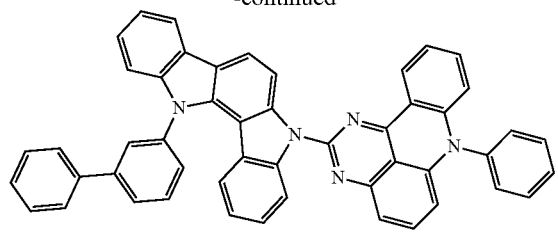
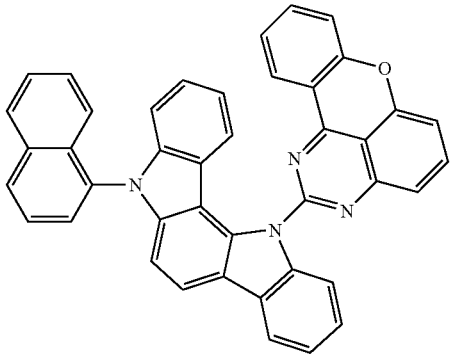
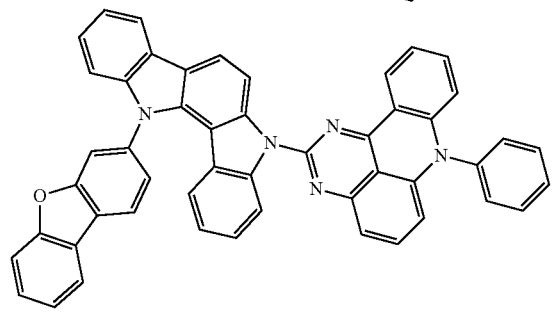
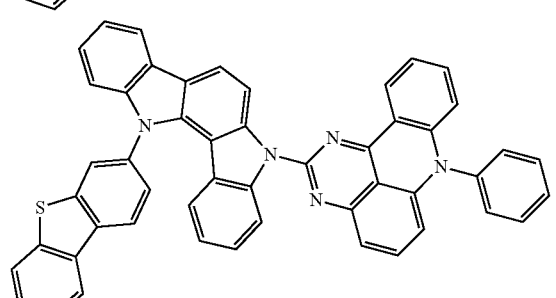
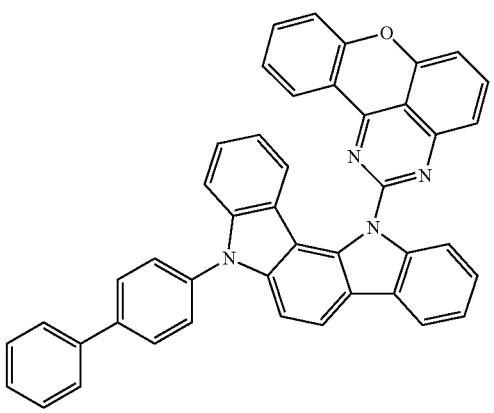
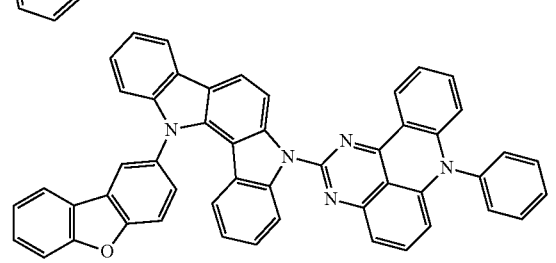
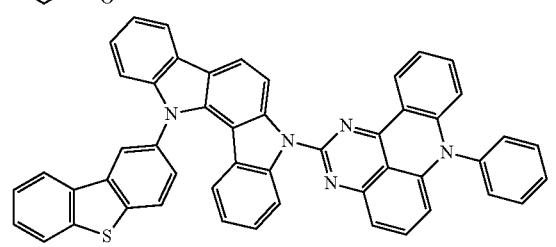
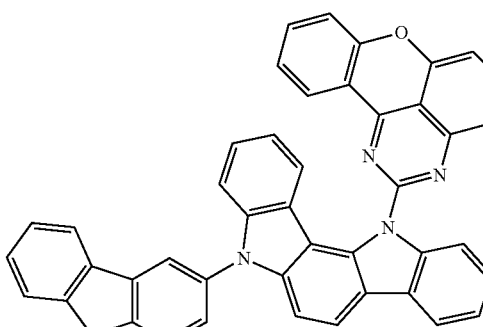
and formula (II-2):
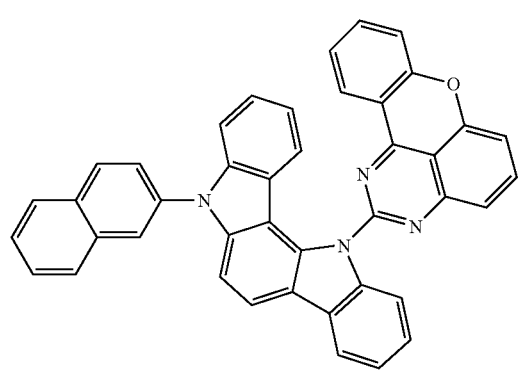
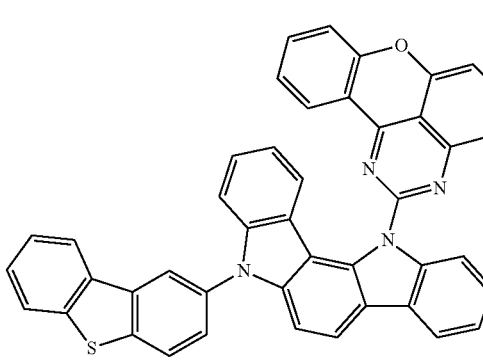

41
-continued
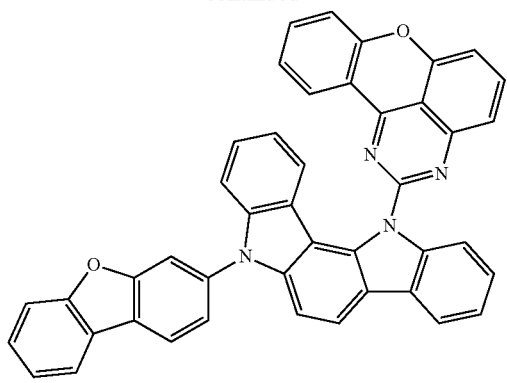
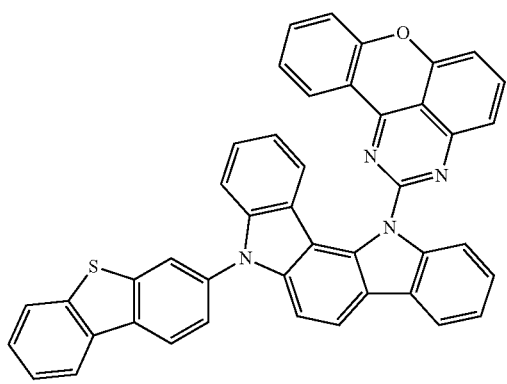
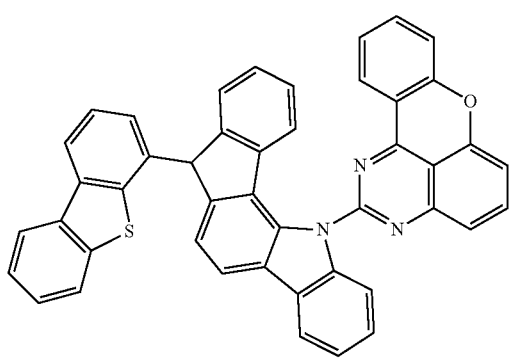
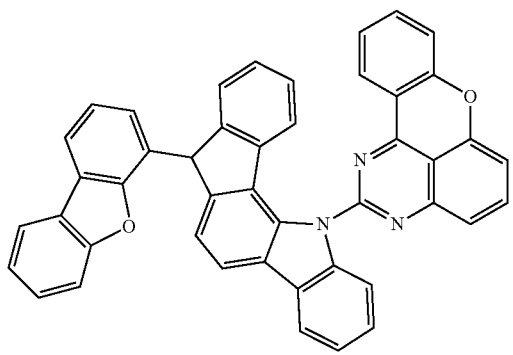
42
-continued
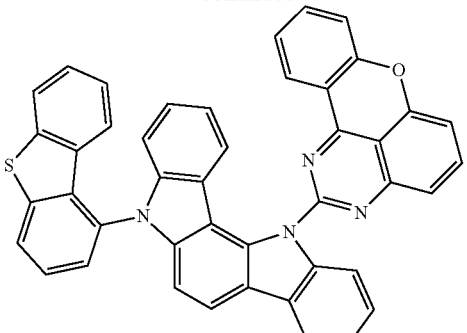
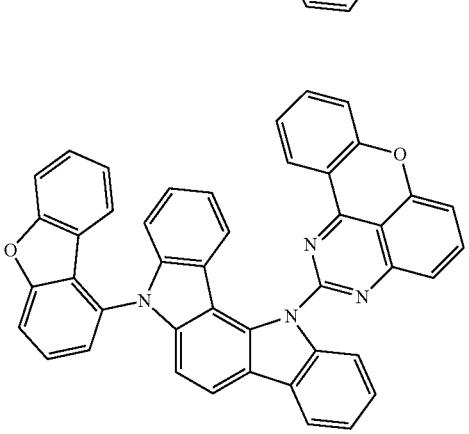
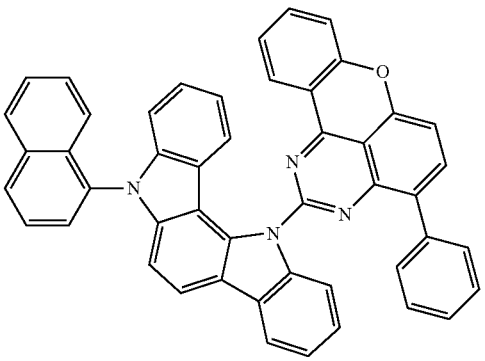
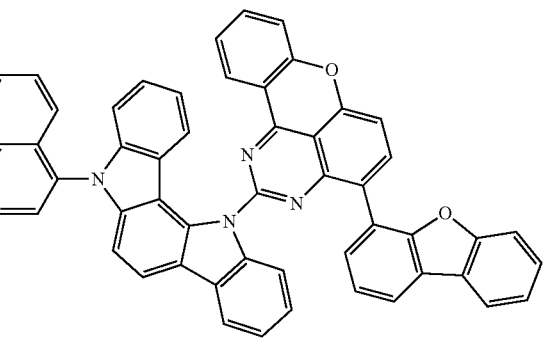

-continued
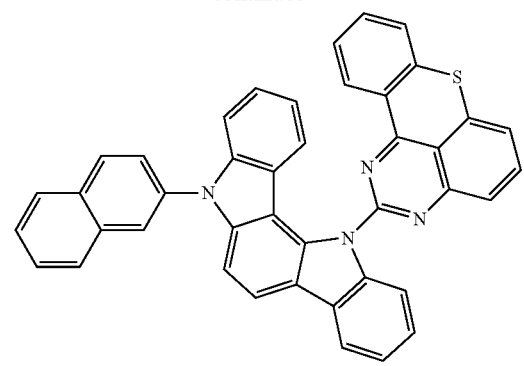
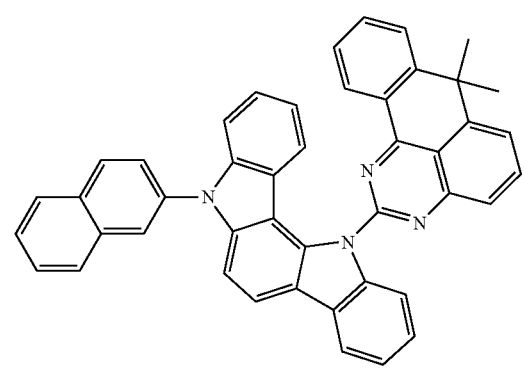
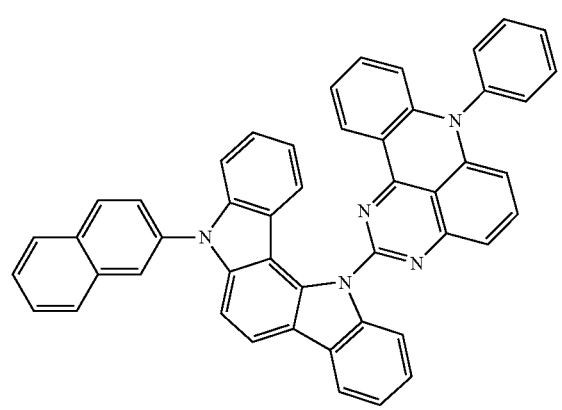
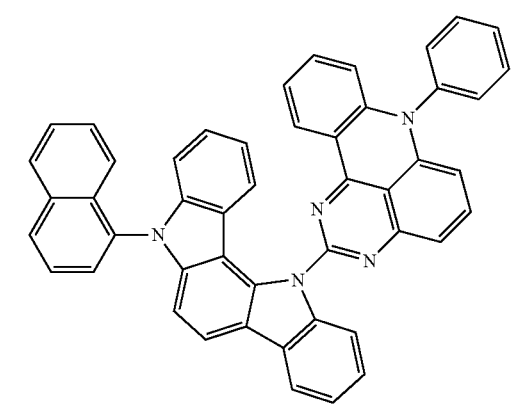
-continued
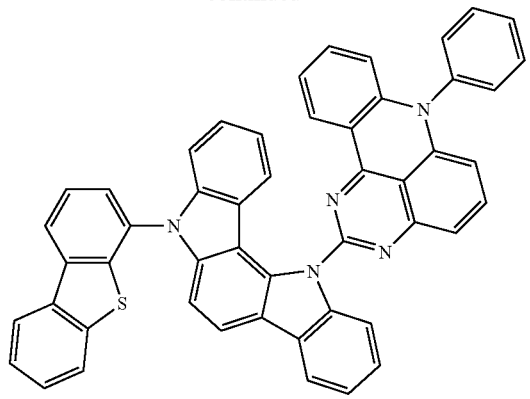
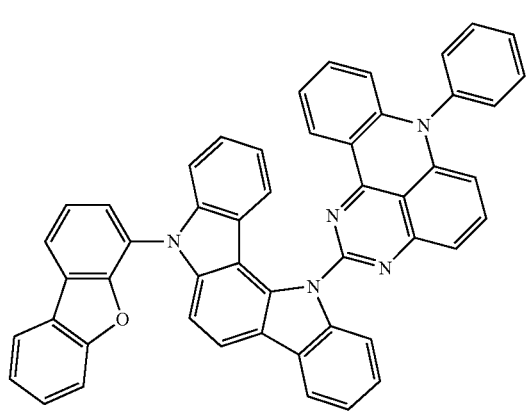
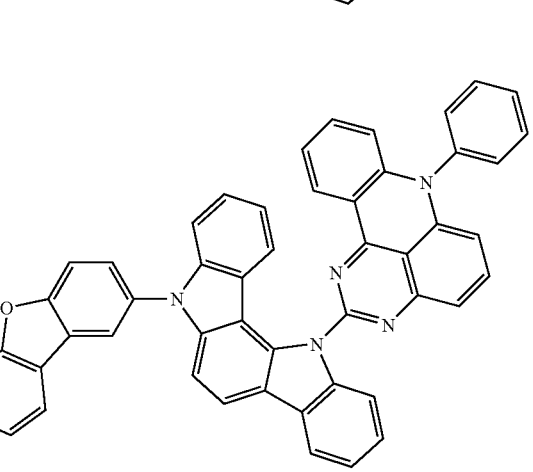
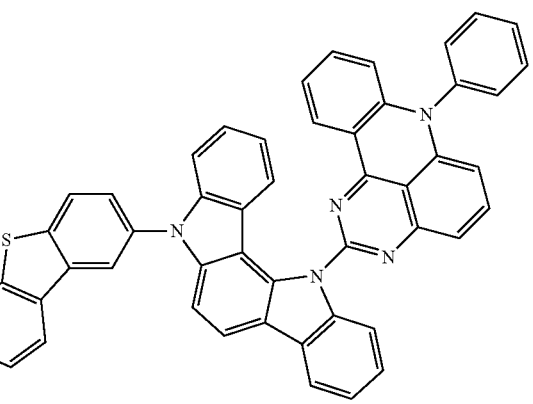

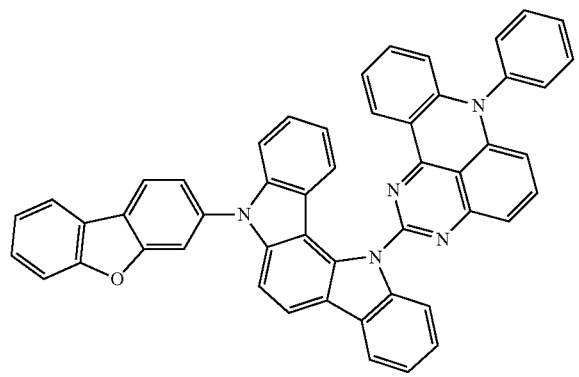
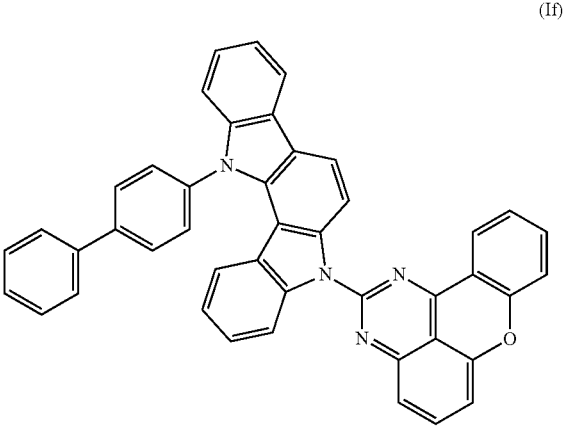
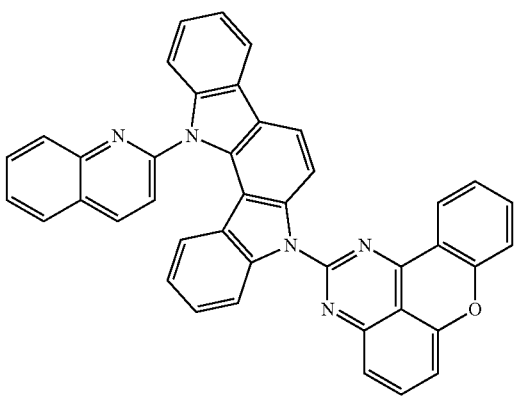
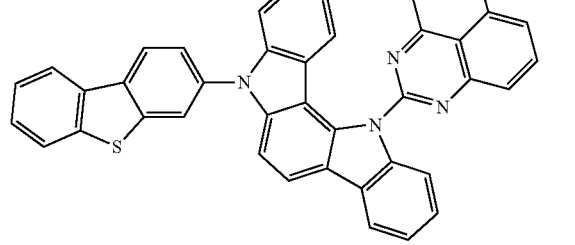
In a particularly preferred embodiment of the present invention the compound of formula (Ia) or (Ib) is represented by one of the following formulae (Ie), (If), (Ig), (Ih), (Ii), (Ij), (Ik), and (Im)
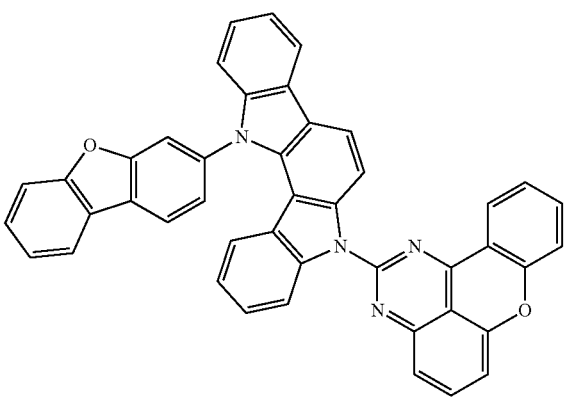
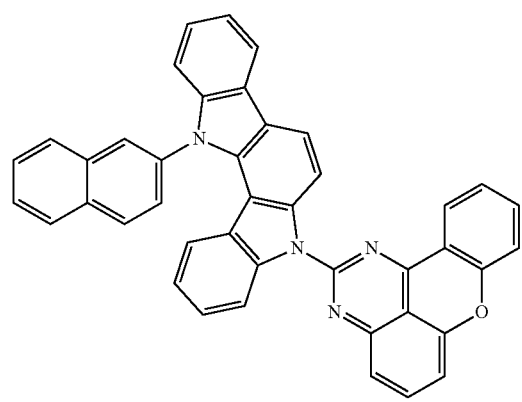
(Ie)
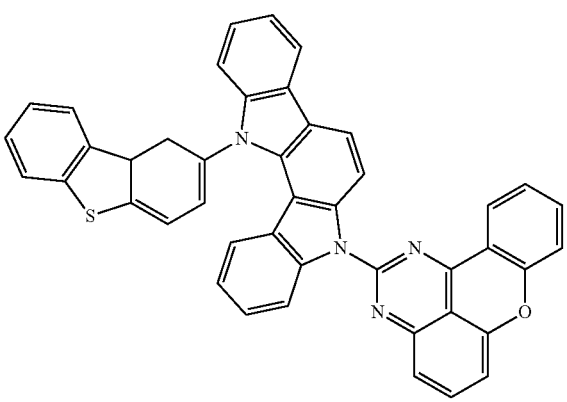
(Ii)

-continued (Ij)
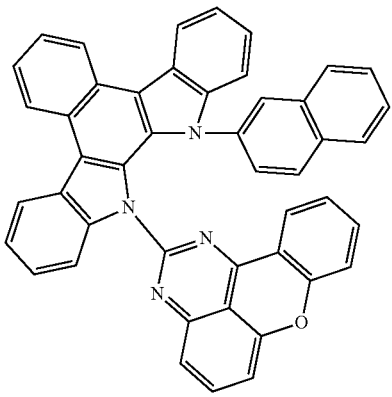

(Ik)
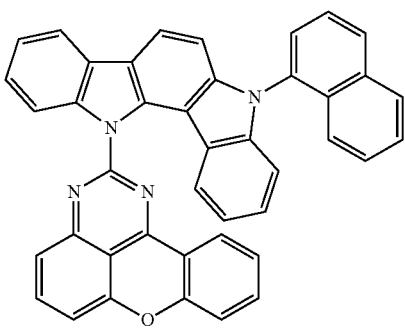

(Im)
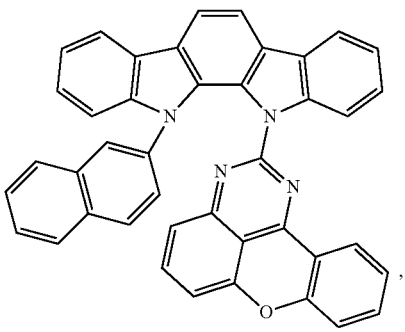

wherein compounds of formula (Ie), (If), (Ig), (Ij), (Ik), (Im) are more preferred, particularly preferred are compounds of formula (Ie), (If) and (Ig).

Preparation of the Compounds of Formula (Ia) and (Ib)

The present invention also relates to a process for the preparation of a compound according to general formula (Ia) or (Ib) as defined above, at least comprising step (A)

(A) coupling of a compound according to general formula (V)

(V)
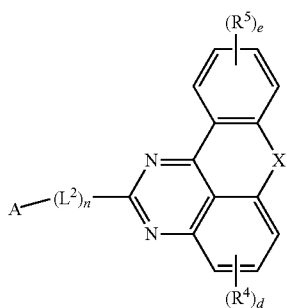

with a compound of formula (VIa) or (VIb)

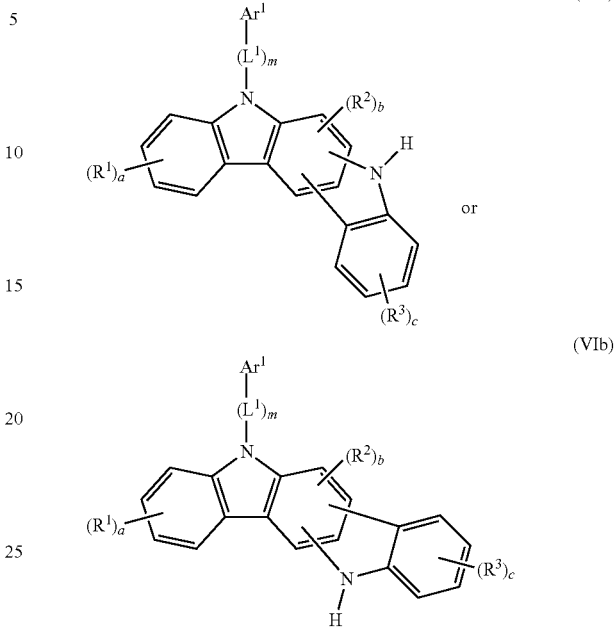

to obtain a compound according to general formula (Ia) or (Ib), wherein X, $R^1$, $R^2$, $R^3$, $R^4$, $R^5$, a, b, c, d, e, m, n, $L^1$, $L^2$ and $Ar^1$ have the meanings as defined above and A is a selected from Cl, Br, I, F, $-OSO_2CH_3$, $-OSO_2CF_3$, $-OSO_2C_6H_4CH_3$, or $-CHO$.

Step (A) of the process according to the present invention can in general be conducted by any method and under any conditions that are known to provide the desired product by a person having ordinary skill in the art. For example, step (A) of the process according to the present invention can be coupling reactions that are known to a person having ordinary skill in the art, for example reactions using palladium or copper catalysts.

The present invention therefore preferably relates to the process according to the present invention, wherein step (A) is a coupling reaction that is conducted in the presence of a palladium and/or copper catalyst.

According to one preferred embodiment, step (A) of the process according to the present invention can be conducted using the so called Buchwald-Hartwig reaction which is known to the skilled artisan and which is, for example, mentioned in *Adv. Synth. Catal.,* 2006, 23, *J. Or- Organomet. Chem.,* 1999, 125, *Chem. Sci,* 2011, 27.

According to another preferred embodiment, step (A) of the process according to the present invention can be conducted using the so called Suzuki reaction which is known to the skilled artisan and which is, for example, mentioned in *Chem. Soc. Rev.,* 2014, 3525, *Angew. Chem. Int. Ed.,* 2009, 6954.

According to another preferred embodiment, step (A) of the process according to the present invention can be conducted using the so called Ulmann reaction which is known to the skilled artisan and which is, for example, mentioned in *Chem. Rev.,* 1995, 2457, "Boronic Acids" Wiley-VCH, 2005.

In particular the coupling according to step (A) of the process according to the present invention is conducted in the presence of at least one basic compound, for example selected from the group consisting of alkali metal salts of alcohols having 1 to 6 carbon atoms, in particular sodium tert-butoxide, potassium tert-butoxide, potassium carbonate, cesium carbonate, rubidium carbonate or potassium phosphate.

The reaction is preferably conducted in at least one aprotic, organic solvent. Preferred are aromatic solvents, for example selected from the group consisting of toluene, benzene, xylene, mesitylene and mixtures thereof.

As a catalyst particularly preferably a combination of at least one Lewis acid and of at least one palladium compound is used. Particularly preferably, a combination of at least one boron comprising complex and at least one palladium salt is used, for example a combination of tert-$Bu_3P$—$HBF_4$ and $Pd_2(dba)_3$, wherein dba means dibenzylideneacetone. Other suitable ligands and/or palladium comprising reagents are mentioned in the above mentioned scientific papers.

The reaction is conducted at a temperature that is high enough to obtain the desired compound in high yield and high selectivity, for example at 40 to 160° C., preferably at 60 to 140° C., particularly preferably at 70 to 120° C.

The reaction is conducted for a time that is long enough to obtain the desired compound in high yield and high selectivity, for example for 1 to 6 h, preferably for 2 to 4 h, particularly preferably for 3 h.

After the reaction is completed, the reaction mixture can be worked up according to methods that are known to the skilled artisan, for example extraction, filtration, recrystallization, chromatography etc.

The reaction product can be analyzed, for example, by proton- or carbon-NMR, mass spectrometry etc.

The substrates that are used in step (A) of the process according to the present invention, i.e. compounds according to general formula (V) and compounds according to general formula (VIa) or (VIb) can be made by methods that are known to a person having ordinary skill in the art. The compound according to general formula (VIa) or (VIb), is, for example, commercially available.

A preferred reaction sequence to obtain the compound of formula (V) is shown in the following:

Step (A01): A compound according to general formula (VII) is transferred to a compound of general formula (VIII).

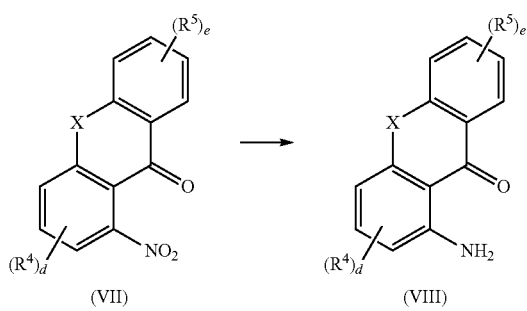

wherein X, $R^4$, $R^5$, d, and e have the same meanings as defined above. X is preferably O.

In particular the reaction according to step (A01) of the process according to the present invention is conducted in the presence of at least one reducing compound, for example selected from the group consisting of $HCO_2NH_4$ and mixtures thereof.

The reaction is preferably conducted in at least one organic solvent. Preferred are alcohols, for example selected from the group consisting of ethanol, isopropanol and mixtures thereof.

Preferably step (A01) is conducted in the presence of a catalyst. As a preferred catalyst palladium is used. Particularly preferably, palladium on carbon is used.

The reaction is conducted at a temperature that is high enough to obtain the desired compound in high yield and high selectivity, for example at 40 to 160° C., preferably at 60 to 120° C., particularly preferably at reflux temperature of the solvent.

The reaction is conducted for a time that is long enough to obtain the desired compound in high yield and high selectivity, for example for 0.2 to 6 h, preferably for 0.5 to 3 h.

After the reaction is completed, the reaction mixture can be worked up according to methods that are known to the skilled artisan, for example extraction, filtration, recrystallization, chromatography etc.

Step (A02): The compound according to general formula (VIII) is then transferred to a compound of general formula (IX).

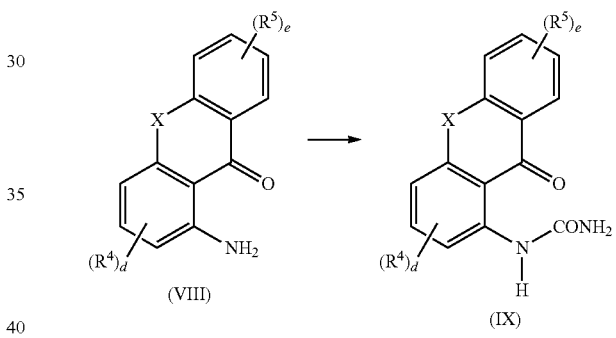

wherein X, $R^4$, $R^5$, d, and e have the same meanings as defined above. X is preferably O.

In particular the reaction according to step (A02) of the process according to the present invention is conducted in the presence of KOCN.

The reaction is preferably conducted in at least one acidic organic solvent. Preferred are carboxylic acids, for example acetic acid.

The reaction is conducted at a temperature that is high enough to obtain the desired compound in high yield and high selectivity, for example at 10 to 40° C., preferably at room temperature, i.e. 20° C.

The reaction is conducted for a time that is long enough to obtain the desired compound in high yield and high selectivity, for example for 1 to 6 h, preferably for 2 to 4 h.

After the reaction is completed, the reaction mixture can be worked up according to methods that are known to the skilled artisan, for example extraction, filtration, recrystallization, chromatography etc.

Step (A03): The compound according to general formula (IX) is then transferred to a compound of general formula (X).

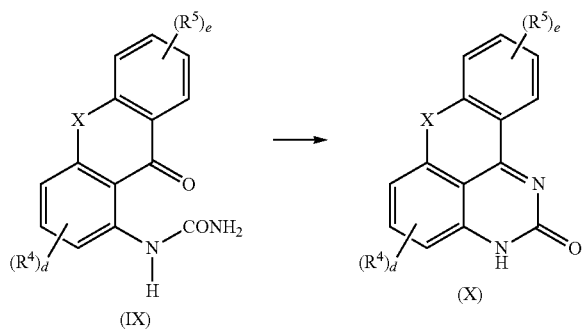

wherein X, $R^4$, $R^5$, d, and e have the same meanings as defined above. X is preferably O.

In particular the reaction according to step (A03) of the process according to the present invention is conducted in the presence of at least one basic compound selected from the group consisting of KOH, NaOH and mixtures thereof.

The reaction is preferably conducted in at least one organic solvent, for example alcohols like ethanol, isopropanol or mixtures thereof.

The reaction is conducted at a temperature that is high enough to obtain the desired compound in high yield and high selectivity, for example at 50 to 150° C., preferably at reflux temperature of the solvent.

The reaction is conducted for a time that is long enough to obtain the desired compound in high yield and high selectivity, for example for 0.1 to 2 h, preferably for 0.3 to 1 h.

After the reaction is completed, the reaction mixture can be worked up according to methods that are known to the skilled artisan, for example extraction, filtration, recrystallization, chromatography etc.

Step (A04): The compound according to general formula (X) is then transferred to a compound of general formula (XI).

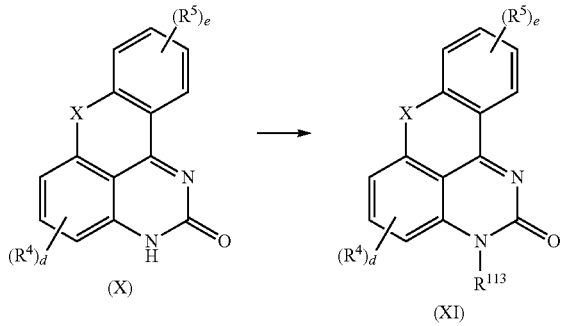

wherein X, $R^4$, $R^5$, d, and e have the same meanings as defined above and $R^{113}$ is a linear or branched $C_1$-$C_6$alkyl group, preferably methyl. X is preferably O.

In particular the reaction according to step (A04) of the process according to the present invention is conducted in the presence of at least one strongly basic compound, for example NaH.

The reaction according to step (A04) of the process according to the present invention is further conducted in the presence of at least one compound according to formula $R^{113}$-B, wherein $R^{113}$ has the meanings as mentioned above and B is selected from I, Br or Cl.

The reaction is preferably conducted in at least one organic solvent, for example dimethylformamide or mixtures thereof.

The reaction is conducted at a temperature that is high enough to obtain the desired compound in high yield and high selectivity, for example at −20 to 20° C., preferably at −10 to 10° C., most preferably at 0° C.

The reaction is conducted for a time that is long enough to obtain the desired compound in high yield and high selectivity, for example for 0.5 to 4 h, preferably for 1 to 3 h.

After the reaction is completed, the reaction mixture can be worked up according to methods that are known to the skilled artisan, for example extraction, filtration, recrystallization, chromatography etc.

Step (A05): The compound according to general formula (XI) is then transferred to a compound of general formula (V).

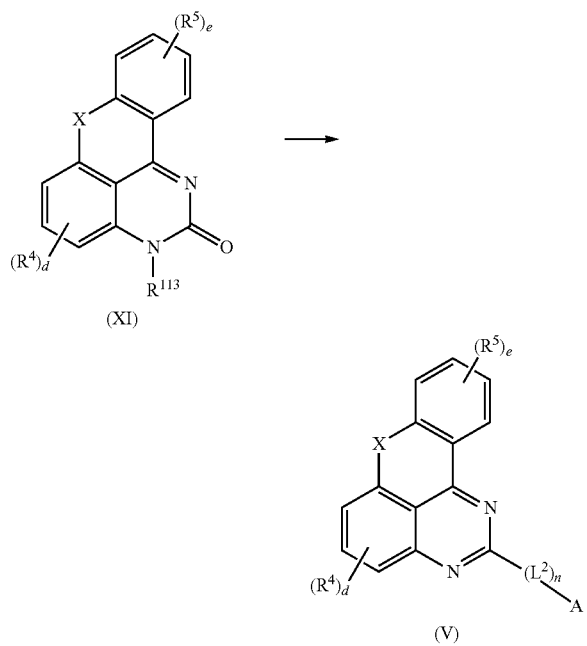

wherein X, $R^4$, $R^5$, $R^{113}$, d, e, n, $L^2$ and A have the same meanings as defined above. X is preferably O.

In particular, the reaction according to step (A05) according to the present invention is conducted in the presence of at least one compound, which is able to introduce the moiety -($L^2$)$_n$-A into the molecule. According to the preferred case that A is Cl and $L^2$ is a direct bond, chlorination agents are used, for example phosphorous comprising chlorination agents like $POCl_3$ or $PCl_5$ in step (A05) of the process according to the present invention The reaction according to step (A05) is preferably conducted without any solvent.

The reaction is conducted at a temperature that is high enough to obtain the desired compound in high yield and high selectivity, for example at 40 to 160° C., preferably at 60 to 120° C., particularly preferably at 70 to 90° C.

The reaction is conducted for a time that is long enough to obtain the desired compound in high yield and high selectivity, for example for 1 to 6 h, preferably for 2 to 4 h.

After the reaction is completed, the reaction mixture can be worked up according to methods that are known to the skilled artisan, for example extraction, filtration, recrystallization, chromatography etc.

Further detailed reaction conditions of this reaction scheme for obtaining the compound of formula (V) can be taken from Carlos M. Martinez et al., *J. Heterocyclic Chem.*, 44, 1035 (2007).

Particularly preferably, the process according to the present invention for the preparation of compounds according to general formula (Ia) or (Ib) comprises step (A01), followed by step (A02), followed by step (A03), followed by step (A04), followed by step (A05), followed by step (A).

According to another preferred embodiment of the process according to the present invention, the compound according to general formula (V) can also be obtained directly from compound of general formula (X) using reaction conditions as mentioned in respect of step (A05). The present invention therefore preferably relates to the process according to the present invention, wherein the compound according to general formula (V) can also be obtained directly from compound of general formula (X) as shown in the following step (A05a):

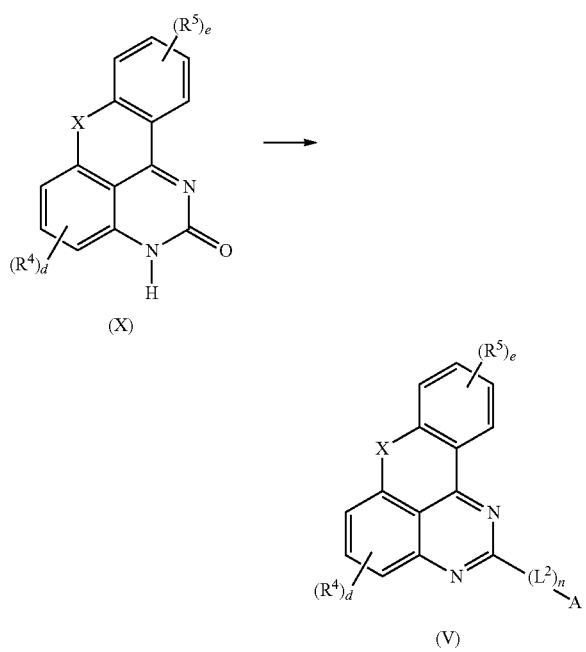

Therefore, particularly preferably, the process according to the present invention for the preparation of compounds according to general formula (I) comprises step (A01), followed by step (A02), followed by step (A03), followed by step (A05a), followed by step (A).

According to the further preferred embodiment that X is S, the process according to the present invention for the preparation of compounds according to general formula (Ia) or (Ib) comprises step (A01), followed by step (A02), followed by step (A03), followed by step (A05a), followed by step (A).

Compound (VII) as mentioned above can be prepared in chemical reactions that are known to the skilled artisan. Preferred methods for the preparation of the compound according to general formula (VII) are mentioned in Yamagami, Isao et al., Jpn. Kokai Tokkyo Koh, 2008273906, 2008, Kralj, Ana et al., *ChemMedChem*, 9(1), 151-168, 2014 and Okabayashi, Ichizo and Iwata, Noriko, *Chemical and Pharmaceutical Bulletin*, 28(9), 2831-5, 1980.

The compound according to general formula (V) as mentioned above can also be prepared by further methods that are explained in the following. For example, the compound according to general formula (V) can be prepared from a compound according to general formula (V*):

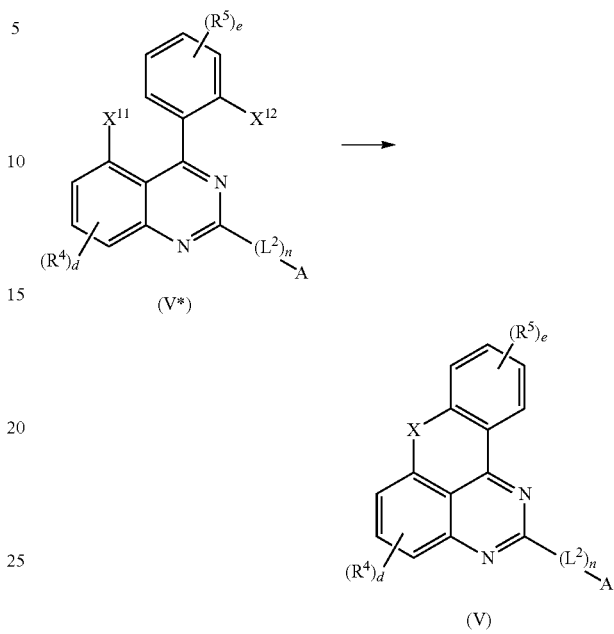

wherein X, $R^4$, $R^5$, d, e, n, $L^2$ and A have the same meanings as defined above. If X=O, then $X^{11}$ and $X^{12}$ are preferably independently of each other F or OH. If X=$NR^{10}$, then $X^{11}$ and $X^{12}$ are preferably independently of each other F or OH or $NHR^{10}$, wherein $R^{10}$ has the same meaning as defined above. If X=S, then $X^{11}$ and $X^{12}$ are preferably independently of each other H or S(O)$CH_3$. If X=$CR^{11}R^{12}$, then $X^{11}$ and $X^{12}$ are preferably independently of each other H or $CR^{11}R^{12}$—OH, wherein $R^{11}$ and $R^{12}$ have the same meanings as defined above.

According to the preferred embodiment that X is O, the following reaction is conducted (step (A06)):

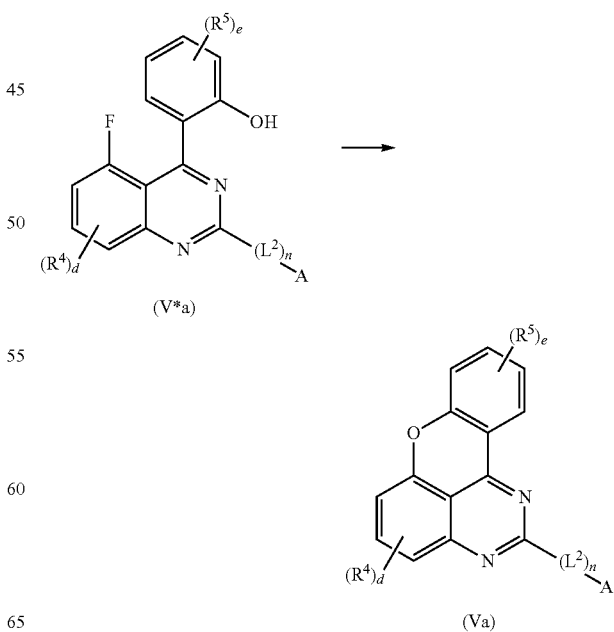

According to this preferred embodiment (step (A06)) the compound according to general formula (V*a) is transferred into the compound according to general formula (Va), wherein $R^4$, $R^5$, d, e, n, $L^2$ and A have the same meanings as defined above.

The reaction is preferably conducted in the presence of at least one basic compound, for example selected from the group consisting of $K_2CO_3$, NaH, NaOH and mixtures thereof. Further reaction conditions like temperature, solvent, reaction time etc. are known to the person having ordinary skill in the art.

The compound according to general formula (V*a) can be obtained by any method that is known to the skilled artisan. Preferably the compound according to general formula (V*a) is obtained according to the method described in Kang Hyun-Ju et al., WO 2014088290 or Welsh Dean M et al., Jpn. Kokai Tokkyo Koh, 2014183315, 2014.

According to the preferred embodiment that X is S, the following reaction is conducted (step (A07)):

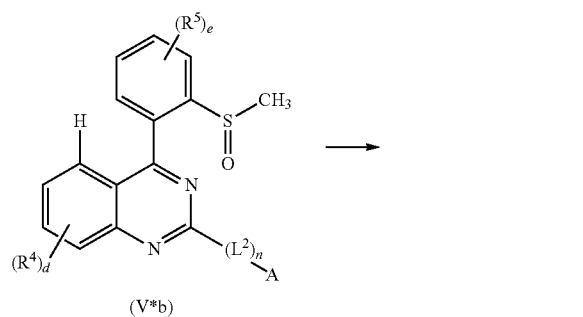

(V*b)

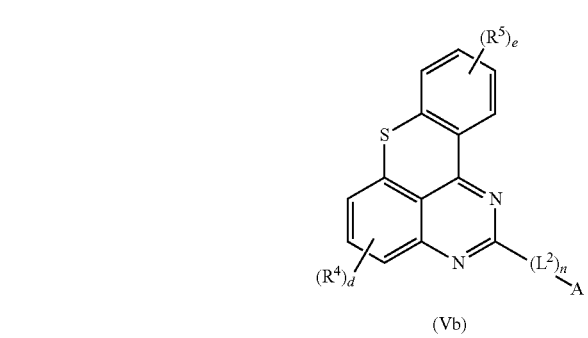

(Vb)

According to this preferred embodiment (step (A07)) the compound according to general formula (V*b) is transferred into the compound according to general formula (Vb), wherein $R^4$, $R^5$, d, e, n, $L^2$ and A have the same meanings as defined above.

The reaction is preferably conducted in the presence of at least one acidic compound, for example selected from the group consisting of $(CF_3SO_2)_2$, $CF_3SO_2OH$, and mixtures thereof.

Further reaction conditions like temperature, solvent, reaction time etc. are known to the person having ordinary skill in the art.

According to the preferred embodiment that X is $NR^{10}$, the following reaction is conducted (step (A08)):

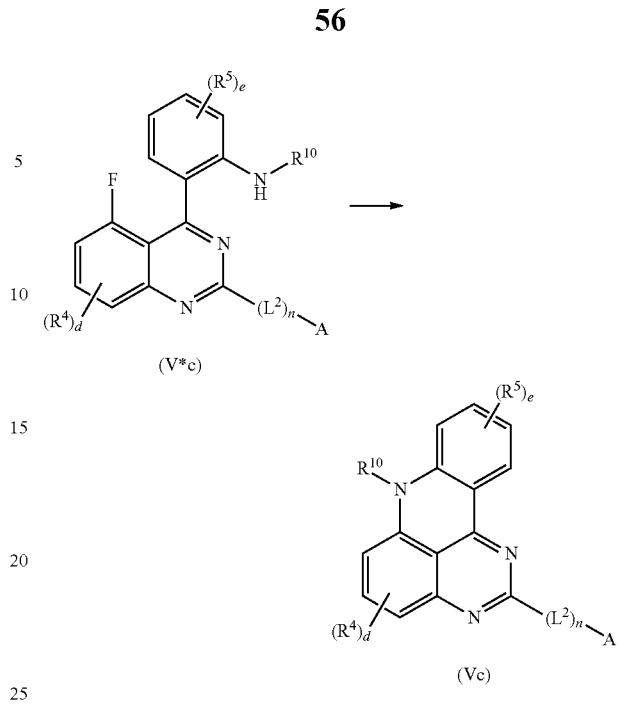

(V*c)

(Vc)

According to this preferred embodiment (step (A08)) the compound according to general formula (V*c) is transferred into the compound according to general formula (Vc), wherein $R^4$, $R^6$, $R^{10}$, d, e, n, $L^2$ and A have the same meanings as defined above.

The reaction is preferably conducted in the presence of at least one basic compound, for example selected from the group consisting of $K_2CO_3$, NaH, NaOH and mixtures thereof. Further reaction conditions like temperature, solvent, reaction time etc. are known to the person having ordinary skill in the art.

The compound according to general formula (V*c) can be obtained by any method that is known to the skilled artisan. Preferably the compound according to general formula (V*c) is obtained according to the method described in Kim Byung-Ku et al., WO 2016006791 or Morris Scott et al., *Advanced Synthesis&Catalysis*, 357(10), 2311-6, 2015.

Compounds of Formula (Ia) and (Ib) According to the Present Invention in Organic Electronics Applications In the following applications of the compounds of formula (Ia) and (Ib) according to the present invention as mentioned above in organic electronic applications will be explained.

It has been found that the compounds of formula (Ia) and (Ib) according to the present invention are particularly suitable for use in applications in which charge carrier conductivity is required, especially for use in organic electronics applications, more preferably for use in organic light-emitting diodes (OLEDs).

The compounds of formula (Ia) and (Ib) according to the present invention being particularly suitable in OLEDs for use in a light-emitting layer, wherein the compound of formula (Ia) respectively the compound of formula (Ib) is preferably used as a host material, a charge transporting material, charge and/or exciton blocking material.

In a preferred embodiment, the compounds of formula (Ia) and the compounds of formula (Ib) according to the present invention are present in OLEDs as a host, as a single host or as a host in combination with one or more further hosts.

The present invention therefore relates to an electronic device, preferably an organic electroluminescent device, more preferably an organic light emitting diode (OLED), comprising at least one compound of formula (Ia) or (Ib) according to the present invention.

The present invention preferably further relates to the electronic device according to the present invention, preferably an organic electroluminescence device, more preferably an organic light emitting diode (OLED), comprising a cathode, an anode, and a plurality of organic thin film layers provided between the cathode and the anode, the plurality of organic thin film layers comprising at least one compound of formula (Ia) or (Ib) according to the present invention.

The present invention preferably further relates to the electronic device according to the present invention, preferably an organic electroluminescence device, more preferably an organic light emitting diode (OLED), comprising a cathode, an anode, and a plurality of organic thin film layers provided between the cathode and the anode, the plurality of organic thin film layers comprising at least one emitting layer comprising at least one compound of formula (Ia) or (Ib) according to the present invention.

The present invention further relates to an electronic equipment comprising the organic electroluminescence device according to the present invention.

The present invention also relates to an emitting layer, preferably present in an electronic device, more preferably in an electroluminescence device, particularly preferably in an organic light emitting diode (OLED), comprising at least one compound of formula (Ia) or (Ib) according to the present invention.

The present invention preferably further relates to the use of at least one compound of formula (Ia) or (Ib) according to the present invention in an electronic device, preferably in an electroluminescence device, particularly preferably in an organic light emitting diode (OLED), preferably in an emitting layer.

According to the present application, the terms matrix and host are used interchangeably.

Suitable structures of organic electronic devices, especially organic light-emitting diodes (OLEDs), are known to those skilled in the art and are specified below.

For example, the electronic device, preferably an organic electroluminescence device, more preferably an organic light emitting diode (OLED), according to the present invention comprises a cathode, an anode, and a plurality of organic thin film layers provided between the cathode and the anode, the organic thin film layers comprising at least one compound of formula (Ia) or (Ib) according to the present invention.

Preferably, the present invention provides an organic light-emitting diode (OLED) comprising an anode and a cathode and a light-emitting layer arranged between the anode and the cathode, and if appropriate at least one further layer selected from the group consisting of at least one blocking layer for holes/excitons, at least one blocking layer for electrons/excitons, at least one hole injection layer, at least one hole transport layer, at least one electron injection layer and at least one electron transport layer, wherein the OLED comprises at least one compound of formula (Ia) or (Ib) according to the present invention.

The present application further relates to a light-emitting layer, preferably present in an electronic device, more preferably in an electroluminescence device, particularly preferably in an organic light emitting diode (OLED), comprising at least one compound of formula (Ia) or (Ib) according to the present invention. Examples of preferred compounds according to general formulae (Ia) and (Ib) are shown above.

Most preferably, the electronic device according to the present invention is an organic light emitting diode (OLED).

Structure of the Inventive OLED

The inventive organic light-emitting diode (OLED) thus generally has the following structure: an anode (a) and a cathode (i) and a light-emitting layer (e) arranged between the anode (a) and the cathode (i).

The inventive OLED may, for example—in a preferred embodiment—be formed from the following layers:
1. Anode (a)
2. Hole transport layer (c)
3. Light-emitting layer (e)
4. Blocking layer for holes/excitons (f)
5. Electron transport layer (g)
6. Cathode (i)

Layer sequences different than the aforementioned structure are also possible, and are known to those skilled in the art. For example, it is possible that the OLED does not have all of the layers mentioned; for example, an OLED with layers (a) (anode), (e) (light-emitting layer) and (i) (cathode) is likewise suitable, in which case the functions of the layers (c) (hole transport layer) and (f) (blocking layer for holes/excitons) and (g) (electron transport layer) are assumed by the adjacent layers. OLEDs which have layers (a), (c), (e) and (i), or layers (a), (e), (f), (g) and (i), are likewise suitable. In addition, the OLEDs may have a blocking layer for electrons/excitons (d) between the hole transport layer (c) and the light-emitting layer (e).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole transport layer, in one embodiment, may simultaneously block excitons and/or electrons.

Furthermore, the individual layers of the OLED among those specified above may in turn be formed from two or more layers. For example, the hole transport layer may be formed from a layer into which holes are injected from the electrode, and a layer which transports the holes away from the hole-injecting layer into the light-emitting layer. The electron transport layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used in accordance with the invention.

In a preferred embodiment the OLED according to the present invention comprises in this order:
(a) an anode,
(b) optionally a hole injection layer,
(c) optionally a hole transport layer,
(d) optionally an exciton blocking layer,
(e) an emitting layer,
(f) optionally a hole/exciton blocking layer,
(g) optionally an electron transport layer,
(h) optionally an electron injection layer, and
(i) a cathode.

In a particularly preferred embodiment the OLED according to the present invention comprises in this order:
(a) an anode,
(b) optionally a hole injection layer,
(c) a hole transport layer,
(d) an exciton blocking layer
(e) an emitting layer,
(f) a hole/exciton blocking layer
(g) an electron transport layer, and
(h) optionally an electron injection layer, and
(i) a cathode.

The properties and functions of these various layers, as well as example materials are known from the prior art and are described in more detail below on basis of preferred embodiments.

The least one compound of formula (Ia) or (Ib) according to the present invention may be present in any layer of the OLED, preferably a host material, a charge transporting material, charge and/or exciton blocking material. More preferably, the least one compound of formula (Ia) or (Ib) according to the present invention are present as host material in the emitting layer of the OLED.

FIG. 1 shows a schematic configuration of one example of the organic EL device of the invention. The organic EL device 1 comprises a substrate 2, an anode 3, a cathode 4 and an emitting unit 10 provided between the anode 3 and the cathode 4. The emitting unit 10 comprises an emitting layer 5 preferably comprising a host material and a dopant. A hole injecting and transporting layer 6 or the like may be provided between the emitting layer 5 and the anode 3 and an electron-injecting layer 8 and an electron transporting layer 7 or the like (electron injecting and transporting unit 11) may be provided between the emitting layer 5 and the cathode 4. An electron-barrier layer may be provided on the anode 3 side of the emitting layer 5 and a hole-barrier layer may be provided on the cathode 4 side of the emitting layer 5. Due to such configuration, electrons or holes can be confined in the emitting layer 5, whereby possibility of generation of excitons in the emitting layer 5 can be improved.

ANODE (A)

The anode is an electrode which provides positive charge carriers. It may be composed, for example, of materials which comprise a metal, a mixture of different metals, a metal alloy, a metal oxide or a mixture of different metal oxides. Alternatively, the anode may be a conductive polymer. Suitable metals comprise the metals of groups 11, 4, 5 and 6 of the Periodic Table of the Elements, and also the transition metals of groups 8 to 10. When the anode is to be transparent, mixed metal oxides of groups 12, 13 and 14 of the Periodic Table of the Elements are generally used, for example indium tin oxide (ITO). It is likewise possible that the anode (a) comprises an organic material, for example polyaniline, as described, for example, in Nature, Vol. 357, pages 477 to 479 (Jun. 11, 1992). Preferred anode materials include conductive metal oxides, such as indium tin oxide (ITO) and indium zinc oxide (IZO), aluminum zinc oxide (AlZnO), and metals. Anode (and substrate) may be sufficiently transparent to create a bottom-emitting device. A preferred transparent substrate and anode combination is commercially available ITO (anode) deposited on glass or plastic (substrate). A reflective anode may be preferred for some top-emitting devices, to increase the amount of light emitted from the top of the device. At least either the anode or the cathode should be at least partly transparent in order to be able to emit the light formed. Other anode materials and structures may be used.

Hole Injection Layer (b) and Hole Transporting Layer (c):

The hole-transporting layer is an organic layer that is formed between the emitting layer and the anode, and has a function of transporting holes from the anode to the emitting layer. If the hole-transporting layer is composed of plural layers, an organic layer that is nearer to the anode may often be defined as the hole-injecting layer. The hole-injecting layer has a function of injecting holes efficiently to the organic layer unit from the anode.

Said hole injection layer is generally used for stabilizing hole injection from anode to hole transporting layer which is generally consist of organic materials.

Organic material having good contact with anode or organic material with p-type doping is preferably used for the hole injection layer.

Acceptor materials, or fused aromatic hydrocarbon materials or fused heterocycles which have high planarity, are preferably used, acceptor materials are more preferably used for the hole injection layer.

Specific examples for acceptor materials are, the quinone derivatives with one or more electron withdrawing groups, such as $F_4TCNQ$(2,3,5,6-tetrafluoro-7,7,8,8-tetracyanoquinodimethane), 1,2,3-Tris[(cyano)(4-cyano-2,3,5,6-tetrafluorophenyl)methylene]cyclopropane, and so on; hexa-azatriphenylene derivatives with one or more electron withdrawing groups, such as hexa-azatriphenylene-hexanitrile; aromatic hydrocarbon derivatives with one or more electron withdrawing groups; aryl boron derivatives with one or more electron withdrawing groups, and so on.

p-doping is usually consist of one or more p-dopant materials and one or more matrix materials. Matrix materials preferably have shallower HOMO level and p-dopant preferably have deeper LUMO level to enhance the carrier density of the layer. Aryl or heteroaryl amine derivatives are preferably used as the matrix materials. Specific examples for the matrix material are the same as that for hole transporting layer which is explained at the later part. Specific examples for p-dopant are the above mentioned acceptor materials, preferably the quinone derivatives with one or more electron withdrawing groups, such as $F_4TCNQ$, 1,2,3-Tris[(cyano)(4-cyano-2,3,5,6-tetrafluorophenyl)methylene]cyclopropane.

The ratio of the p-type dopant is preferably less than 20% of molar ratio, more preferably less than 10%, such as 1%, 3%, 5% and so on.

Hole transporting layer is generally used for injecting and transporting holes efficiently, and aromatic or heterocyclic amine derivatives are preferably used.

Specific examples for hole transporting layer are represented as general formula (H),

(H)

$Ar_1$~$Ar_3$ each independently represents substituted or unsubstituted aryl group having 5 to 50 carbon atoms or substituted or unsubstituted heterocyclic group having 5 to 50 cyclic atoms, preferably phenyl group, biphenyl group, terphenyl group, naphthyl group, phenanthryl group, triphenylenyl group, fluorenyl group, spirobifluorenyl group, indenofluorenyl group, carbazolyl group, dibenzofuranyl group, dibenzothiophenyl group, carbazole substituted aryl group, dibenzofuran substituted aryl group or dibenzothiophene substituted aryl group; two or more substituents selected among $Ar^1 \sim Ar^3$ may be bonded to each other to form a ring structure, such as carbazole ring structure, acridane ring structure and so on.

According to one embodiment, it is preferable that at least one of $Ar_1 \sim Ar_3$ have additional one aryl or heterocyclic amine substituent, more preferably Ar1 have an additional aryl amino substituent, at the case of that it is preferable that Ar1 represents substituted or unsubstituted biphenylene group, substituted or unsubstituted fluorenylene group.

Second hole transporting layer is usually inserted between the first hole transporting layer and the emitting layer to enhance device performance by blocking excess electrons or excitons. Specific examples for second hole transporting layer is the same as the first hole transporting layer. It is preferably that second hole transporting layer have higher triplet energy to block triplet exciton especially for phosphorescent green device, such as bicarbazole derivatives, biphenylamine derivatives, triphenylenyl amine derivatives, fluorenyl amine derivatives, carbazole substituted arylamine derivatives, dibenzofuran substituted arylamine derivatives, dibenzothiophene substituted arylamine derivatives, and so on.

Exciton Blocking Layer (d):

Blocking layers may be used to reduce the number of charge carriers (electrons or holes) and/or excitons that leave the emissive layer. An electron/exciton blocking layer (d) may be disposed between the first emitting layer (e) and the hole transport layer (c), to block electrons from emitting layer (e) in the direction of hole transport layer (c). Blocking layers may also be used to block excitons from diffusing out of the emissive layer.

Suitable metal complexes for use as electron/exciton blocker material are, for example, carbene complexes as described in WO2005/019373A2, WO2006/056418A2, WO2005/113704, WO2007/115970, WO2007/115981, WO2008/000727 and PCT/EP2014/055520. Explicit reference is made here to the disclosure of the WO applications cited, and these disclosures shall be considered to be incorporated into the content of the present application.

According to a preferred embodiment of the present invention, at least one compound of general formula (Ia) or (Ib) is present in the exciton blocking layer of the OLED according to the present invention.

Emitting Layer (e)

The light emitting layer is an organic layer having a light emitting function and is formed from one or more layers, wherein one of the layers comprises a host material (first host material), optionally a second host material, and the light emitting material.

According to a preferred embodiment of the present invention, at least one compound of general formula (Ia) or (Ib) is present in the emitting layer of the OLED according to the present invention, preferably as host material.

When the light emitting layer is composed of two or more layers, the light emitting layer or layers other than that mentioned above contains or contain a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

The light emitting layer may be made into a double dopant layer, in which two or more kinds of dopant materials having high quantum yield are used in combination and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The light emitting layer may be different in the hole injection ability and the electron injection ability, and also in the hole transporting ability and the electron transporting ability each being expressed by mobility.

The light emitting layer is formed, for example, by a known method, such as a vapor deposition method, a spin coating method, and LB method. Alternatively, the light emitting layer may be formed by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The light-emitting layer (e) comprises at least one fluorescence or phosphorescence emitter, suitable emitter materials being known to those skilled in the art.

The emission wavelength of the phosphorescent dopant used in the light emitting layer is not particularly limited. In a preferred embodiment, at least one of the phosphorescent dopants used in the light emitting layer has the peak of emission wavelength of in general 430 nm or longer and 780 nm or shorter, preferably 490 nm or longer and 700 nm or shorter and more preferably 490 nm or longer and 650 nm or shorter. Most preferred are green emitter materials (490 to 570 nm). In another preferred embodiment, red emitter materials (570 to 680 nm) are preferred.

The phosphorescent dopant (phosphorescent emitter material) is a compound which usually emits light by releasing the energy of excited triplet state.

The compounds according to general formula (Ia) or (Ib) are most preferably used as the matrix (=host material) in the light-emitting layer.

Suitable metal complexes for use in the inventive OLEDs, preferably as emitter material, are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669, WO10086089, US2011/0057559, WO2011/106344, US2011/0233528, WO2012/048266 and WO2012/172482.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)pyridinato-N,C$^{3'}$)(acetylacetonate), tris(2-phenylquinoline)iridium(III), iridium(III) bis(2-(4,6-difluorophenyl)pyridinato-N,C$^{2}$)picolinate, iridium(III) bis(1-phenylisoquinoline)(acetylacetonate), bis(2-phenylquinoline)(acetylacetonato)iridium(III), iridium(III) bis(di-benzo[f,h]quinoxaline)(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetyl-acetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-yl-pyridine)(acetylacetonato)iridium(III).

In addition, the following commercially available materials are suitable: tris(dibenzoylacetonato)mono(phenanthroline)europium(III), tris(dibenzoylmethane)-mono(phenanthroline)europium(III), tris(dibenzoylmethane)mono(5-aminophenanthroline)-europium(Ill), tris(di-2-naphthoylmethane)mono(phenanthroline)europium(III), tris(4-bromobenzoylmethane)mono(phenanthroline)europium(III), tris(di(biphenyl)methane)-mono(phenanthroline)europium (III), tris(dibenzoylmethane)mono(4,7-diphenyl-phenanthroline)europium(III), tris(dibenzoylmethane)mono(4,7-dimethyl-phenanthroline)europium(III), tris(dibenzoylmethane)mono(4,7-dimethylphenanthrolinedisulfonic acid)europium(Ill) disodium salt, tris[di(4-(2-(2-ethoxyethoxy)ethoxy)benzoylmethane)]mono-(phenanthroline)europium (III) and tris[di[4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato)diphenylmethylphosphine, osmium(II) bis(3-(trifluoromethyl)-5-(2-pyridyl)-1,2,4-triazole)dimethylphenylphosphine, osmium(II) bis(3-(trifluoromethyl)-5-(4-tert-butylpyridyl)-1,2,4-triazolato)dimethylphenylphosphine, osmium(II) bis(3-(trifluoromethyl)-5-(2-pyridyl)-pyrazolato)dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Particularly suitable metal complexes are described in US2014048784, US2012223295, US2014367667, US2013234119, US2014001446, US2014231794, US2014008633, WO2012108388 and WO2012108389. The emitters mentioned in US2013234119, paragraph [0222], are exemplified. Selected emitters, especially red emitters, of said emitters mentioned in US2013234119 paragraph [0222], are:

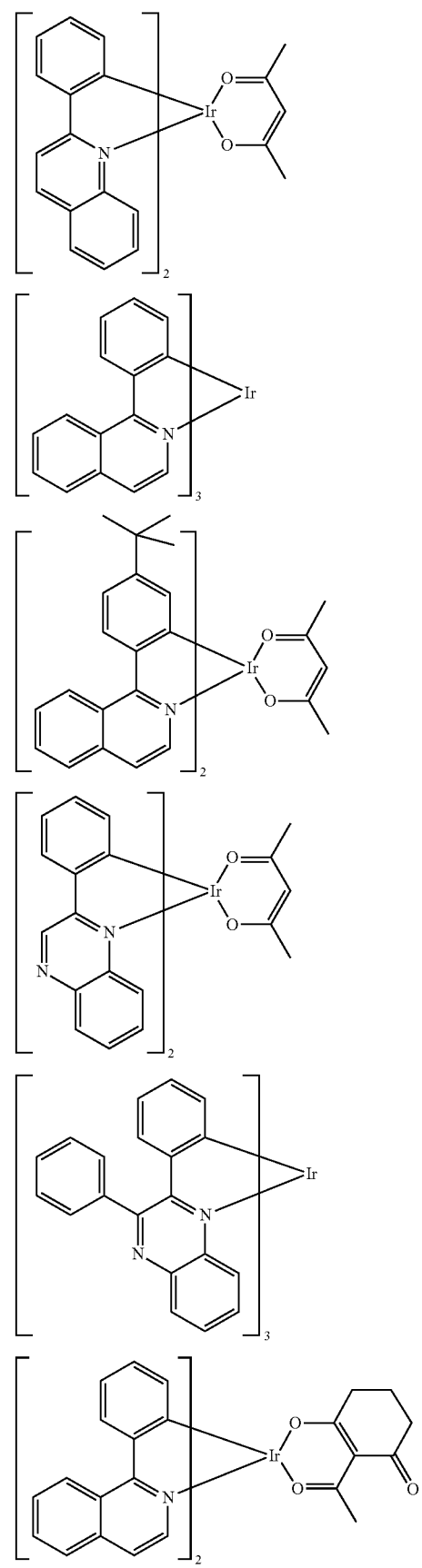

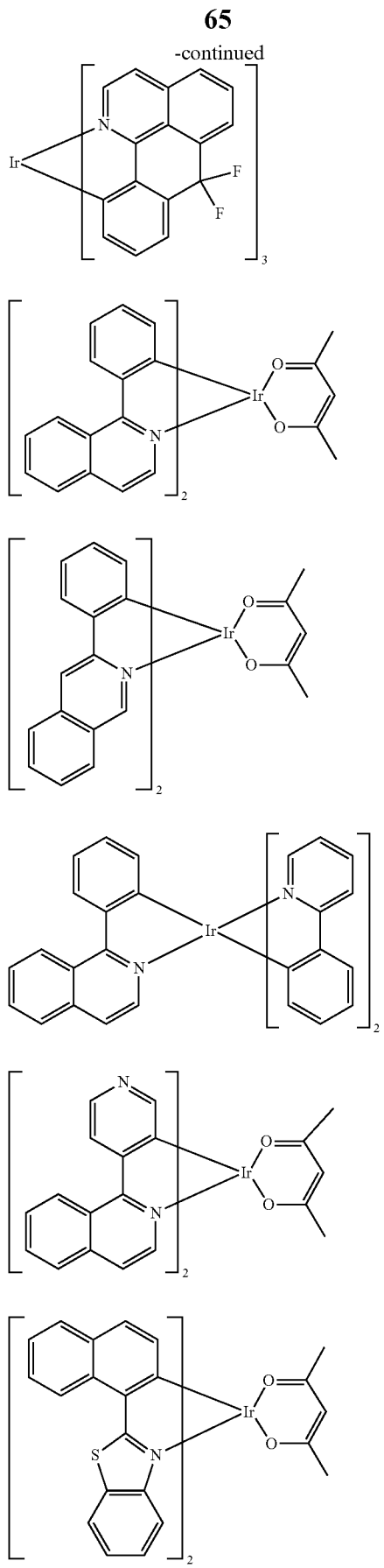
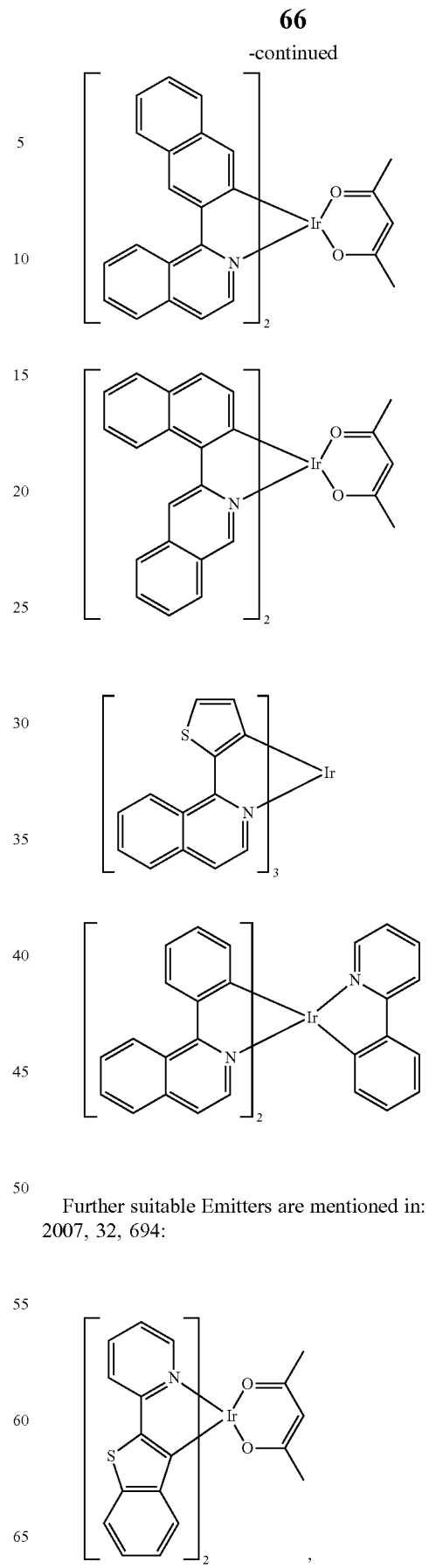
Further suitable Emitters are mentioned in: Mrs Bulletin, 2007, 32, 694:

-continued
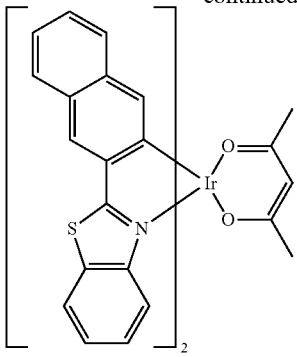
Further suitable Emitters are mentioned in: WO2009100991:
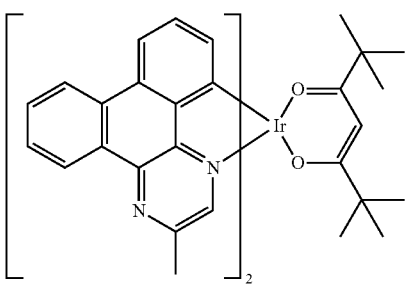
Further suitable Emitters are mentioned in: WO2008101842:
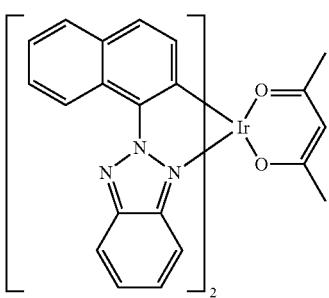
Further suitable Emitters are mentioned in: US 20140048784, especially in paragraph [0159]:
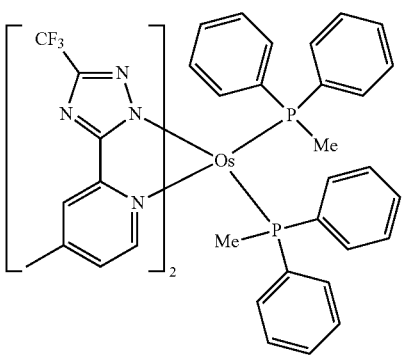
-continued
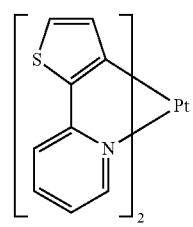
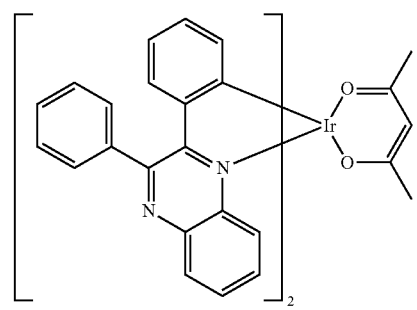
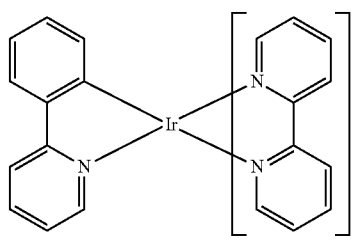
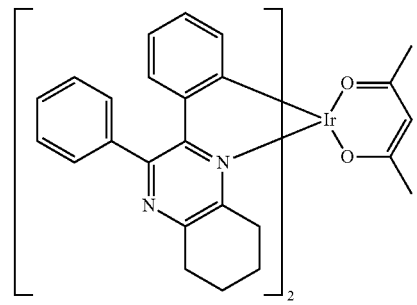
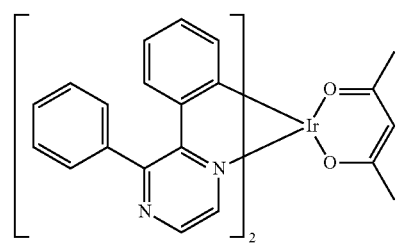
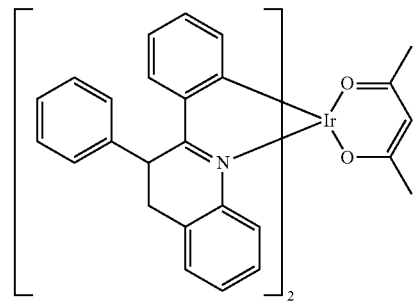

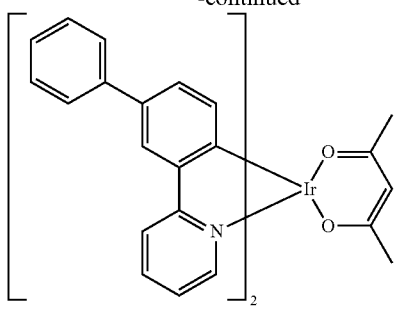
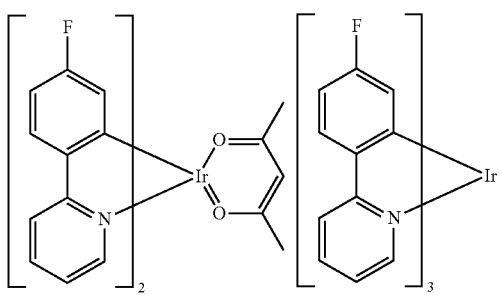
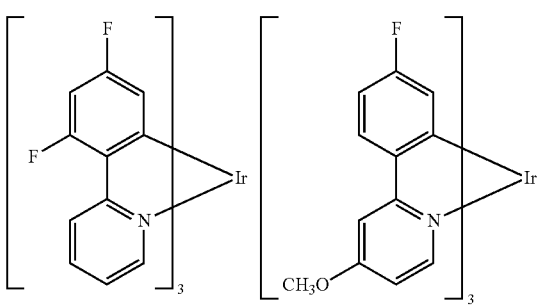
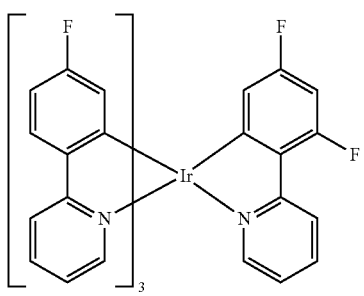
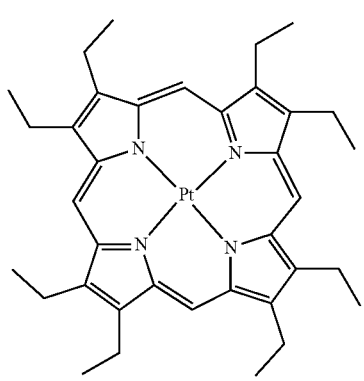
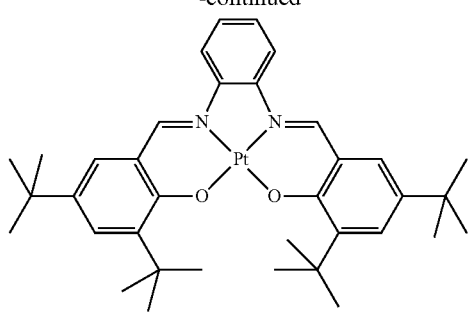
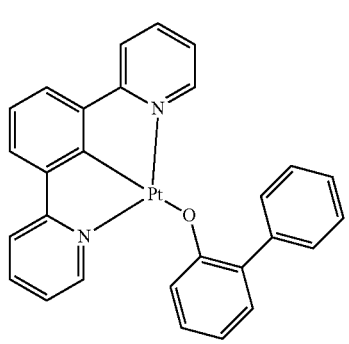
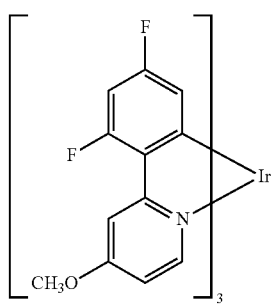
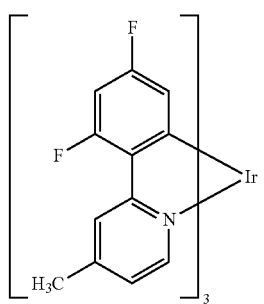
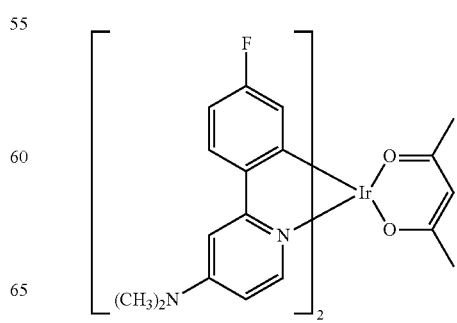

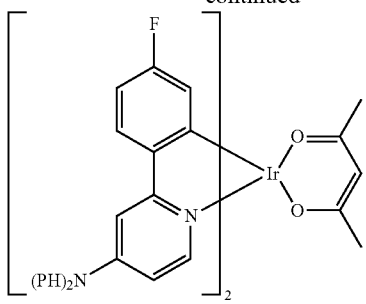
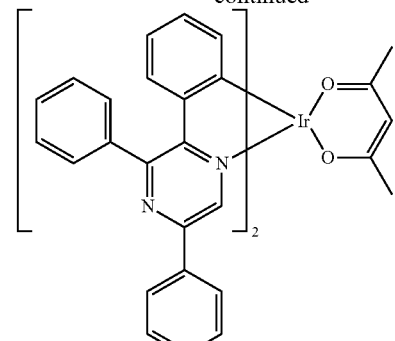
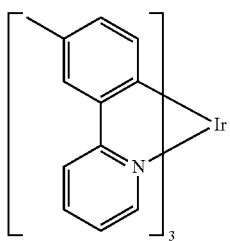
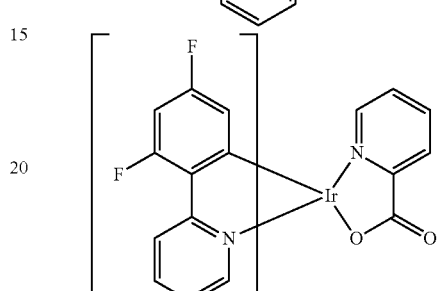
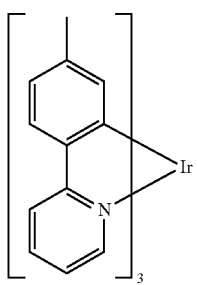
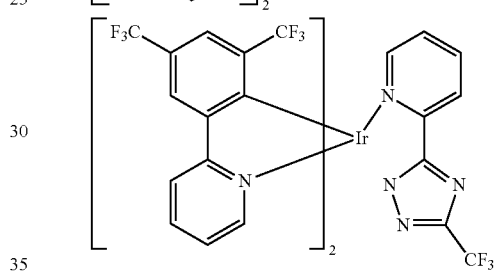
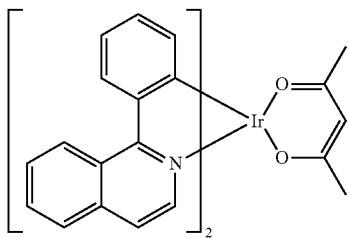
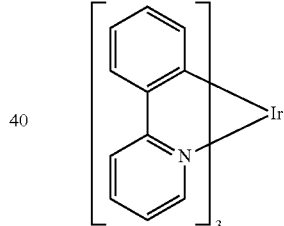
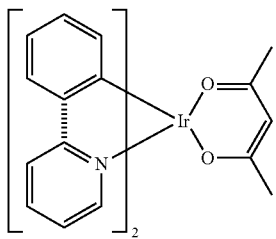
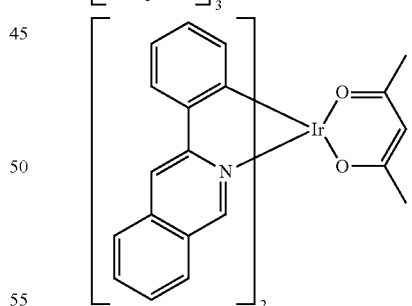
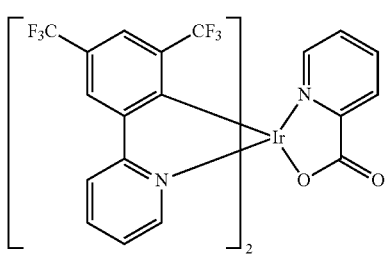
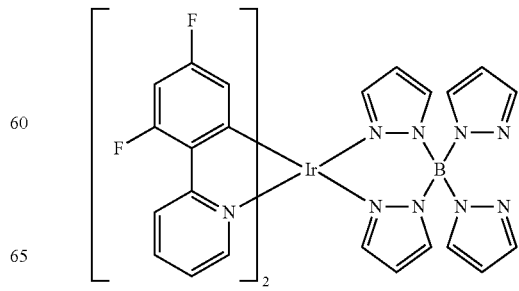

-continued
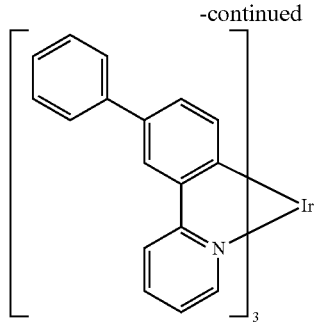
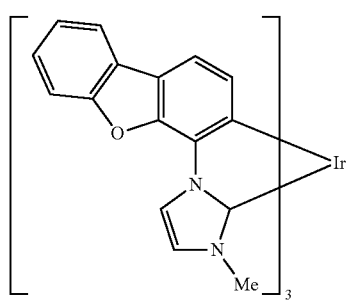
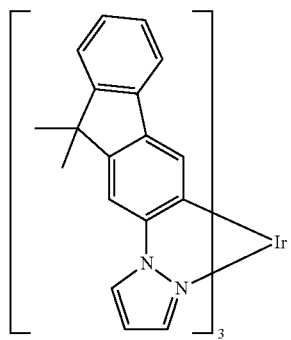
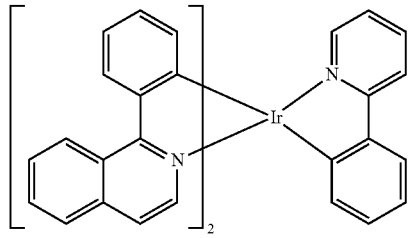
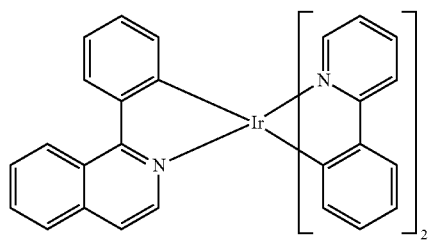
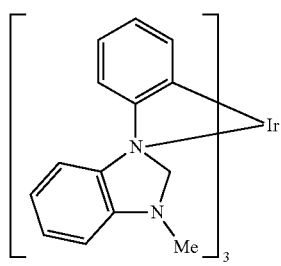
-continued
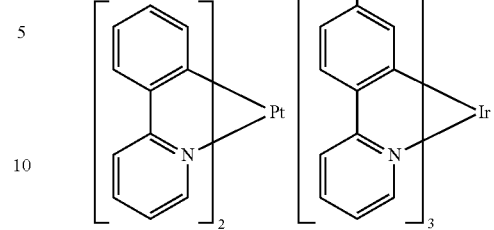
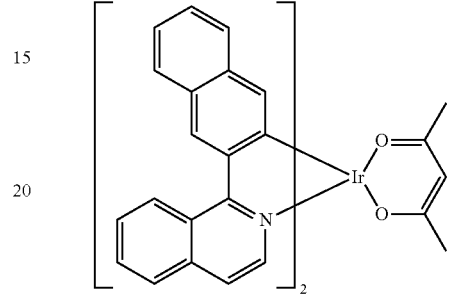
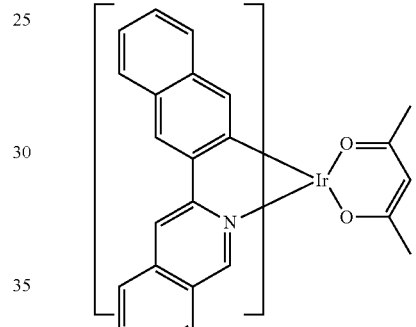
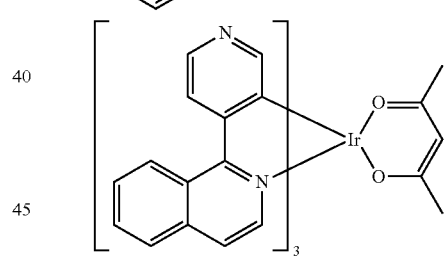
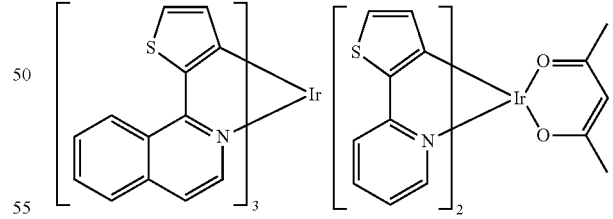
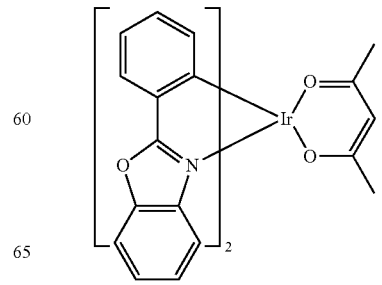

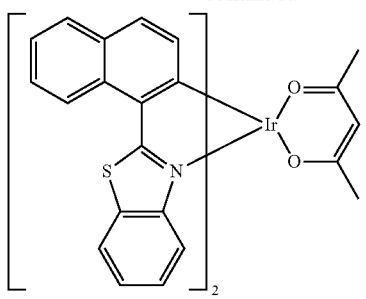
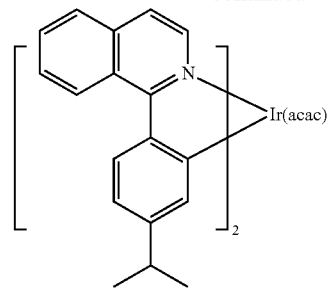
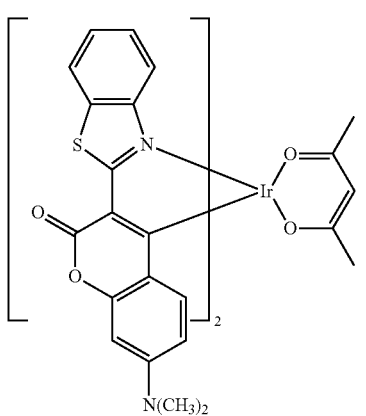
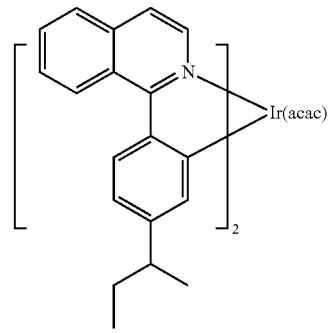
Further suitable red emitters are shown in WO 2008/109824. Preferred red emitters according to this document are the following compounds:
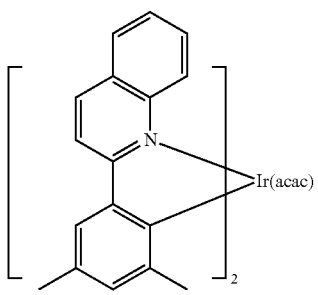
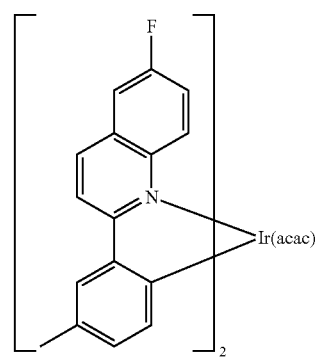
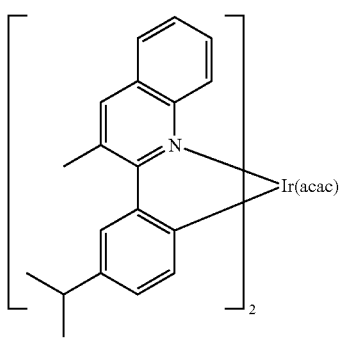
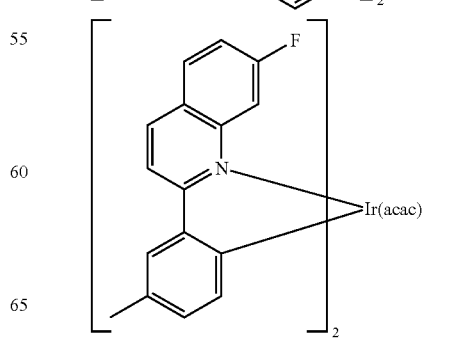

-continued
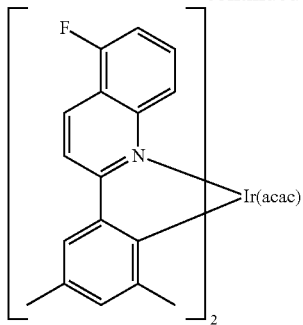
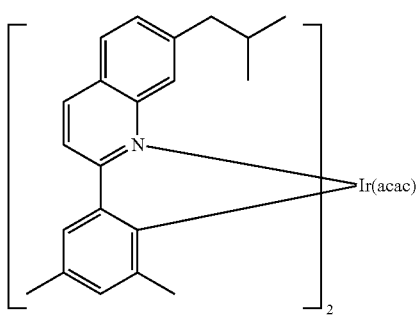
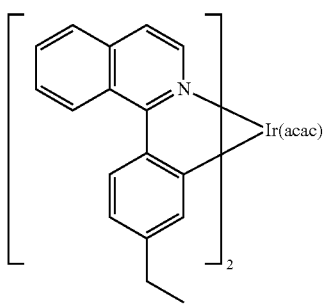
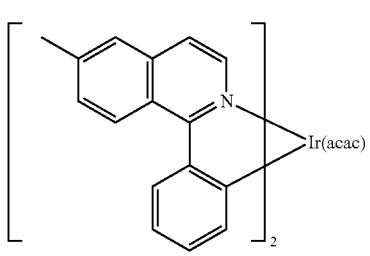
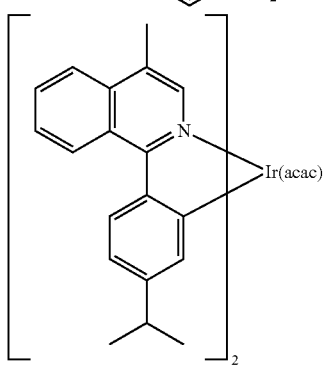
-continued
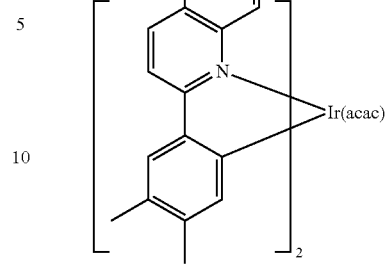
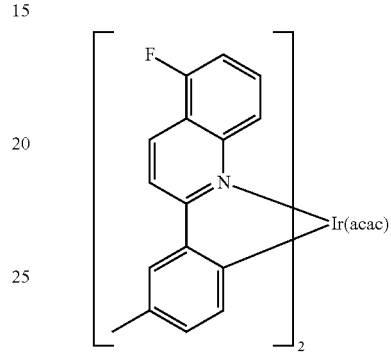
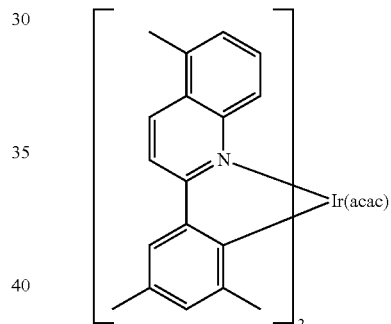
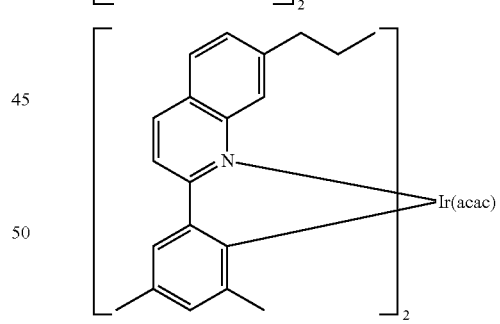
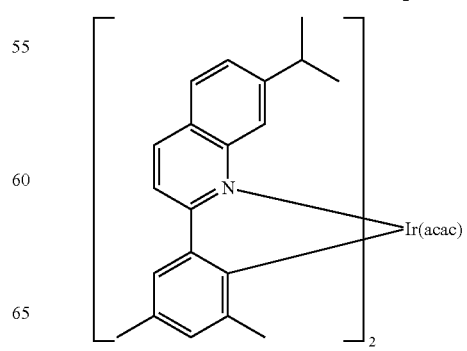

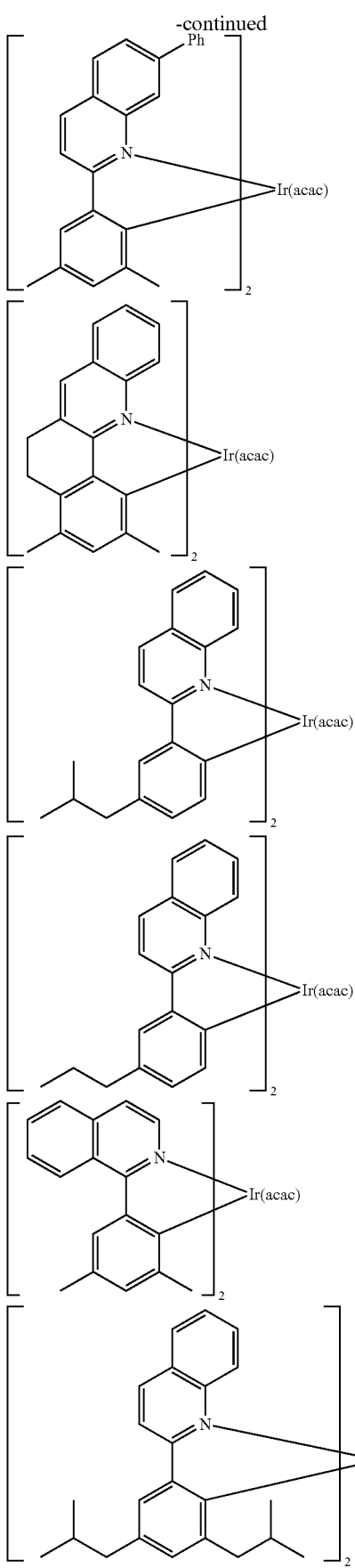
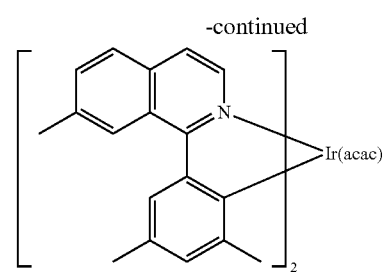
The emitter materials (dopants), preferably the phosphorescent emitter materials, may be used alone or in combination of two or more.
Further red emitters that may be used in the OLEDs according to the present invention are disclosed in US 2013/0299795 and are shown in the following:

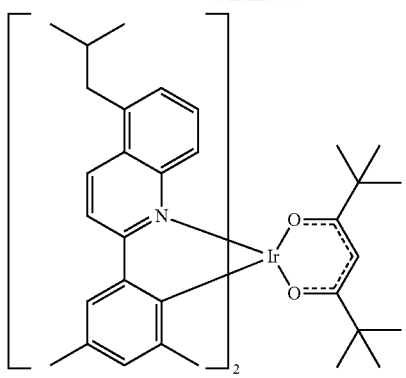
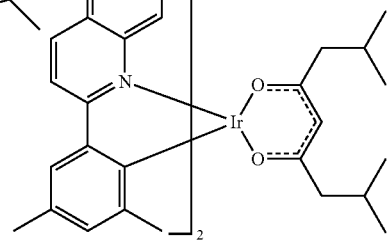
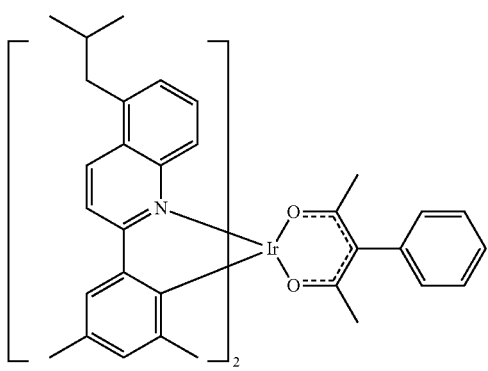
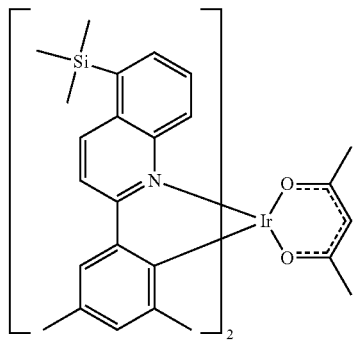
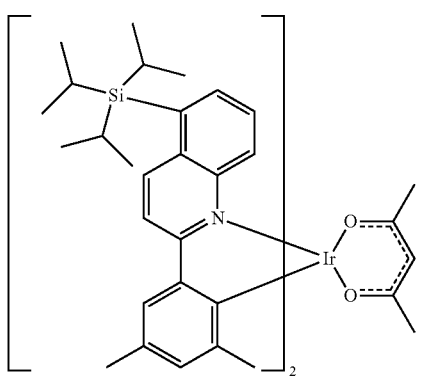
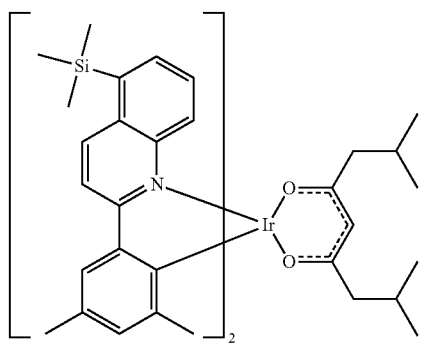
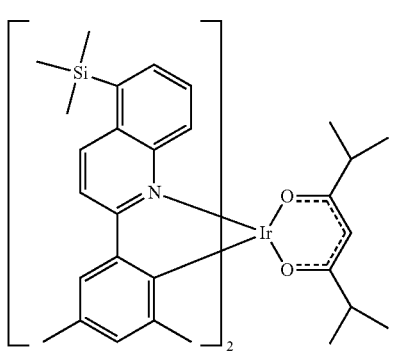
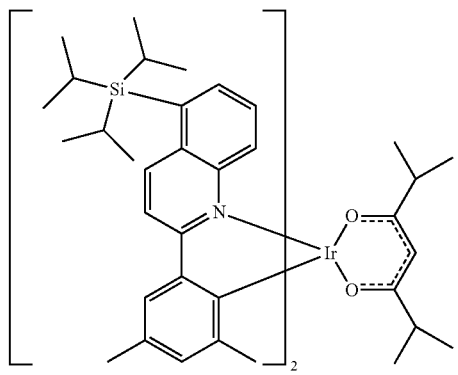

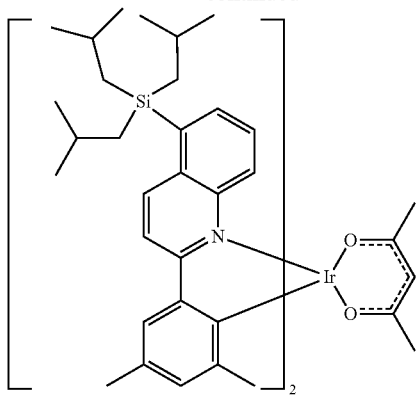
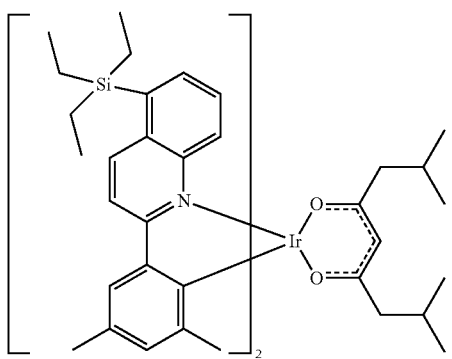
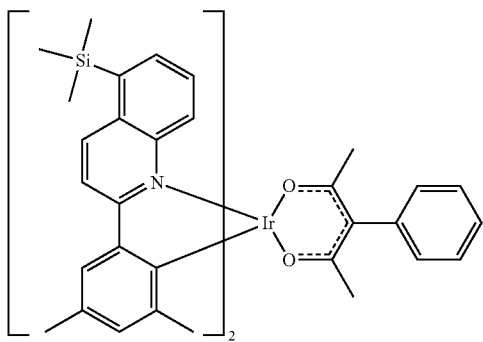
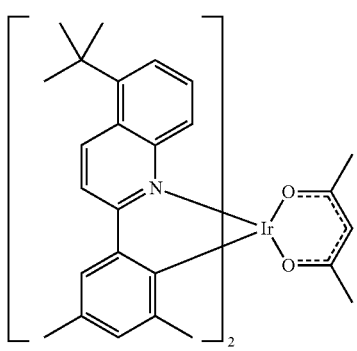
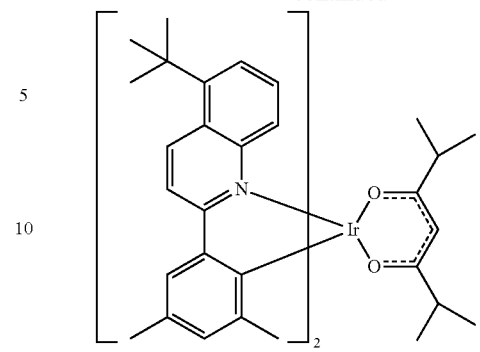
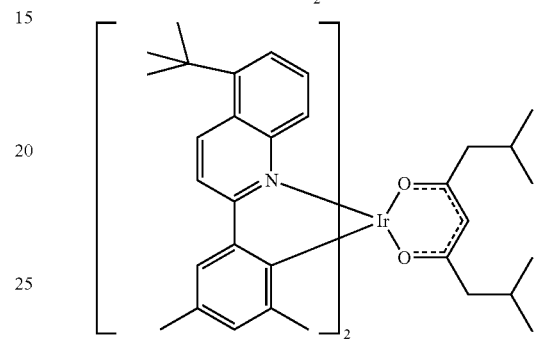
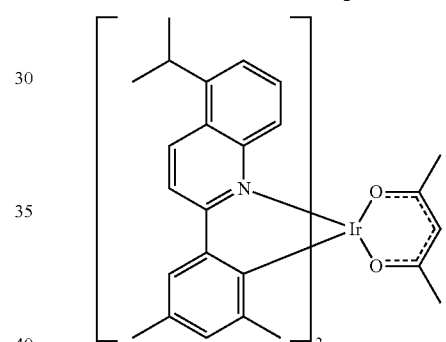
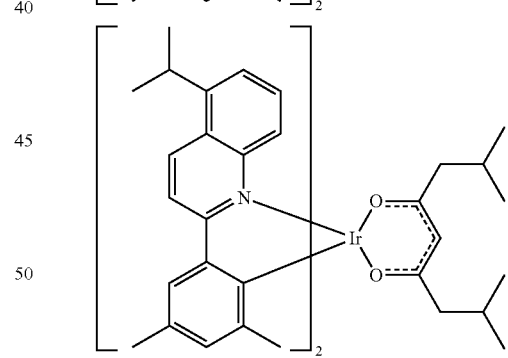
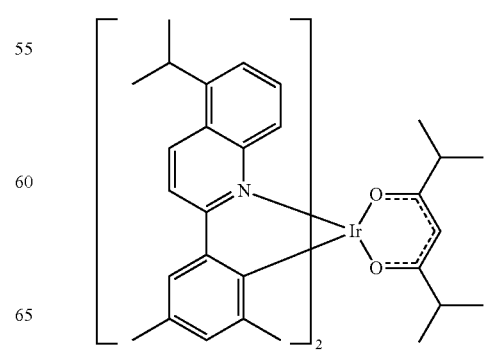

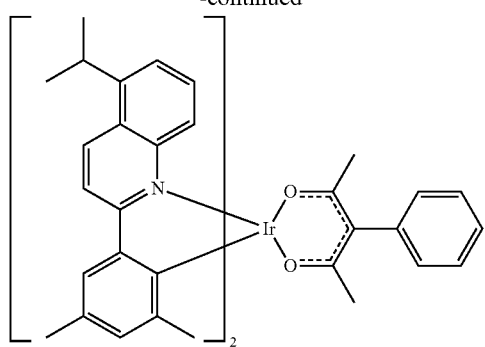
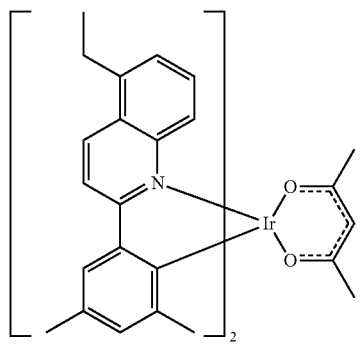
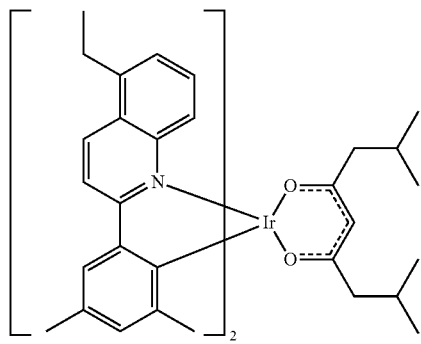
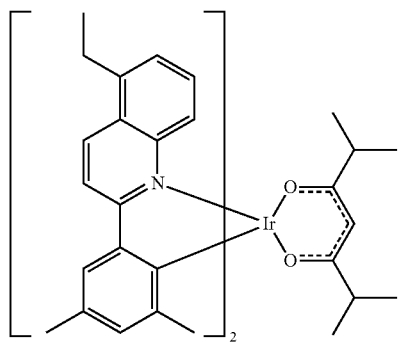
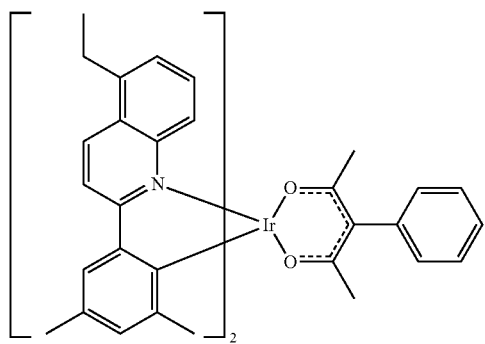
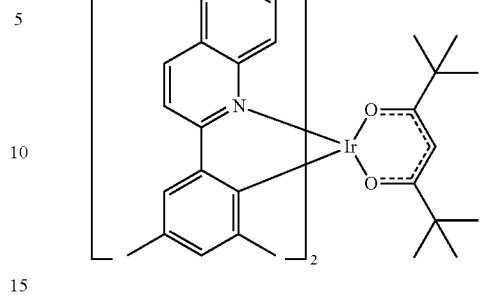
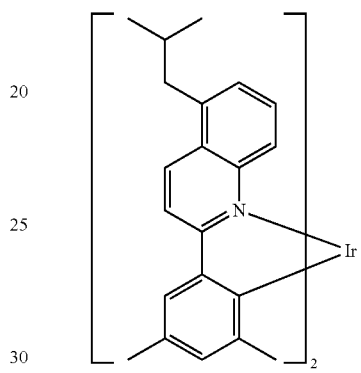
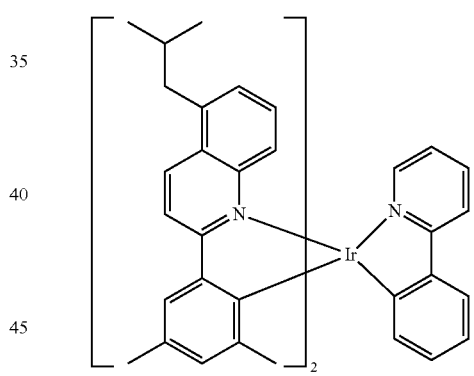
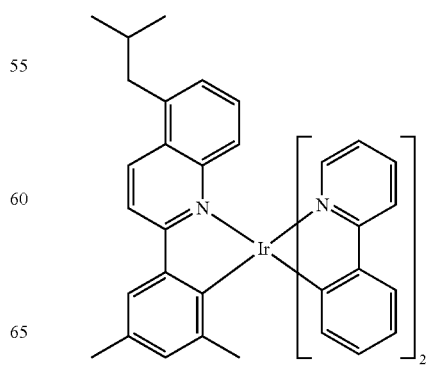

87 -continued
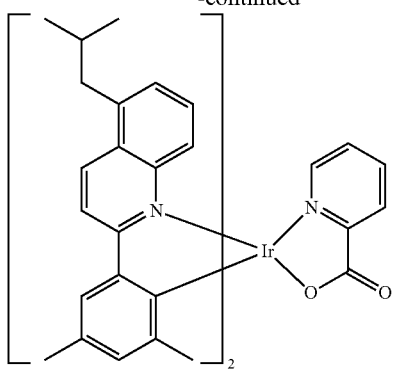
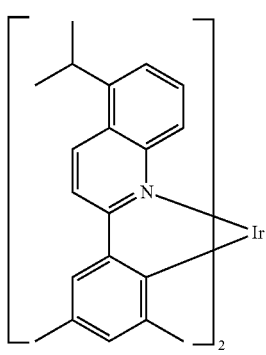
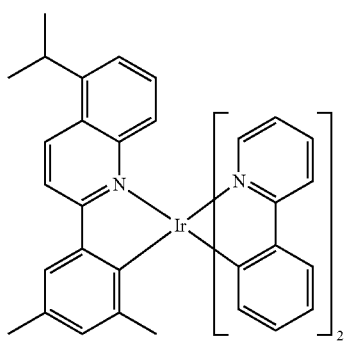
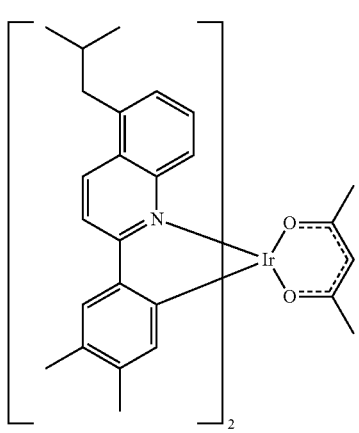
88 -continued
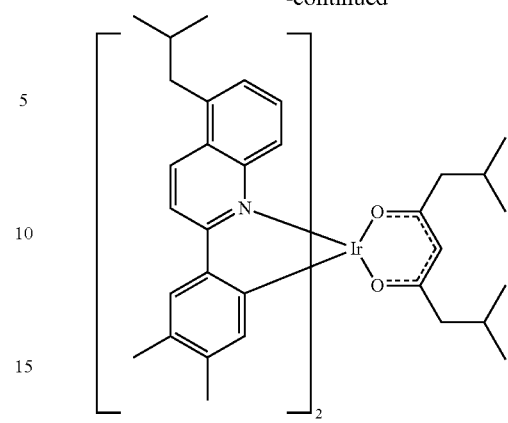
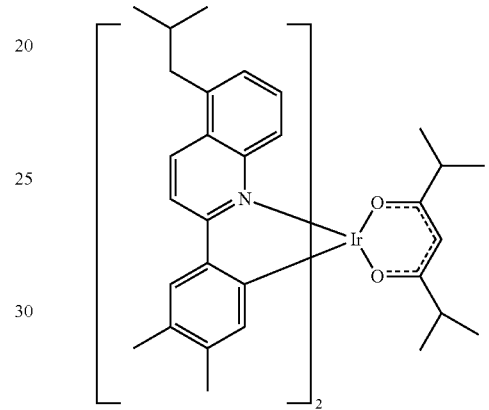
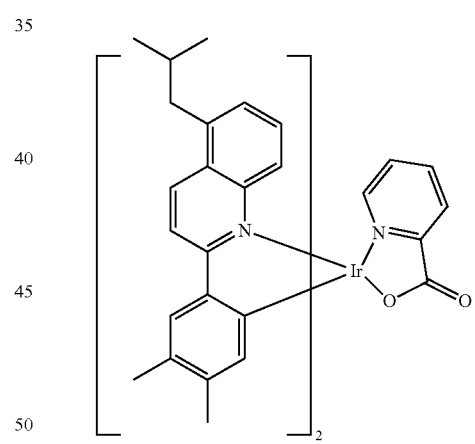
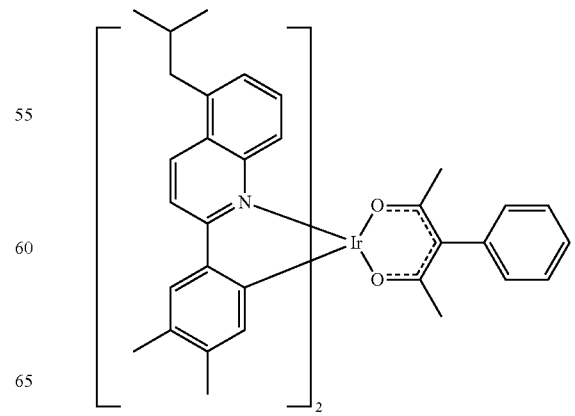

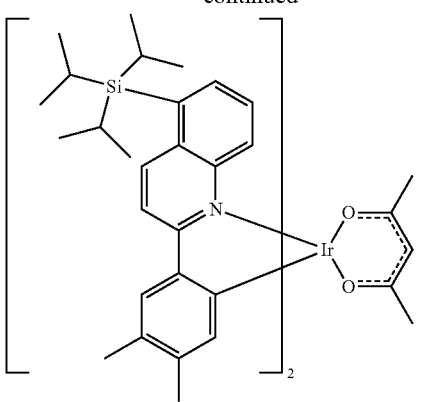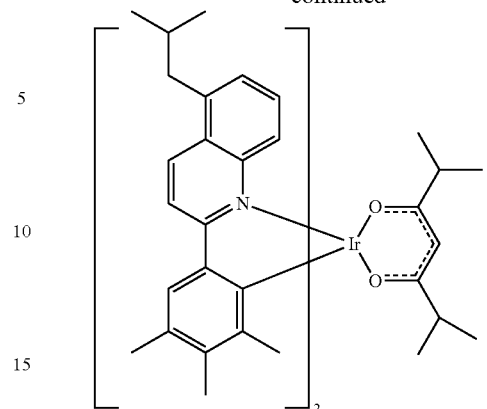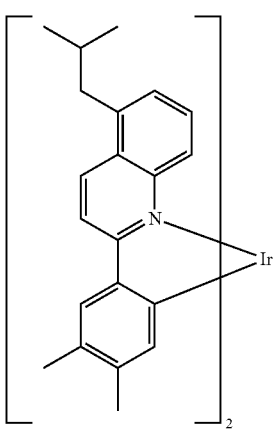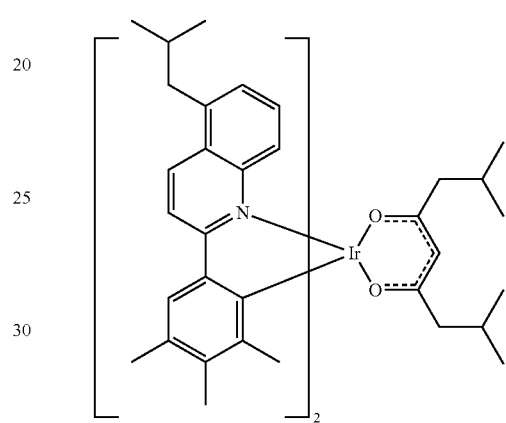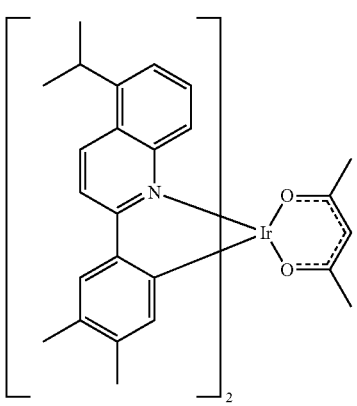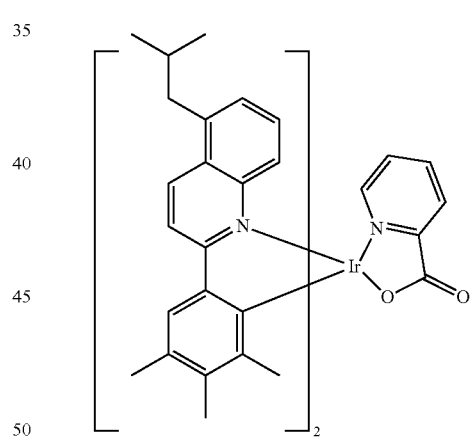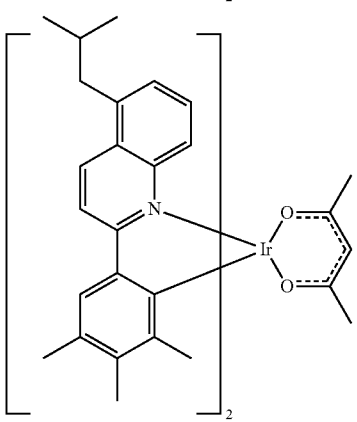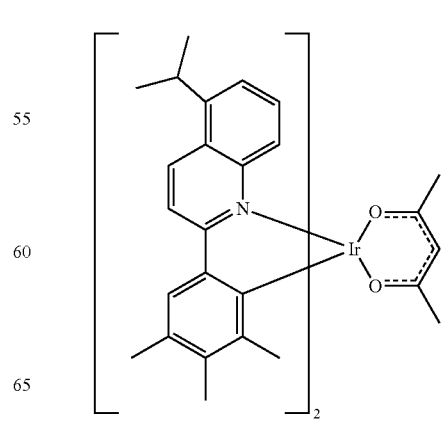

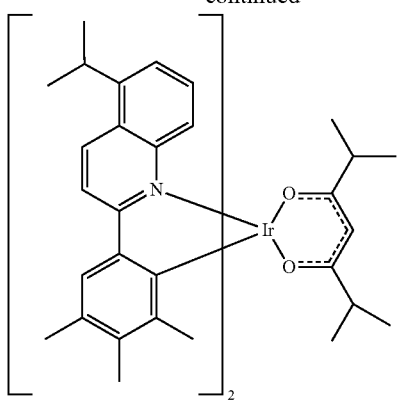
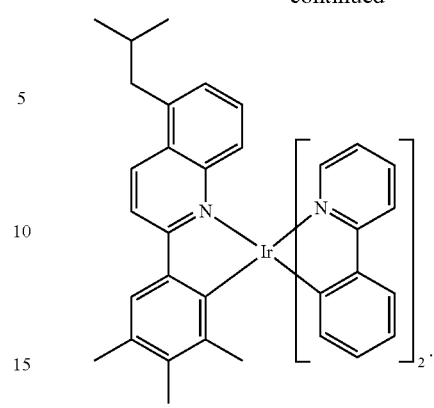
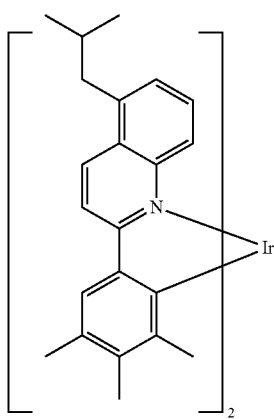
Further red emitters that may be used in the OLEDs according to the present invention are disclosed in US 2013/0146848 and are shown in the following:
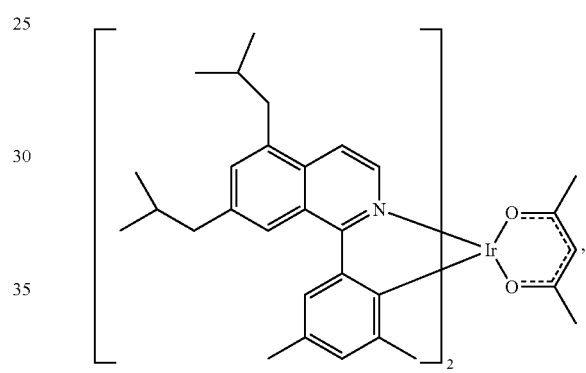
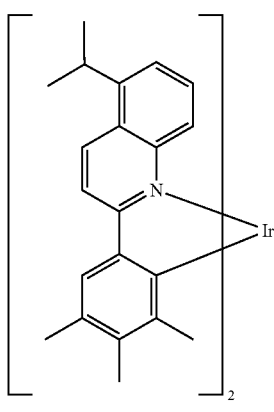
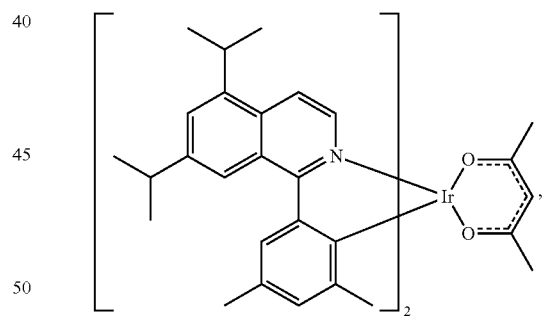
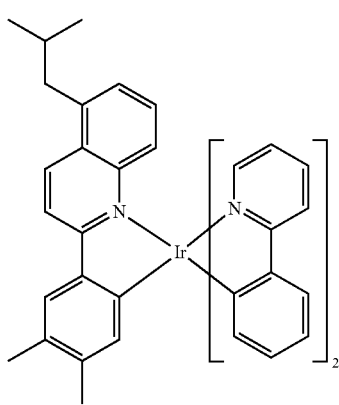
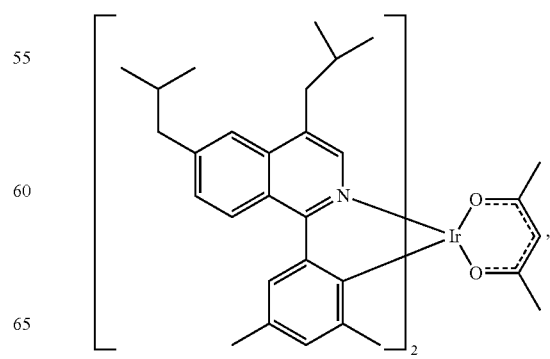

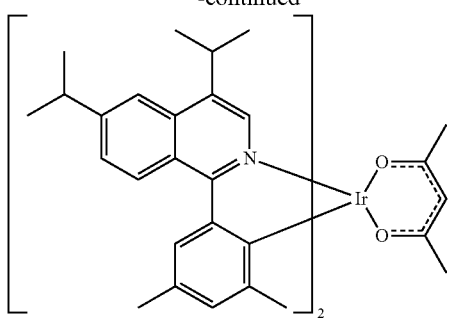
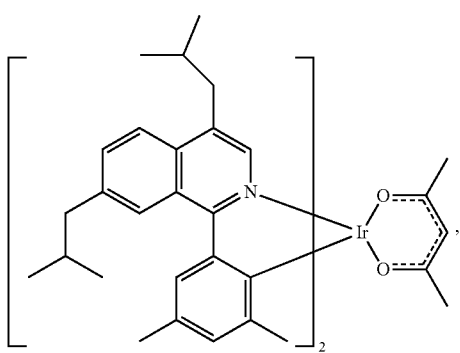
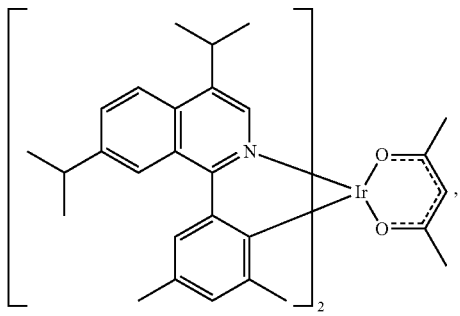
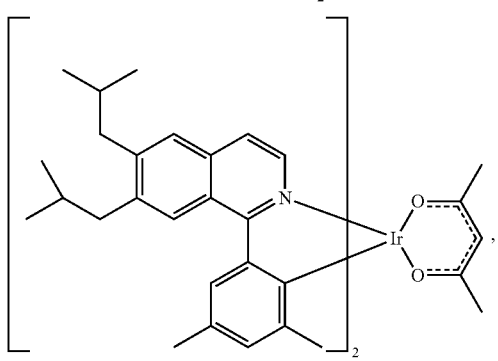
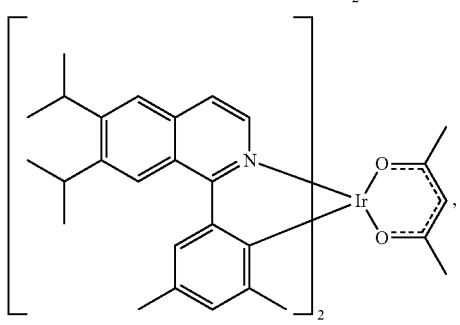
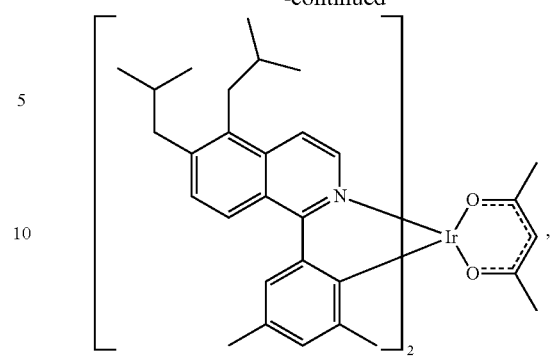
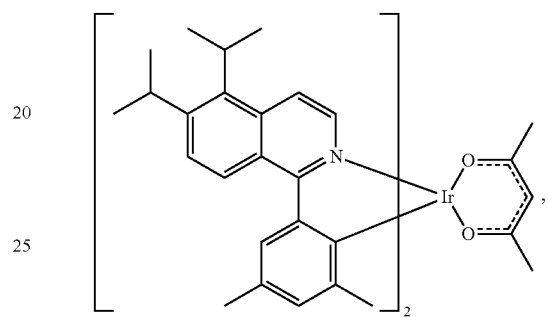
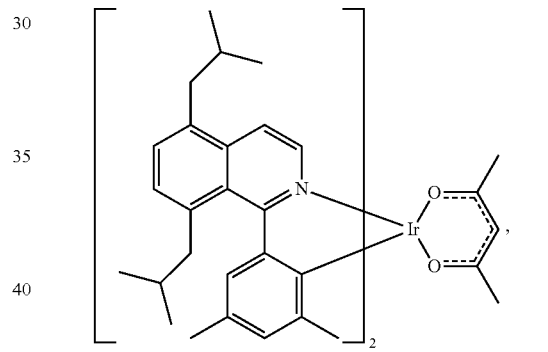
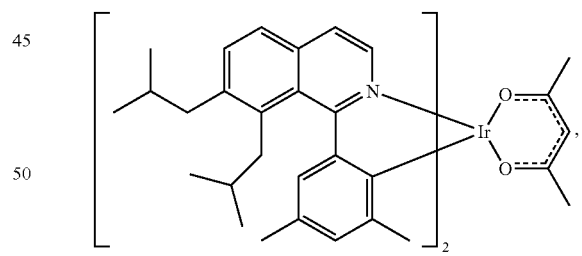
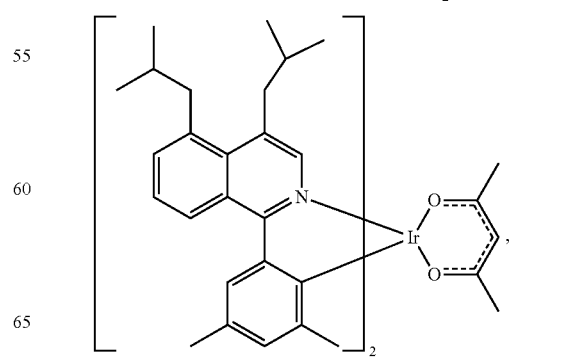

-continued
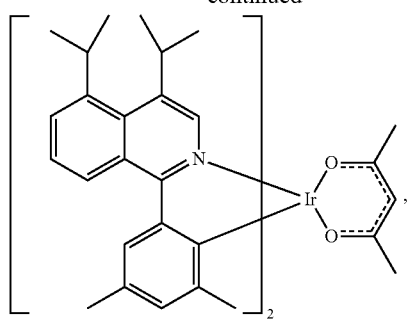
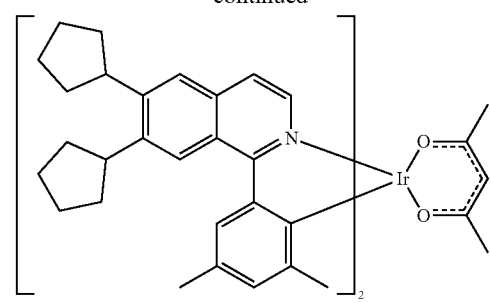
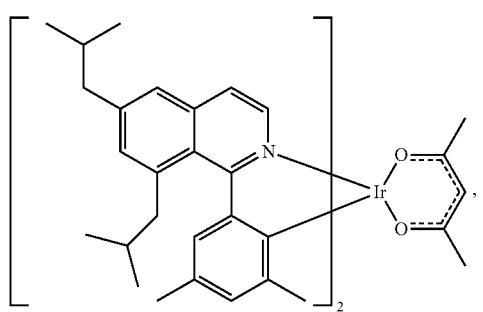
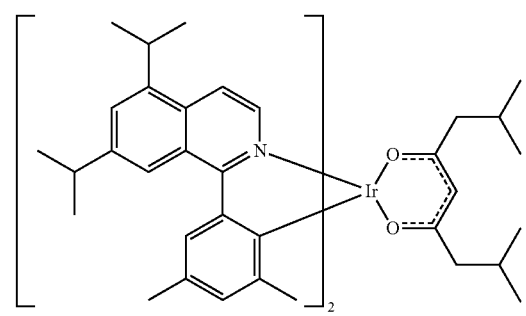
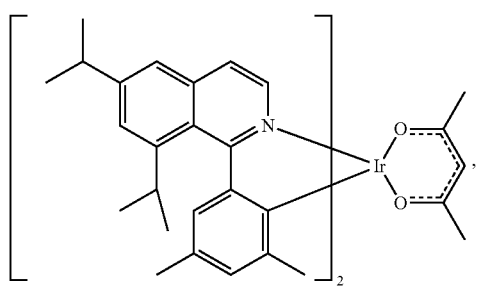
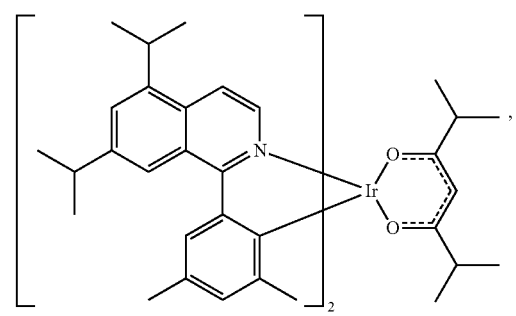
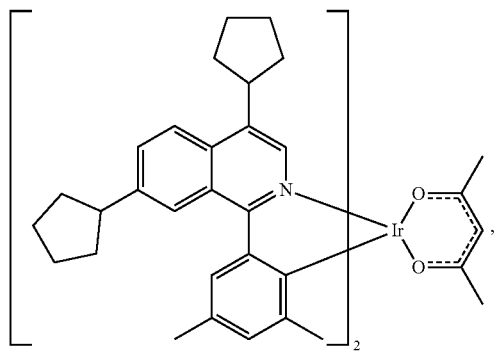
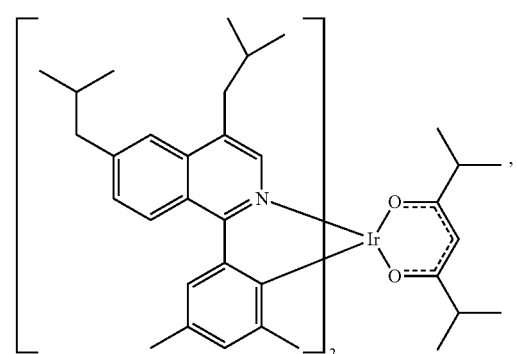
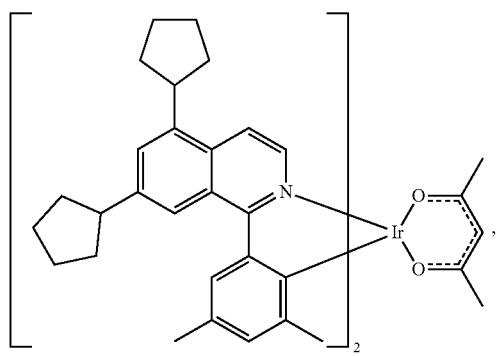
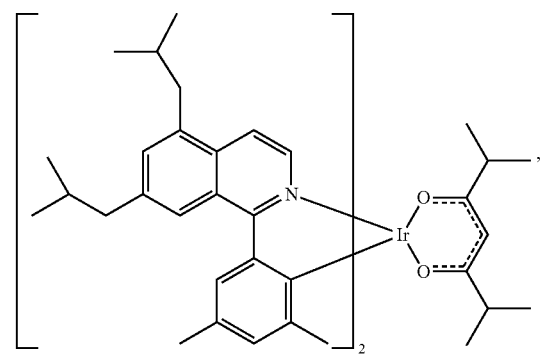

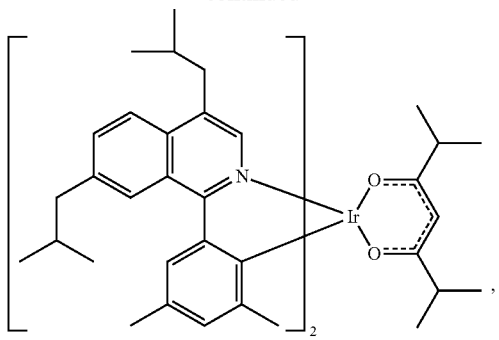
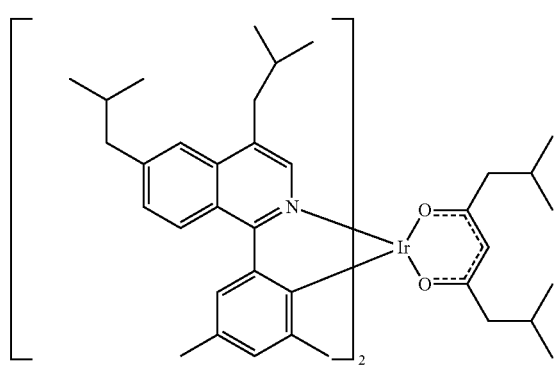
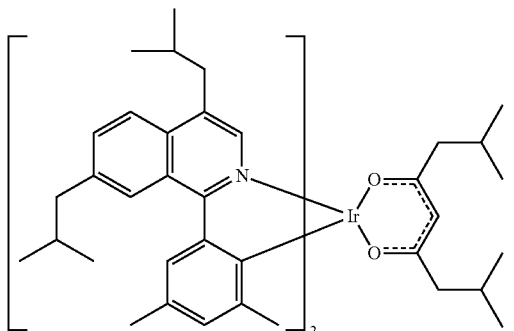
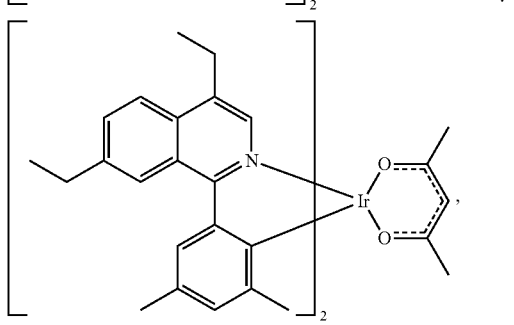
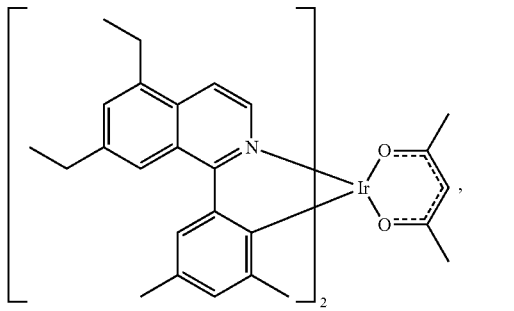
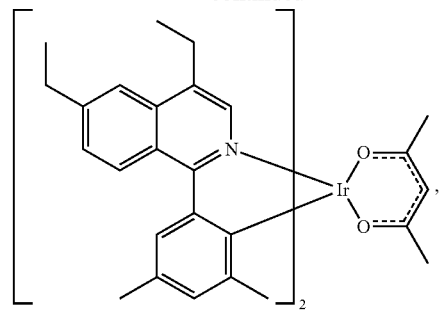
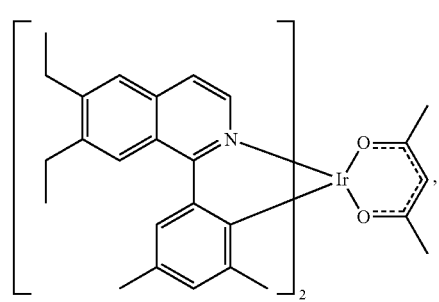
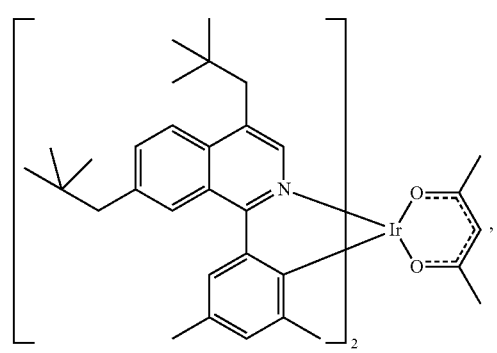
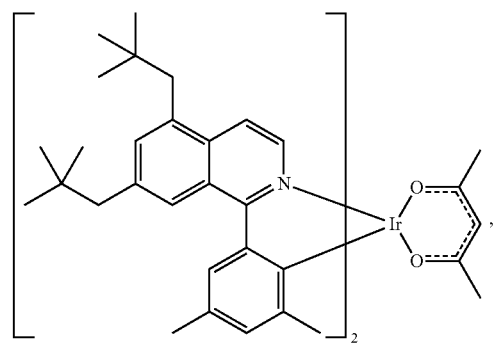
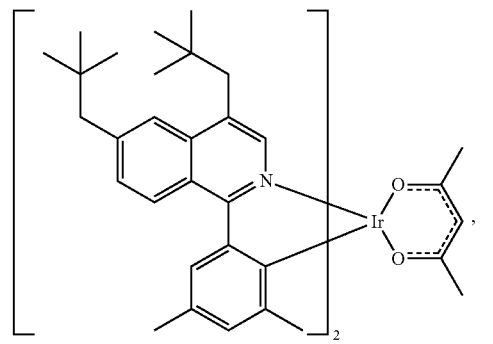

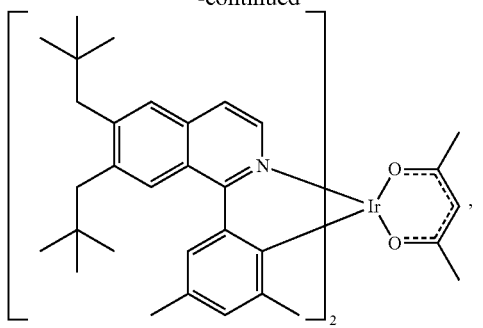
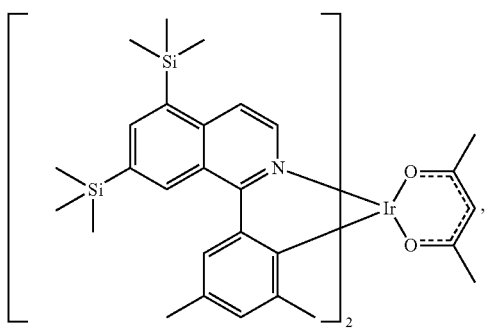
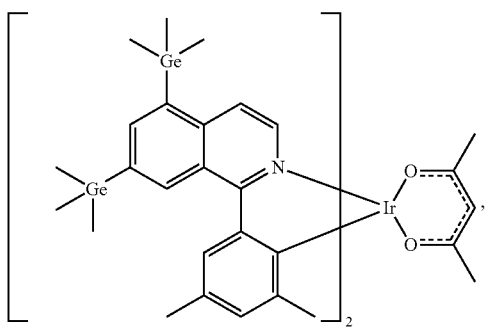
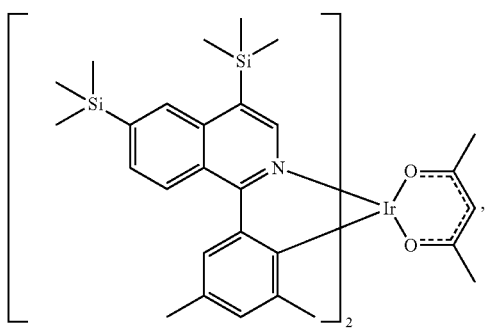
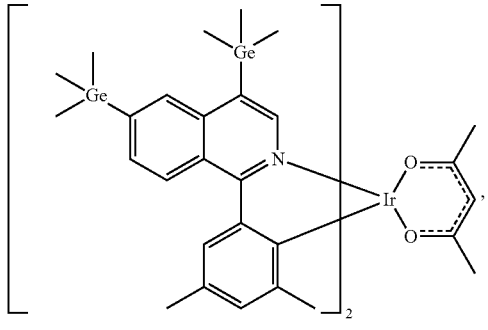
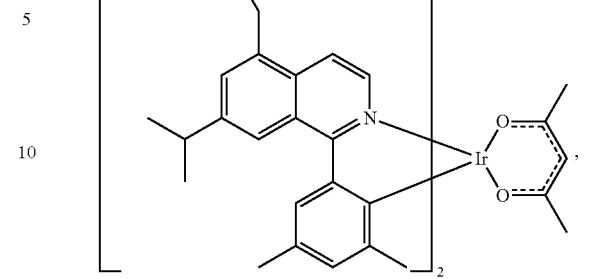
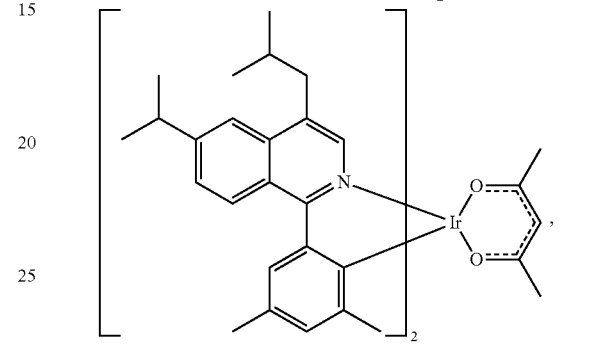
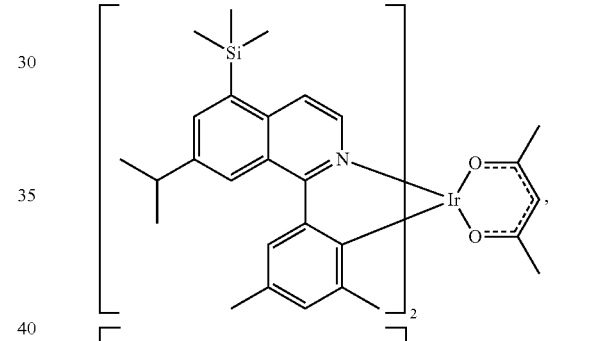
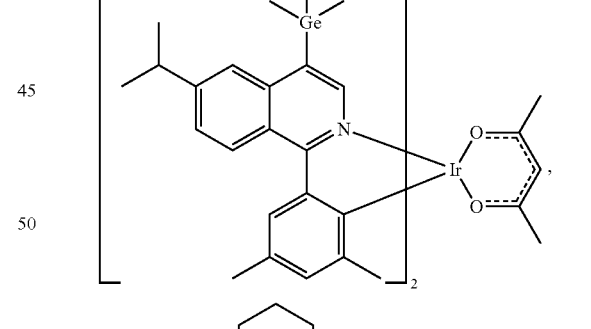
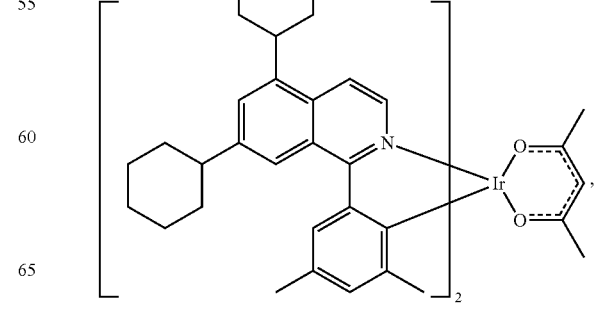

101
-continued
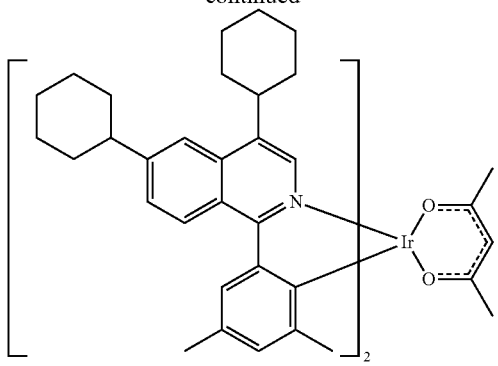
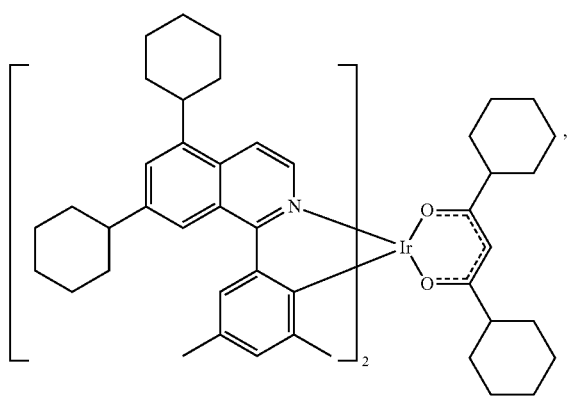
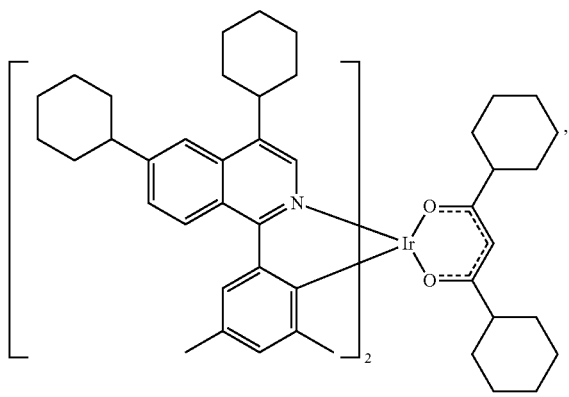
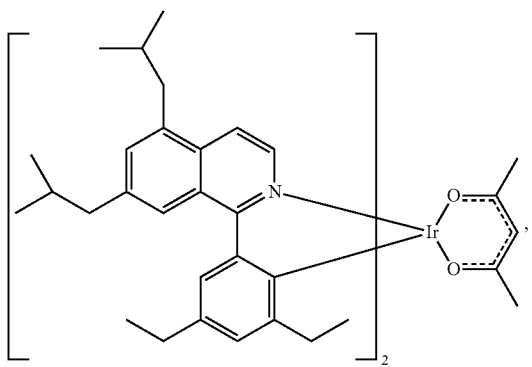
102
-continued
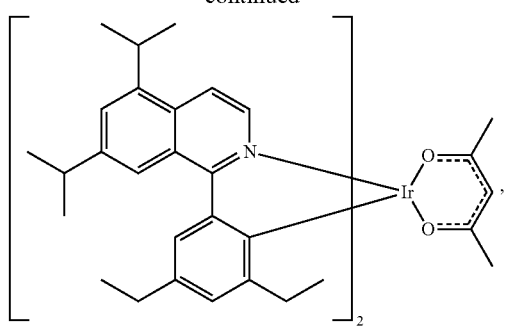
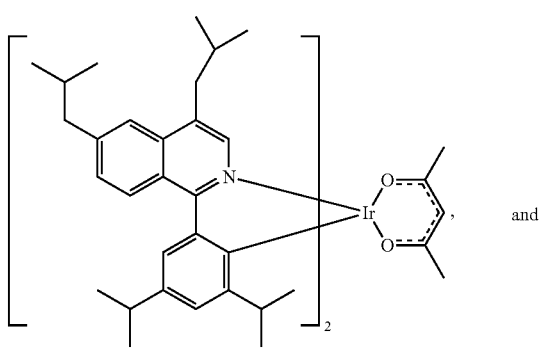
,
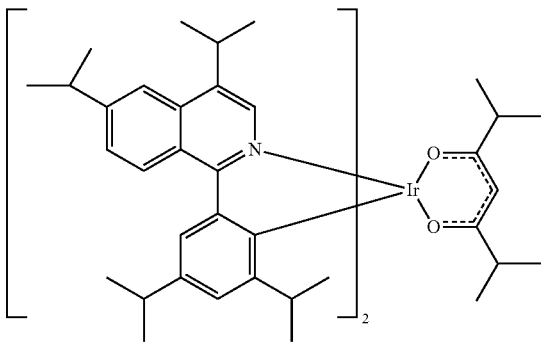
, and
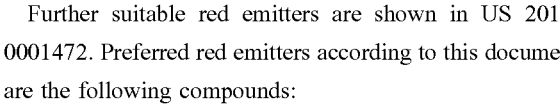
Further suitable red emitters are shown in US 2015/0001472. Preferred red emitters according to this document are the following compounds:
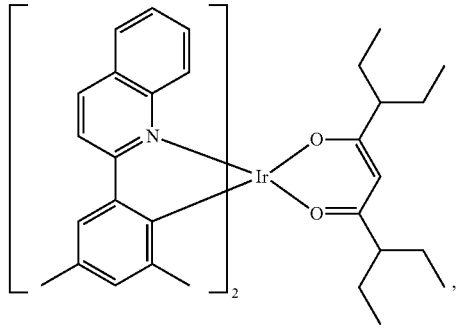

103
-continued
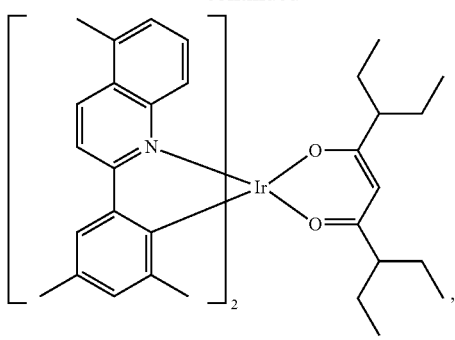
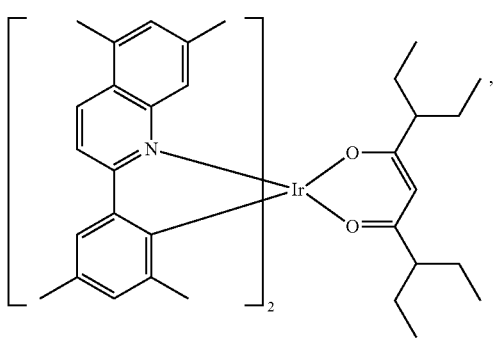
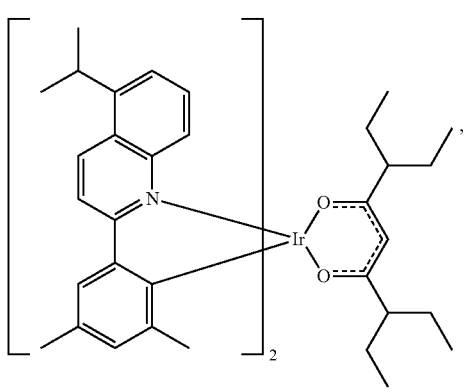
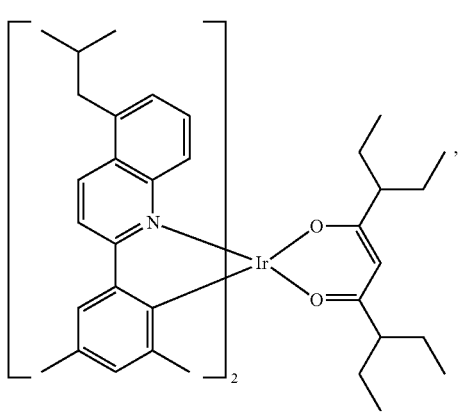
104
-continued
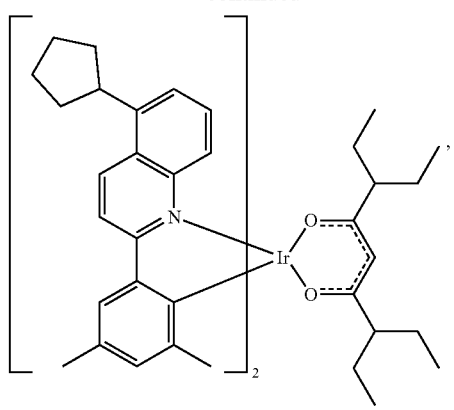
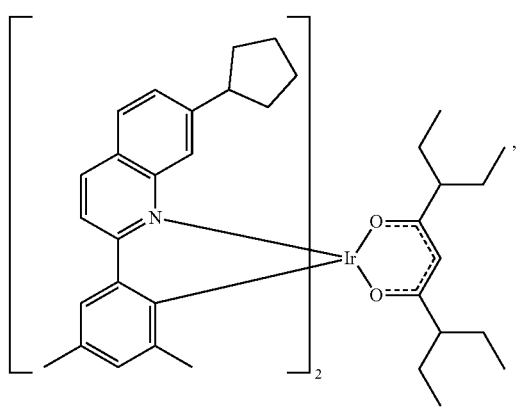
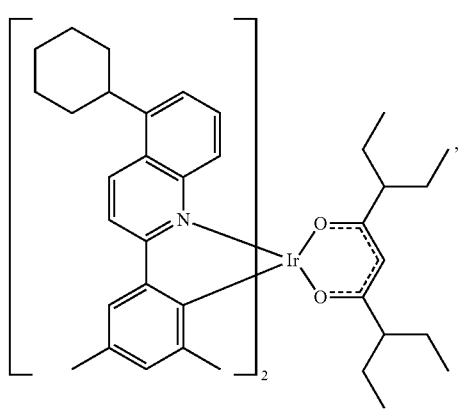
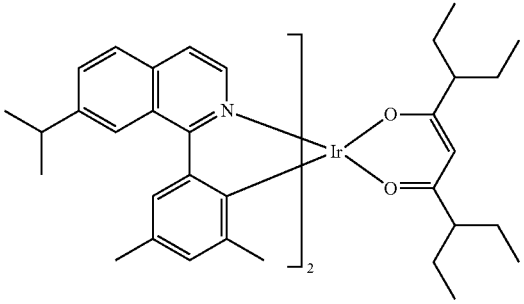

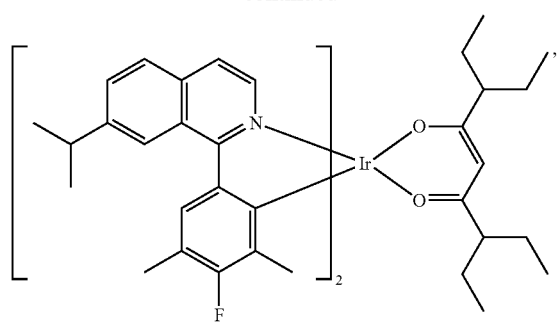
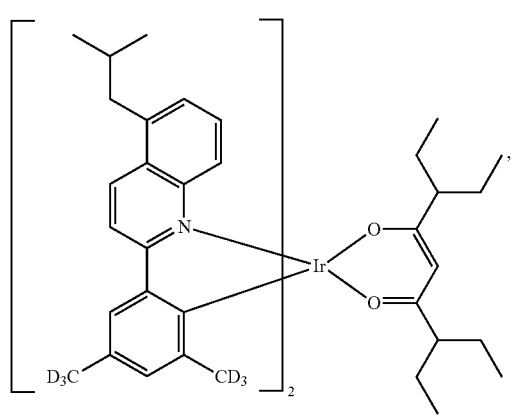
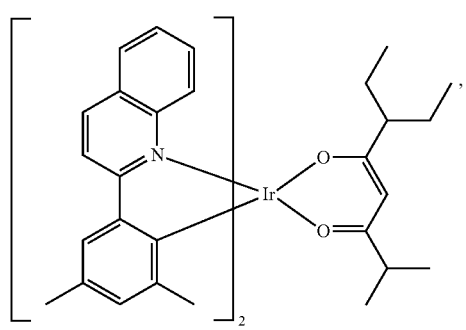
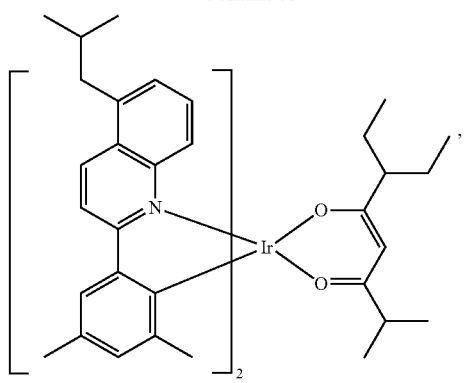
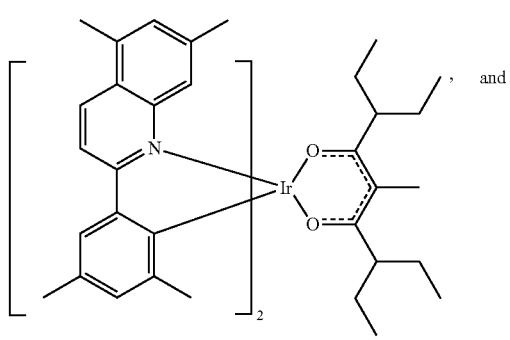
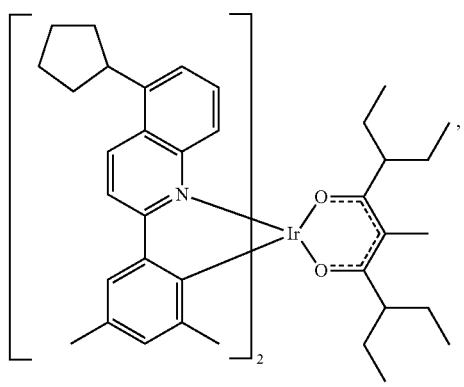
Further suitable red emitters are shown in US 2016/0093808. Preferred red emitters according to this document are the following compounds:
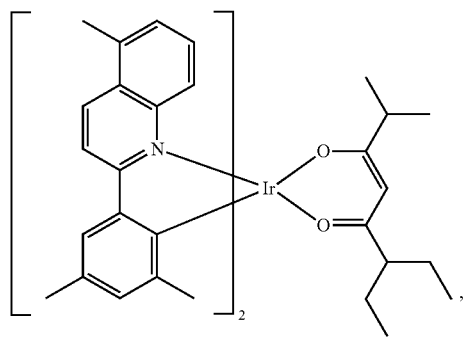
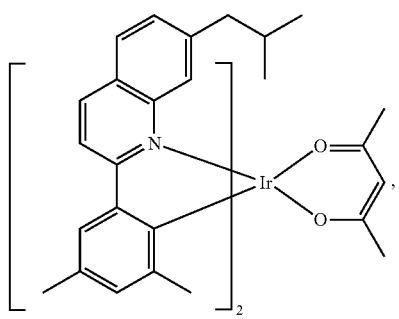

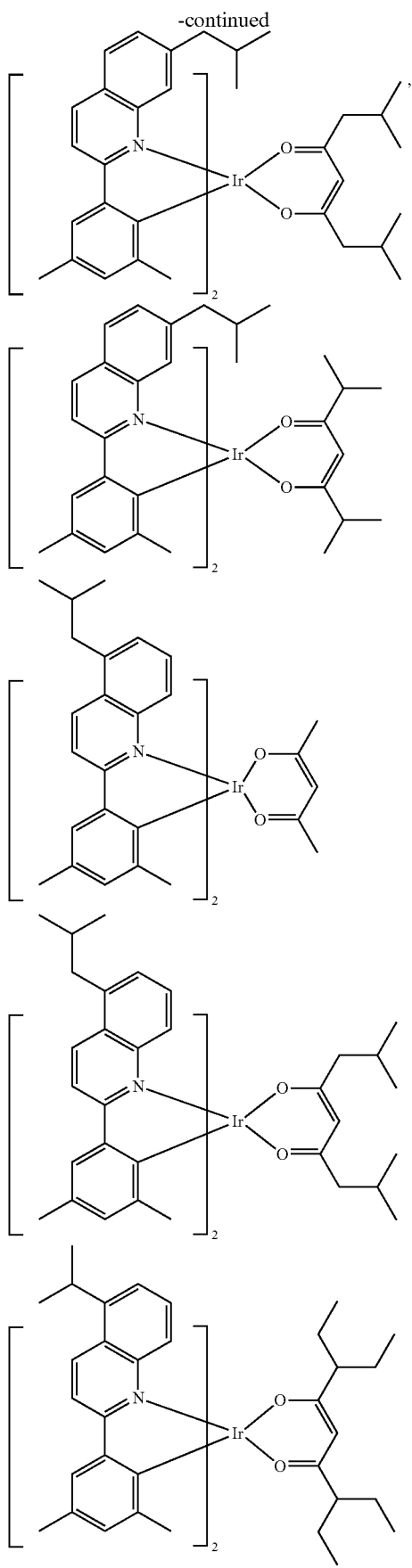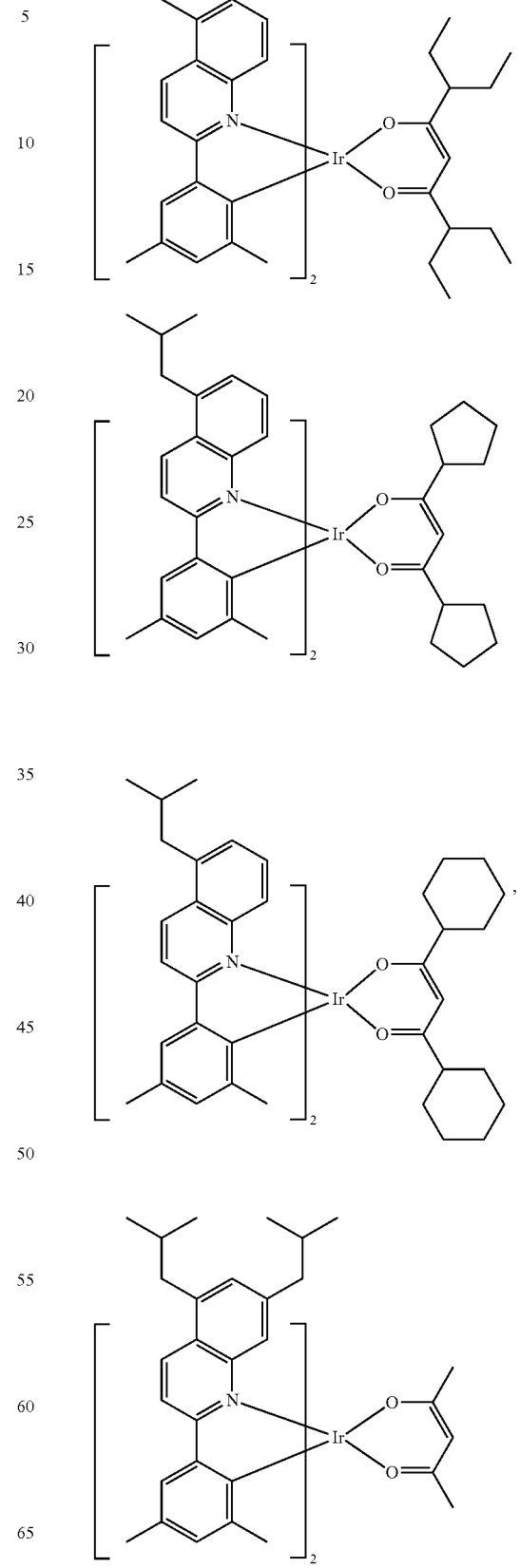

109
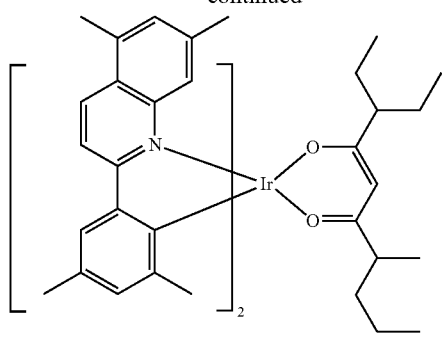
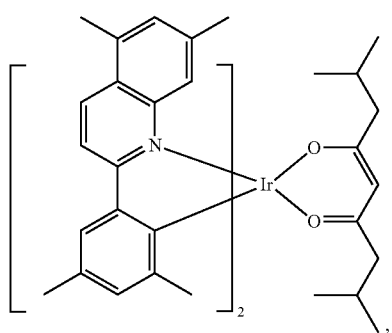
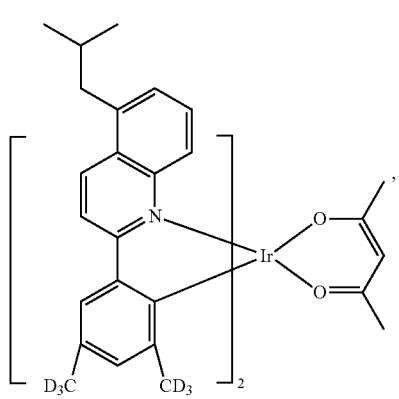
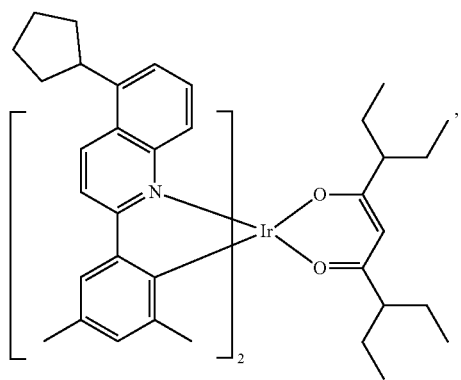
110
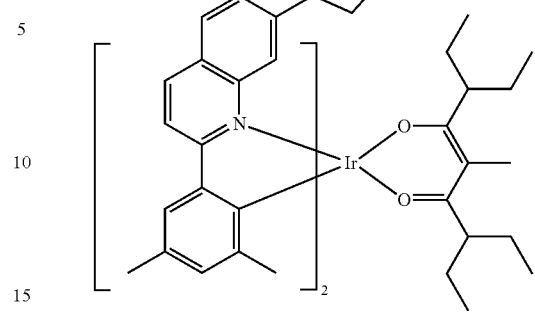
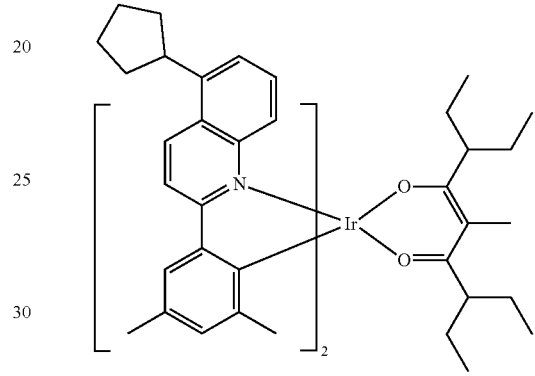
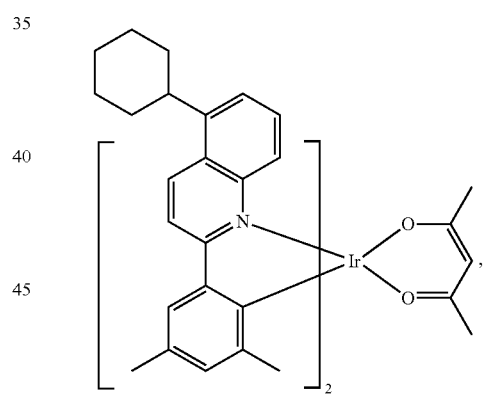
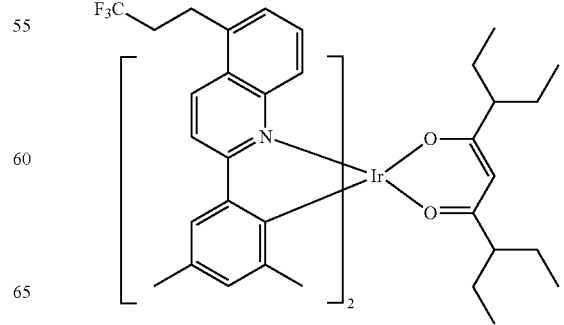

111
-continued
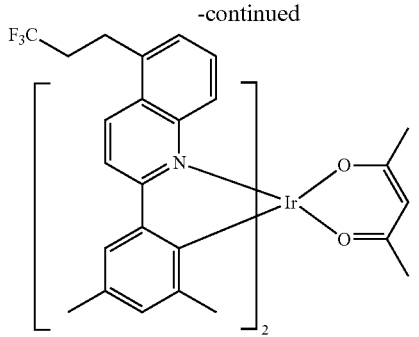
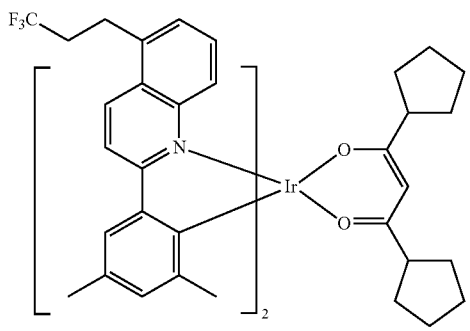
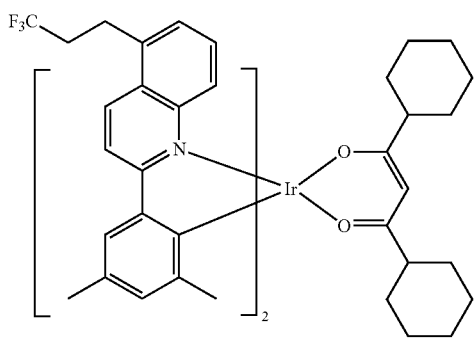
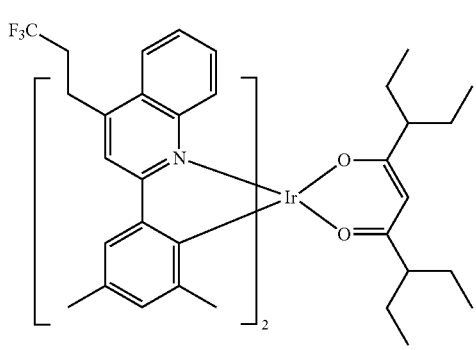
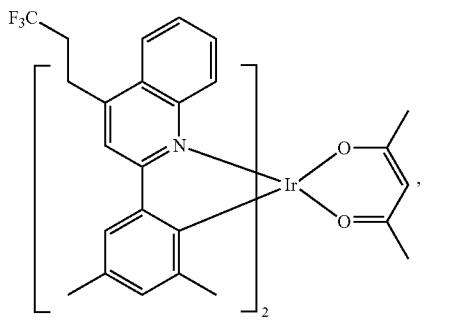
112
-continued
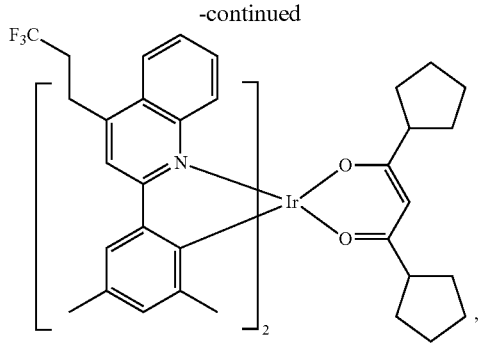
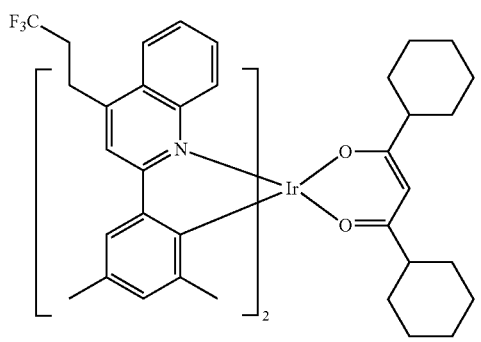
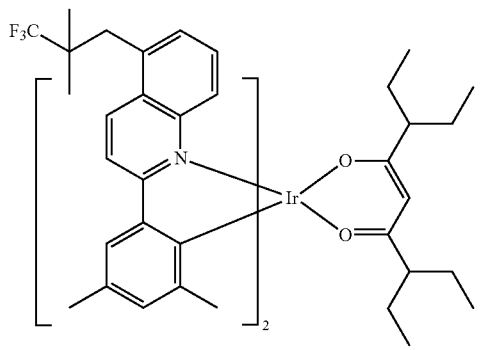
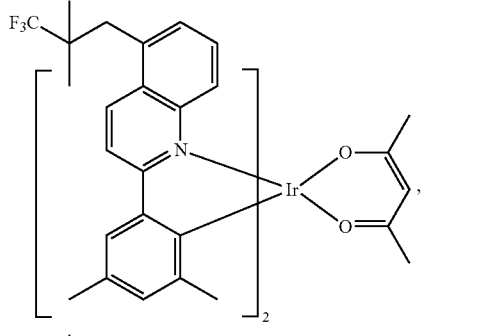
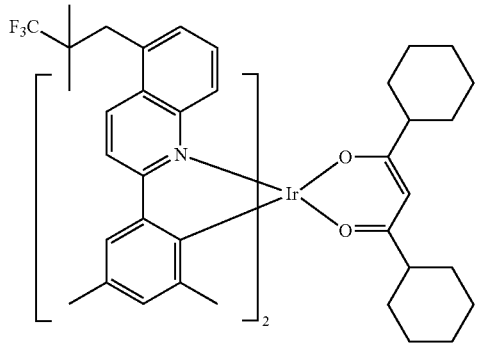

113
-continued
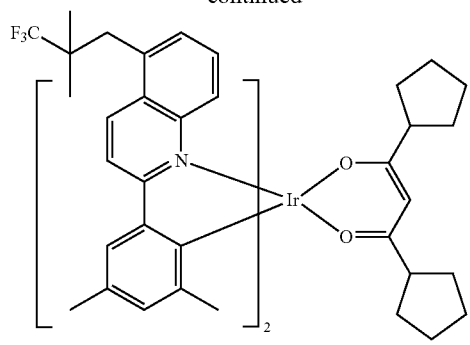
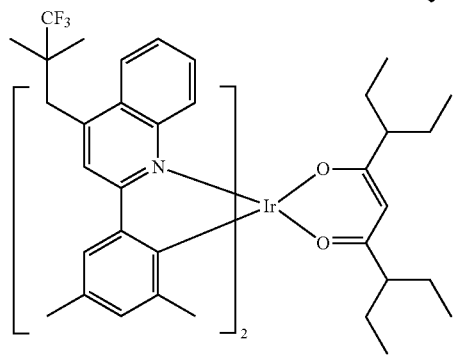
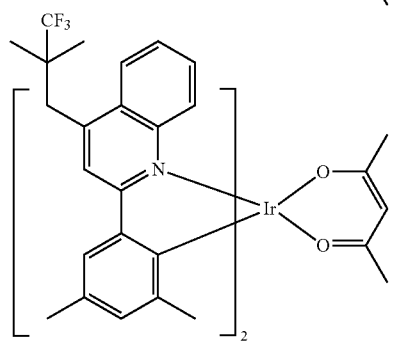
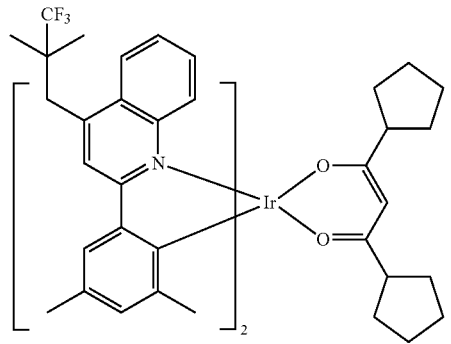
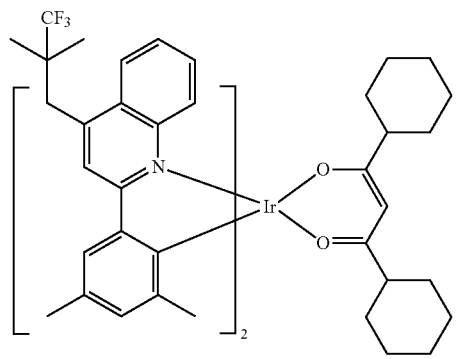
114
-continued
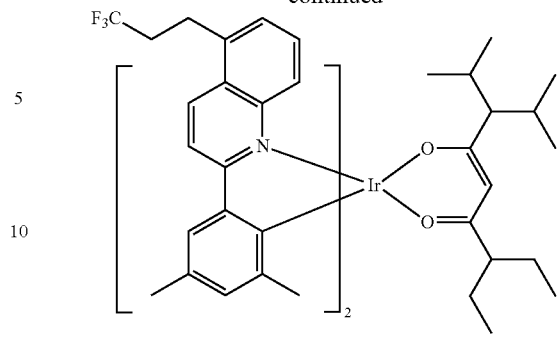
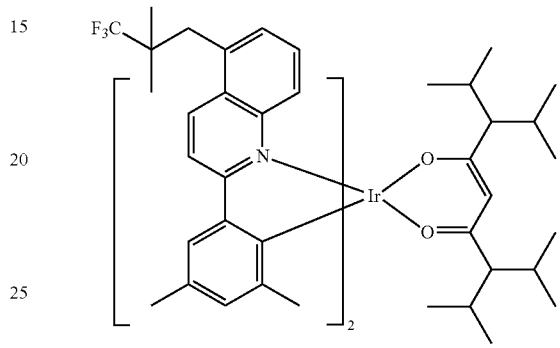
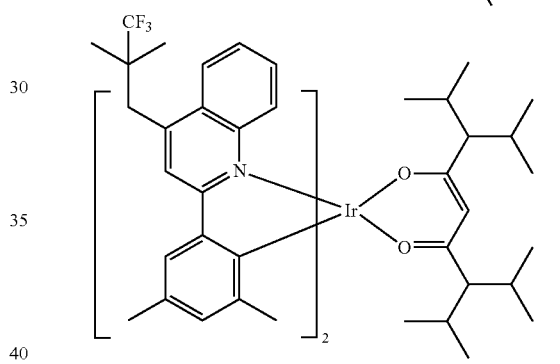
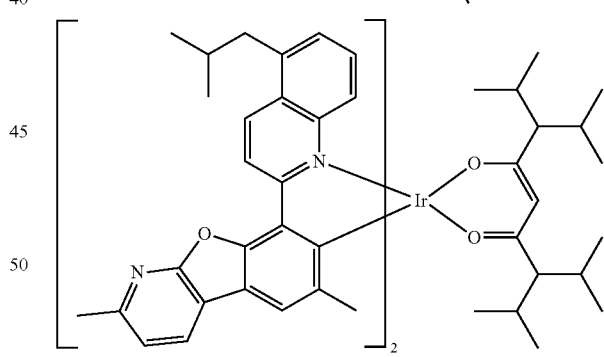
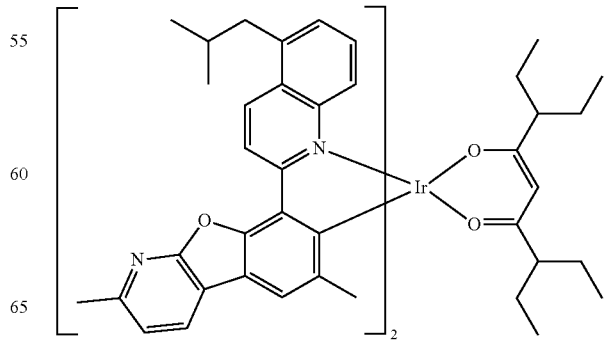

-continued
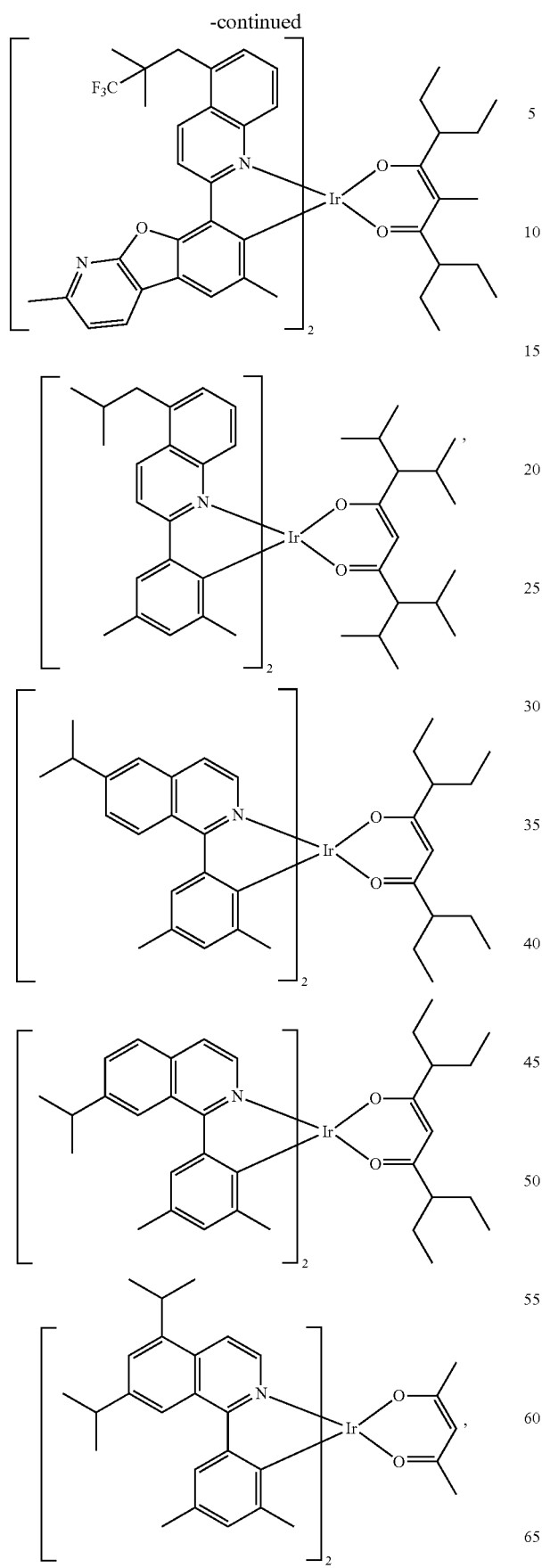
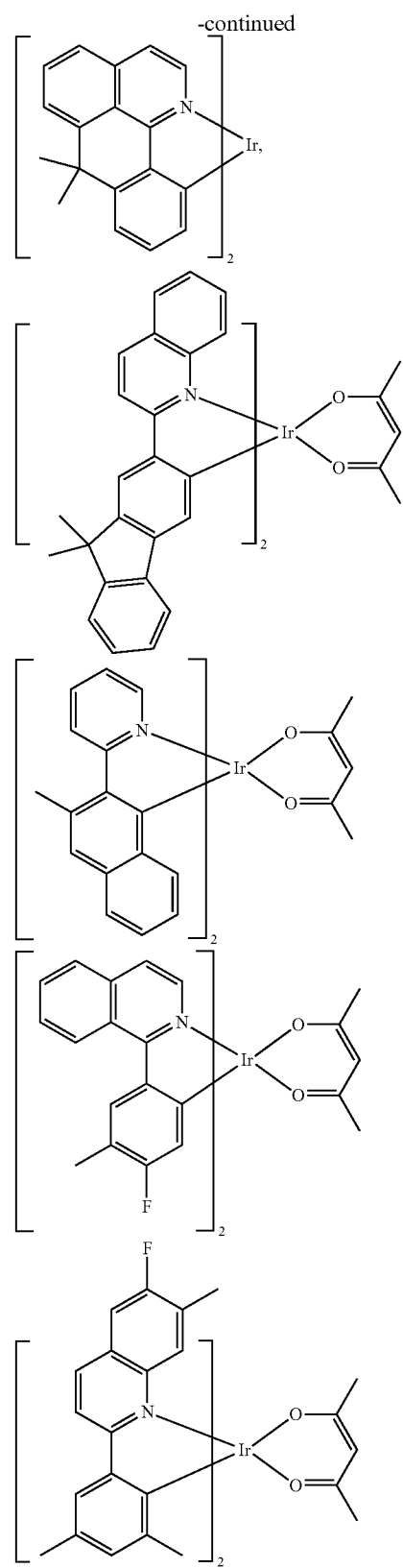
According to a further embodiment of the OLED according to the present invention, the light emitting layer may comprise at least one fluorescent, preferably blue, emitter. Examples of preferred blue dopants that may be present in the light emitting layer of the OLED according to the present invention are polycyclic amine derivatives as mentioned in EP 2924029. Particularly preferred aromatic amine derivatives are selected from compounds according to the following formula (20):

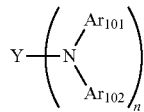
(20)

In the formula (20), Y is a substituted or unsubstituted fused aromatic hydrocarbon group including 10 to 50 ring carbon atoms.

$Ar_{101}$, and $Ar_{02}$ are independently a substituted or unsubstituted aryl group including 6 to 50 ring carbon atoms or a substituted or unsubstituted heterocyclic ring group including 5 to 50 ring atoms.

Specific examples of Y include the above-mentioned fused aryl group. Y is preferably a substituted or unsubstituted anthryl group, a substituted or unsubstituted pyrenyl group or a substituted or unsubstituted chrysenyl group.

n is an integer of 1 to 4. It is preferred that n be an integer of 1 to 2.

The above-mentioned formula (20) is preferably one represented by the following formulas (21) to (24).

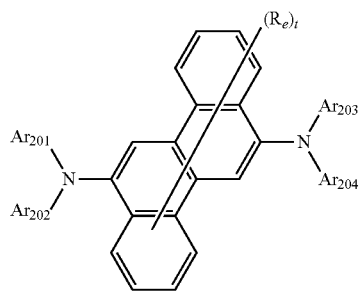
(21)

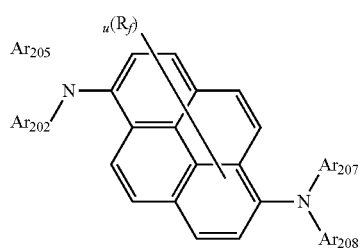
(22)

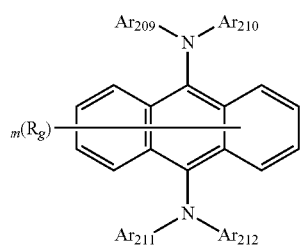
(23)

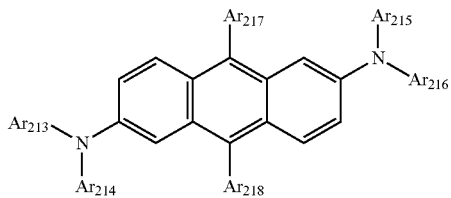
(24)

In the formulae (21) to (24), $R_e$, $R_f$ and $R_g$ are independently a substituted or unsubstituted alkyl group including 1 to 20 carbon atoms, a substituted or unsubstituted alkenyl group including 2 to 50 carbon atoms, a substituted or unsubstituted alkynyl group including 2 to 50 carbon atoms, a substituted or unsubstituted aralykyl group including 1 to 20 carbon atoms, a substituted or unsubstituted cycloalkyl group including 3 to 20 ring carbon atoms, a substituted or unsubstituted alkoxy group including 1 to 20 carbon atoms, a substituted or unsubstituted aryloxy group including 6 to 20 ring carbon atoms, a substituted or unsubstituted aryl group including 6 to 50 ring carbon atoms, a substituted or unsubstituted silyl group, a substituted or unsubstituted alkyl germanium group including 1 to 50 carbon atoms or a substituted or unsubstituted aryl germanium group including 6 to 50 ring carbon atoms. $R_e$, $R_f$ and $R_g$ may independently be bonded to any of the bonding positions of the benzene rings that constitutes the fused polycyclic skeleton.

As preferable examples of $R_e$, $R_f$ and $R_g$, a substituted or unsubstituted aryl group including 6 to 50 ring carbon atoms can be given. More preferably, $R_e$, $R_f$ and $R_g$ are a substituted or unsubstituted phenyl group, a substituted or unsubstituted naphthyl group, or the like.

t is an integer of 0 to 10. u is an integer of 0 to 8. m is an integer of 0 to 10. $Ar_{201}$ to $Ar_{218}$ are independently an aryl group including 6 to 50 ring carbon atoms or a substituted or unsubstituted heterocyclic group including 5 to 50 ring atoms.

Preferred examples of $Ar_{201}$ to $Ar_{218}$ include a substituted or unsubstituted phenyl group, a substituted or unsubstituted dibenzofuranyl group or the like. As preferable examples of the substituent of $Ar_{201}$ to $Ar_{218}$, an alkyl group, a cyano group and a substituted or unsubstituted silyl group can be given.

In the formulae (21) to (24), as examples of the alkyl group, the alkoxy group, the aryl group, the aryloxy group and the heterocyclic group, those exemplified above can be given.

As the alkenyl group including 2 to 50, preferably 2 to 30, more preferably 2 to 20, and particularly preferably 2 to 10, carbon atoms, a vinyl group, an allyl group, a 1-butenyl group, a 2-butenyl group, a 3-butenyl group, a 1,3-butanedienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, a 3-phenyl-1-butenyl group or the like can be given. Preferred are a styryl group, a 2,2-diphenylvinyl group, a 1,2-diphenylvinyl group or the like.

As the alkynyl group including 2 to 50 (preferably 2 to 30, more preferably 2 to 20, particularly preferably 2 to 10) carbon atoms, a propargyl group, a 3-pentynyl group or the like can be given.

As the alkyl germanium group, a methylhydrogermyl group, a trimethylgermyl group, a triethylgermyl group, a tripropylgermyl group, a dimethyl-t-butylgermyl group or the like can be given.

As the aryl germanium group, a phenyldihydrogermyl group, a diphenylhydrogermyl group, a triphenylgermyl group, a tritolylgermyl group, a trinaphthylgermyl group or the like can be given.

As the styrylamine compound and the styryldiamine compound, those represented by the following formulas (17) and (18) are preferable.

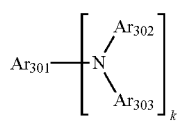

(17)

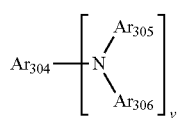

(18)

In the formula (17), $Ar_{301}$ is a k-valent group; a k-valent group corresponding to a phenyl group, a naphthyl group, a biphenyl group, a terphenyl group, a stilbene group, a styrylaryl group and a distyrylaryl group. $Ar_{302}$ and $Ar_{303}$ are independently an aryl group including 6 to 20 ring carbon atoms, and $Ar_{301}$, $Ar_{302}$ and $Ar_{303}$ may be substituted.

k is an integer of 1 to 4, with an integer of 1 and 2 being preferable. Any one of $Ar_{302}$ to $Ar_{303}$ is a group including a styryl group. It is further preferred that at least one of $Ar_{302}$ and $Ar_{303}$ be substituted by a styryl group.

As for the aryl group including 6 to 20 ring carbon atoms, the above-mentioned aryl group can be specifically given. Preferable examples include a phenyl group, a naphthyl group, an anthranyl group, a phenanthryl group, a terphenyl group or the like.

In the formula (18), $Ar_{304}$ to $Ar_{306}$ are a v-valent substituted or unsubstituted aryl group including 6 to 40 ring carbon atoms. v is an integer of 1 to 4, with an integer of 1 and 2 being preferable.

Here, as the aryl group including 6 to 40 ring carbon atoms in the formula (18), the above-mentioned aryl group can be specifically given. A naphthyl group, an anthranyl group, a chrysenyl group, a pyrenyl group or an aryl group represented by the formula (20) is preferable.

As preferable substituents that substitute on the aryl group, an alkyl group including 1 to 6 carbon atoms, an alkoxy group including 1 to 6 carbon atoms, an aryl group including 6 to 40 ring carbon atoms, an amino group substituted by an aryl group including 6 to 40 ring carbon atoms, an ester group including an aryl group that includes 5 to 40 ring carbon atoms, an ester group including an alkyl group that includes 1 to 6 carbon atoms, a cyano group, a nitro group, a halogen atom or the like can be given.

The content of the emitter materials (dopants), preferably the phosphorescent emitter materials, in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided. The further component in the emitting layer is usually one or more host material, which is preferably present in an amount of 30 to 99.9% by mass, more preferably 70 to 99% by mass, wherein the sum of the emitter material(s) and the host material(s) is 100% by mass.

Further possible fluorescent blue emitters that may be present in the emitting layer of the OLED according to the present invention are mentioned in US2012112169.

Host (Matrix) Materials

The compound of formula (Ia) or (Ib) is preferably employed as host material, more preferably as phosphorescent host material.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA.

In the case that one or more phosphorescent emitter materials are used in the light emitting layer, one or more phosphorescent hosts are usually employed as host material. The phosphorescent host is a compound which confines the triplet energy of the phosphorescent dopant efficiently in the light emitting layer to cause the phosphorescent dopant to emit light efficiently.

In a preferred embodiment, the light-emitting layer is formed of at least one emitter material and of at least one of the matrix materials (hosts) mentioned in this application. According to a preferred embodiment, the electronic device according to the present invention, preferably the OLED according to the present invention, comprises at least one compound according to general formula (Ia) or (Ib) as matrix (host) material.

According to one embodiment, the light-emitting layer comprises at least one emitter material and at least two matrix materials (co-host system), wherein one of the matrix materials is a compound according to general formula (Ia) or (Ib) and the other matrix material(s) is/are used as co-host(s). Suitable other host materials than the compounds of general formula (Ia) or (Ib) (co-hosts) are known by a person skilled in the art. "Further host materials" means in the sense of the present application, host materials different from the compounds of general formula (Ia) or (Ib). However, it is also possible to use two or more different compounds of general formula (Ia) and/or (Ib) as host material in the light-emitting layer in an OLED of the present application. This embodiment is preferably realized with emitter materials that emit red light.

According to another embodiment, the light-emitting layer comprises at least one emitter material and a compound according to general formula (Ia) or (Ib) as a single matrix material. Examples of preferred compounds of general formula (Ia) or (Ib) useful as single host material are shown above. This embodiment is preferably realized with emitter materials that emit red light.

In a more preferred embodiment, the light-emitting layer is formed from 0.1 to 70% by weight, preferably 1 to 30% by weight, of at least one of the aforementioned emitter materials and 30 to 99.9% by weight, preferably 70 to 99% by weight, of at least one of the matrix materials mentioned in the specification—in one preferred embodiment at least one compound according to general formula (Ia) or (Ib)—where the sum total of the emitter material and of the matrix material adds up to 100% by weight.

Suitable host materials that may be used in the electronic device according to the present invention as host materials, if the compounds according to the present invention are not used as host material, but for example as charge transporting material, i.e. as electron transporting material or hole transporting material, are also known by a person skilled in the art.

According to the present invention, the compounds according to general formula (Ia) or (Ib) are preferably be used as host material in the light emitting layer of the electronic device, preferably in a OLED, according to the present invention. The compounds according to general formula (Ia) or (Ib) can be used (a) as single host materials or can be used (b) in combination with any compounds suitable as host materials as mentioned above.

Electron Transport Layer (g) and Electron Injecting Layer (h):

The electron-transporting layer is an organic layer that is formed between the emitting layer and the cathode and has a function of transporting electrons from the cathode to the emitting layer. When the electron-transporting layer is formed of plural layers, an organic layer that is nearer to the cathode is often defined as the electron-injecting layer. The electron-injecting layer has a function of injecting electrons from the cathode efficiently to the organic layer unit.

According to one embodiment, it is preferred that ET layer further comprising the other one or more layer(s) than electron injection layer to enhance efficiency and lifetime of the device, preferably between an electron injection layer and an emitting layer as a hole blocking layer, a exciton blocking layer or a triplet blocking layer.

A compound of the formula (1) is also preferable as all the use of the electron transporting layer, such as an electron transporting layer, an electron-injecting layer, a hole blocking layer, a exciton blocking layer or a triplet blocking layer.

According to one embodiment, it is preferred that an electron-donating dopant be contained in the interfacial region between the cathode and the emitting unit. Due to such a configuration, the organic EL device can have an increased luminance or a long life. Here, the electron-donating dopant means one having a metal with a work function of 3.8 eV or less. As specific examples thereof, at least one selected from an alkali metal, an alkali metal complex, an alkali metal compound, an alkaline earth metal, an alkaline earth metal complex, an alkaline earth metal compound, a rare earth metal, a rare earth metal complex and a rare earth metal compound or the like can be mentioned.

As the alkali metal, Na (work function: 2.36 eV), K (work function: 2.28 eV), Rb (work function: 2.16 eV), Cs (work function: 1.95 eV) and the like can be given. One having a work function of 2.9 eV or less is particularly preferable. Among them, K, Rb and Cs are preferable. Rb or Cs is further preferable. Cs is most preferable. As the alkaline earth metal, Ca (work function: 2.9 eV), Sr (work function: 2.0 eV to 2.5 eV), Ba (work function: 2.52 eV) and the like can be given.

One having a work function of 2.9 eV or less is particularly preferable. As the rare-earth metal, Sc, Y, Ce, Tb, Yb and the like can be given. One having a work function of 2.9 eV or less is particularly preferable.

Examples of the alkali metal compound include an alkali oxide such as $Li_2O$, $Cs_2O$ or $K_2O$, and an alkali halide such as LiF, NaF, CsF and KF. Among them, LiF, $Li_2O$ and NaF are preferable.

Examples of the alkaline earth metal compound include BaO, SrO, CaO, and mixtures thereof such as $Ba_xSr_{1-x}O$ ($0<x<1$) and $Ba_xCa_{1-x}O$ ($0<x<1$). Among them, BaO, SrO and CaO are preferable. Examples of the rare earth metal compound include $YbF_3$, $ScF_3$, $ScO_3$, $Y_2O_3$, $Ce_2O_3$, $GdF_3$ and $TbF_3$. Among these, $YbF_3$, $ScF_3$ and $TbF_3$ are preferable.

The alkali metal complexes, the alkaline earth metal complexes and the rare earth metal complexes are not particularly limited as long as they contain, as a metal ion, at least one of alkali metal ions, alkaline earth metal ions, and rare earth metal ions. Meanwhile, preferred examples of the ligand include, but are not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfluborane, bipyridyl, phenanthroline, phthalocyanine, porphyrin, cyclopentadiene, β-diketones, azomethines, and derivatives thereof.

Regarding the addition form of the electron-donating dopant, it is preferred that the electron-donating dopant be formed in a shape of a layer or an island in the interfacial region. A preferred method for the formation is a method in which an organic compound (a light emitting material or an electron-injecting material) for forming the interfacial region is deposited simultaneously with deposition of the electron-donating dopant by a resistant heating deposition method, thereby dispersing the electron-donating dopant in the organic compound. The dispersion concentration of the organic compound: the electron-donating dopant (molar ratio) is 100:1 to 1:100, preferably 5:1 to 1:5.

In a case where the electron-donating dopant is formed into the shape of a layer, the light-emitting material or electron-injecting material which serves as an organic layer in the interface is formed into the shape of a layer. After that, a reductive dopant is solely deposited by the resistant heating deposition method to form a layer preferably having a thickness of from 0.1 nm to 15 nm. In a case where the electron-donating dopant is formed into the shape of an island, the emitting material or the electron-injecting material which serves as an organic layer in the interface is formed into the shape of an island. After that, the electron-donating dopant is solely deposited by the resistant heating deposition method to form an island preferably having a thickness of from 0.05 nm to 1 nm.

The ratio of the main component and the electron-donating dopant in the organic EL device according to the invention is main component: electron-donating dopant=5:1 to 1:5 in terms of molar ratio, more preferably 2:1 to 1:2.

As the electron-transporting material used in the electron-transporting layer other than a compound of the formula (1), an aromatic heterocyclic compound having one or more hetero atoms in the molecule may preferably be used. In particular, a nitrogen containing heterocyclic derivative is preferable.

According to one embodiment, it is preferable that ET layer comprises a nitrogen containing heterocyclics metal chelate, such as 8-hydroxyquinolinolato aluminum, which is generally called as $Alq_3$.

According to the other embodiment, it is preferable that ET layer comprising substituted or unsubstituted nitrogen containing heterocyclic derivative.

Specific examples of the preferable heterocyclic derivative for ET layer are, 6-membered azine derivatives; such as pyridine derivatives, pyrimidine derivatives, triazine derivatives, pyrazine derivatives, preferably pyrimidine derivatives or triazine derivatives; 6-membered fused azine derivatives, such as quinolone derivatives, isoquinoline derivatives, quinoxaline derivatives, quinazoline derivatives, phenanthroline derivatives, benzoquinoline derivatives, benzoisoquinoline derivatives, dibenzoquinoxaline derivatives, preferably quinolone derivatives, isoquinoline derivatives, phenanthroline derivatives; 5-membered heterocyclic derivatives, such as imidazole derivatives, oxazole derivatives, oxadiazole derivatives, triazole derivatives, thiazole derivatives, thiadiazole derivatives; fused imidazole derivatives, such as benzimidazole derivatives, imidazopyridine derivatives, naphthoimidazole derivatives, benzimidazophenanthridine derivatives, benzimidzobenzimidazole derivatives, preferably benzimidazole derivatives, imidazopyridine derivatives or benzimidazophenanthridine derivatives.

According to the other embodiment, it is preferable ET layer comprises phosphine oxide derivative represented as $Ar_{p1}Ar_{p2}Ar_{p3}P=O$.

$Ar_{p1} \sim Ar_{p3}$ are the substituents of phosphor atom and each independently represent substituted or unsubstituted above mentioned aryl group or substituted or unsubstituted above mentioned heterocyclic group.

According to the other embodiment, it is preferable that ET layer comprises aromatic hydrocarbon derivatives.

Specific examples of the preferable aromatic hydrocarbon derivatives for ET layer are, oligo-phenylene derivatives, naphthalene derivatives, fluorene derivatives, fluoranthenyl group, anthracene derivatives, phenanthrene derivatives, pyrene derivatives, triphenylene derivatives, benzanthracene derivatives, chrysene derivatives, benzphenanthrene derivatives, naphthacene derivatives, benzochrysene derivatives, and so on, preferably anthracene derivatives, pyrene derivatives and fluoranthene derivatives.

Cathode (i):

The cathode (i) is an electrode which serves to introduce electrons or negative charge carriers. The cathode may be any metal or nonmetal which has a lower work function than the anode. Suitable materials for the cathode are selected from the group consisting of alkali metals of group 1, for example Li, Cs, alkaline earth metals of group 2, metals of group 12 of the Periodic Table of the Elements, comprising the rare earth metals and the lanthanides and actinides. In addition, metals such as aluminum, indium, calcium, barium, samarium and magnesium, and combinations thereof, may be used.

In general, the different layers, if present, have the following thicknesses:
anode (a): 500 to 5000 Å (Angstrom), preferably 1000 to 2000 Å;
hole injection layer (b): 50 to 1000 Å, preferably 200 to 800 Å,
hole-transport layer (c): 50 to 1000 Å, preferably 100 to 800 Å,
exciton blocking layer (d): 10 to 500 Å, preferably 50 to 100 Å,
light-emitting layer (e): 10 to 1000 Å, preferably 50 to 600 Å,
hole/exciton blocking layer (f): 10 to 500 Å, preferably 50 to 100 Å,
electron-transport layer (g): 50 to 1000 Å, preferably 200 to 800 Å,
electron injection layer (h): 10 to 500 Å, preferably 20 to 100 Å,
cathode (i): 200 to 10 000 Å, preferably 300 to 5000 Å.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive electronic device, preferably OLED, can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

Use of the compounds according to general formula (Ia) or (Ib) in at least one layer of the OLED, preferably in the light-emitting layer, preferably as a host material, a charge transporting material, particularly preferably as a host material and hole or electron transporting material, makes it possible to obtain OLEDs, with high efficiency and with low use and operating voltage. Frequently, the OLEDs obtained by the use of the compounds according to general formula (Ia) or (Ib) additionally have long lifetime. The efficiency of the electronic devices, preferably OLEDs can additionally be improved by optimizing the other layers of the OLEDs. For example, high-efficiency cathodes such as Ca or Ba, if appropriate in combination with an intermediate layer of LiF, can be used. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper. In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Compounds Synthesized
Compound 1
Intermediate 1-1

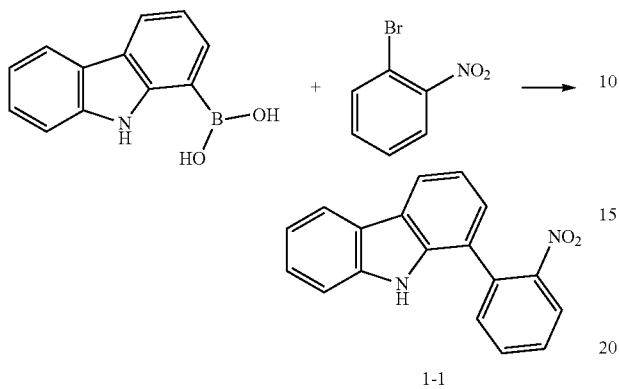

1-1

(9H-Carbazole-1-yl)boronic acid (26.38 g, 90.0 mmol) and 1-bromo-2-nitrobenzene (20.20 g, 100.0 mmol) were dissolved in 700 ml of dimethylacetamide. The reaction mixture was evacuated and purged with Argon gas three times. Then, $PdCl_2(dppf)$-$CH_2Cl_2$ (4.08 g, 5.00 mmol) and potassium acetate (29.44 g, 300.0 mmol) were added to the mixture, and the reaction mixture was stirred at 135° C. for 21 h. The solid was removed by filtration, and the filtrate was concentrated. The solid was washed with toluene, and the toluene solution was concentrated. The crude product was purified by column chromatography on silica gel eluting with a mixed solvent of toluene and heptane to yield 13.61 g (55%) of 1-1 as a brown solid.

Without further purification, it was used for the next reaction.

Intermediate 1-2

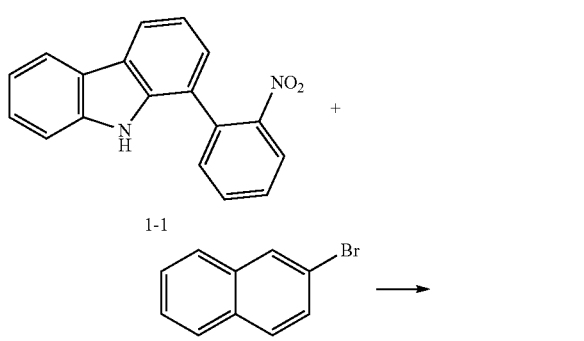

1-1 (2.50 g, 8.67 mmol), 2-bromonaphthalene (2.33 g, 11.27 mmol), and sodium-tert-butoxide (1.17 g, 12.14 mol) were suspended in 58 ml of xylene. The mixture was evacuated and purged with Argon gas three times. Then, $tBu_3P$—$HBF_4$ (0.20 g, 0.695 mmol) and $Pd_2(dba)_3$ (0.159 g, 0.173 mmol) were added there, and the mixture was stirred at 100° C. overnight. The reaction mixture was filtered off, and then washed with toluene, ethanol, and water. After the solid was dried in vacuum oven, 1-2 was obtained as a grey solid in a yield of 70% (2.50 g). Without further purification, it was used for the next reaction.

LC-MS: 414 [M+H]

Intermediate 1-3

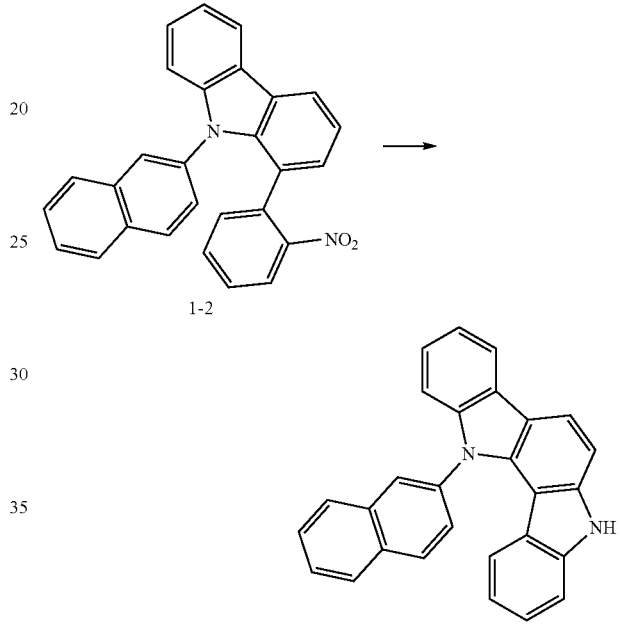

1-2 (1.45 g, 3.50 mmol) and triphenylphosphine (2.75 g, 10.5 mmol) were added in 3 ml of 1,2-dichlorobenzene. The mixture was stirred at 180° C. for 21 h under nitrogen flow. After the solvent was evaporated, the crude product was purified by column chromatography on silica gel eluting with a mixed solvent of heptane and toluene to yield 1.13 g (84%) of 1-3 as a white solid.

LC-MS: 382 [M+H]

Compound 1

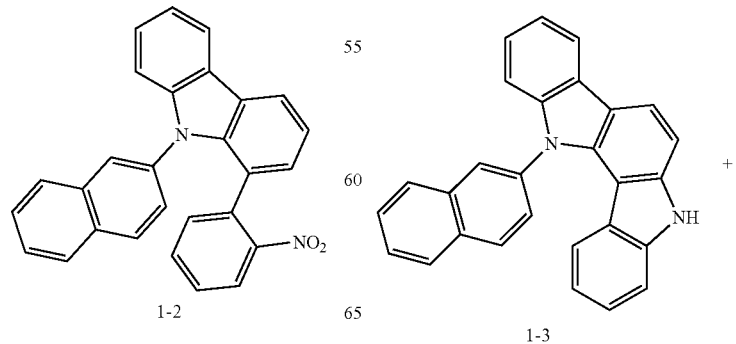

127

-continued

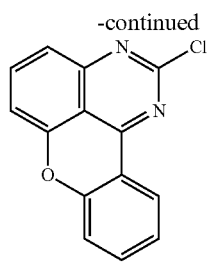

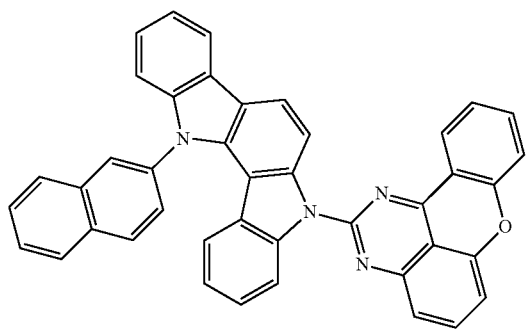

Compound 1

1-3 (1.75 g, 4.58 mmol), 2-chloromeno[4,3,2-de]quinazoline (1.22 g, 4.80 mmol), which was prepared according to the procedure disclosed in WO2017/109727, and potassium carbonate (1.26 g, 9.15 mmol) were added to 30 ml of dimethylacetamide. The reaction mixture was stirred at 120° C. overnight. After the reaction mixture was cooled at room temperature, the solid was collected by filtration, and washed with ethanol and water. The solid was recrystallized with 1,2-dichlorobenzene to yield 2.38 g (87%) of Compound 1 as a yellow solid.

LC-MS: 601 [M+H]

Compound 2

Intermediate 2-1

128

-continued

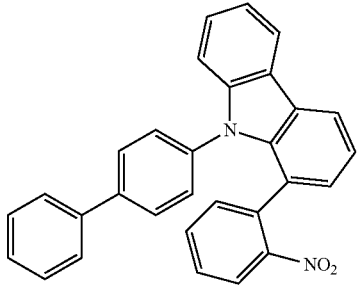

2-1

1-1 (1.70 g, 5.90 mmol), 4-bromo-1,1'-biphenyl (1.44 g, 6.19 mmol), and sodium-tert-butoxide (793 mg, 8.26 mol) were suspended in 30 ml of xylene. The mixture was evacuated and purged with Argon gas three times. Then, $tBu_3P$—$HBF_4$ (137 mg, 0.472 mmol) and $Pd_2(dba)_3$ (108 mg, 0.118 mmol) were added there, and the mixture was stirred at 130° C. for 2 h. The reaction mixture was filtered off, and washed with ethanol, and water. The solid was purified by column chromatography on silica gel eluting with a mixed solvent of heptane and toluene to yield 1.80 g (69%) of 2-1 as a white solid.

LC-MS: 440 [M+H]

Intermediate 2-2

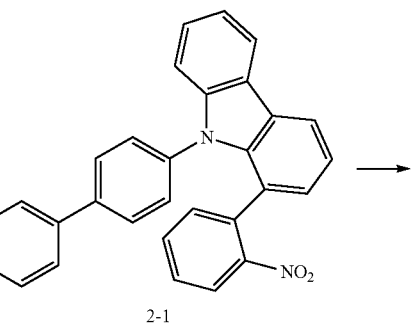

2-1 (1.79 g, 4.06 mmol) and triphenylphosphine (3.41 g, 13.0 mmol) were added in 4 ml of 1,2-dichlorobenzene. The mixture was stirred at 180° C. overnight under nitrogen flow. After the solvent was evaporated, the crude product was purified by column chromatography on silica gel eluting with a mixed solvent of heptane and toluene to yield 1.20 g (72%) of 2-2 as a beige solid.

LC-MS: 408 [M+H]

Compound 2

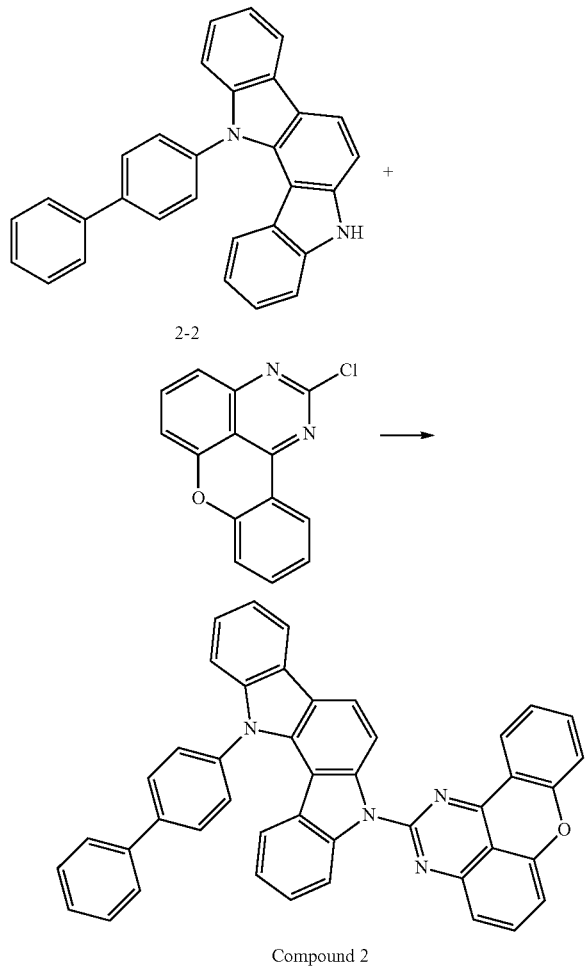

2-2 (1.20 g, 2.94 mmol), 2-chloromeno[4,3,2-de]quinazoline (786 mg, 3.08 mmol), and potassium carbonate (812 mg, 5.88 mmol) were added to 20 ml of dimethylacetamide. The reaction mixture was stirred at 140° C. overnight. After the reaction mixture was cooled at room temperature, the solid was collected by filtration, and washed with ethanol and water. The solid was recrystallized with 1,2-dichlorobenzene to yield 1.35 g (73%) of Compound 2 as a yellow solid.

LC-MS: 627 [M+H]

Compound 3

Intermediate 3-1

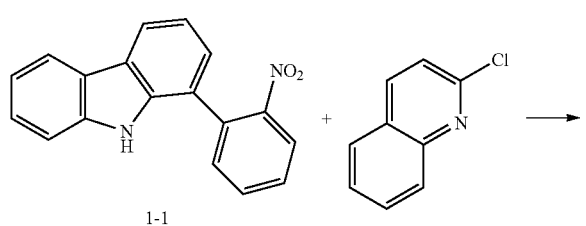

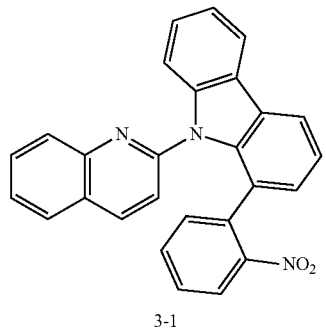

1-1 (1.20 g, 4.16 mmol), 2-chloroquinoline (0.82 g, 4.99 mmol), and sodium-tert-butoxide (560 mg, 5.83 mol) were suspended in 28 ml of xylene. The mixture was evacuated and purged with Argon gas three times. Then, tBu$_3$P—HBF$_4$ (97 mg, 0.33 mmol) and Pd$_2$(dba)$_3$ (76 mg, 0.08 mmol) were added there, and the mixture was stirred at 145° C. overnight. After the reaction mixture was cooled at room temperature, filtered off, and washed with ethanol and water. The solid was dried in vacuum oven. 1.80 g (69%) of 3-1 was obtained as a white solid.

This product was used for the next reaction without further purification.

Intermediate 3-2

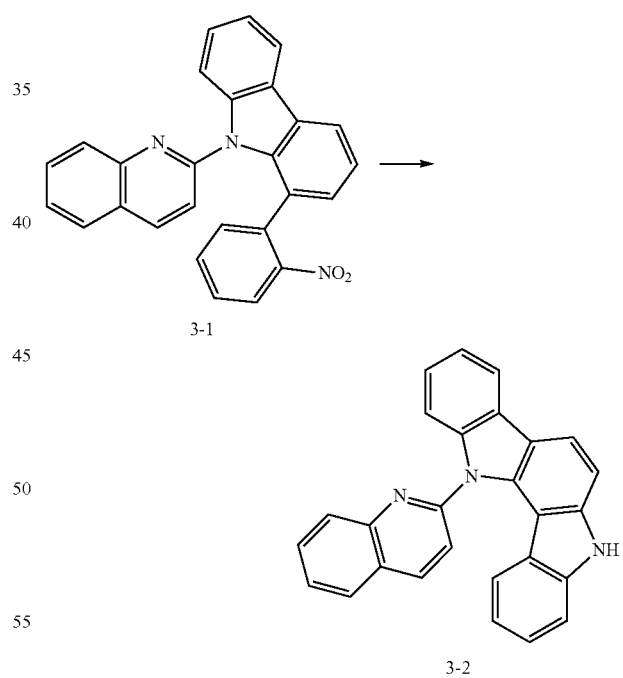

3-1 (1.17 g, 2.82 mmol) and triphenylphosphine (3.69 g, 14.1 mmol) were added in 6 ml of 1,2-dichlorobenzene. The mixture was stirred at 180° C. overnight under nitrogen flow. After the solvent was evaporated, the crude product was purified by column chromatography on silica gel eluting with a mixed solvent of dichloromethane and toluene to yield 0.81 g (75%) of 3-2 as a beige solid. This product was used for the next reaction without further purification.

Compound 3

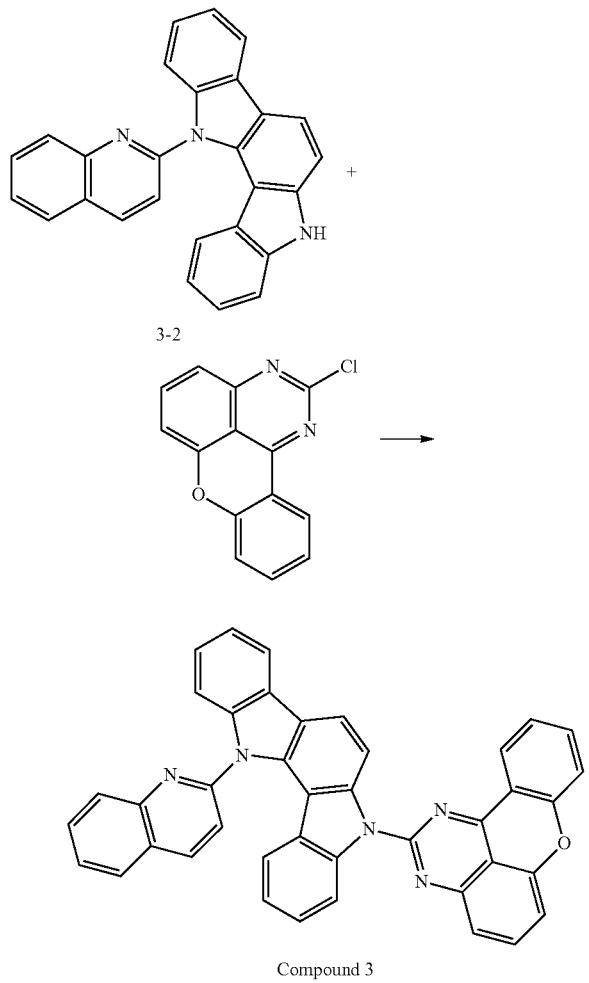

3-2

Compound 3

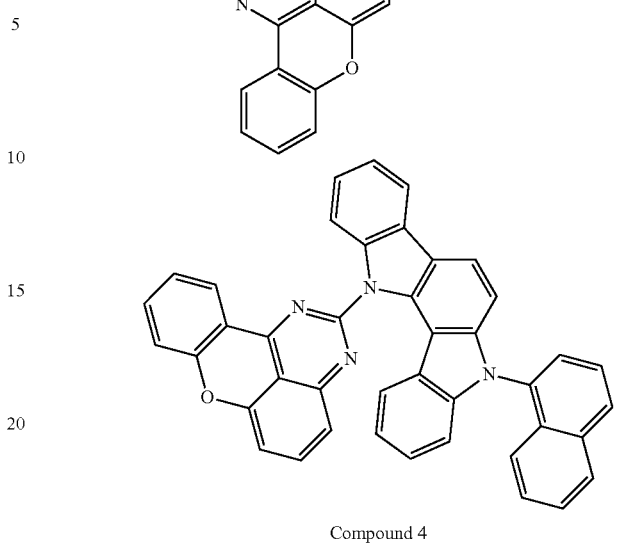

Compound 4

3-2 (1.30 g, 3.39 mmol), 2-chloromeno[4,3,2-de]quinazoline (907 mg, 3.56 mmol), and potassium carbonate (937 mg, 6.78 mmol) were added to 23 ml of dimethylacetamide. The reaction mixture was stirred at 120° C. overnight. After the reaction mixture was cooled at room temperature, the solid was collected by filtration, and washed with ethanol and water. The solid was recrystallized with 1,2-dichlorobenzene to yield 1.85 g (91%) of Compound 3 as a yellow solid.

LC-MS: 602 [M+H]

Compound 4

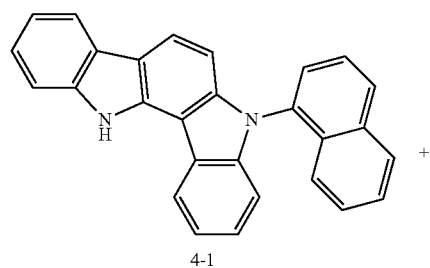

4-1

4-1 (1.14 g, 3.00 mmol), which was prepared according to the procedure disclosed in WO2010113755, 2-chloromeno[4,3,2-de]quinazoline (779 mg, 3.06 mmol), and sodium tert-butoxide (404 mg, 4.20 mmol) were added to 20 ml of toluene. $^t$Bu$_3$P—HBF$_4$ (73 mg, 0.252 mmol) and Pd$_2$(dba)$_3$ (55 mg, 0.06 mmol) were added to the solution, and then the mixture was evacuated and purged with Argon gas three times. The reaction mixture was stirred at 100° C. overnight. After the reaction mixture was cooled at room temperature, water was added there, and the aqueous layer was extracted. The organic layer was dried with MgSO$_4$, filtered and concentrated. The crude product was purified by column chromatography eluting with CHCl$_3$ to yield 1.22 g (68%) of Compound 4 as a yellow solid.

LC-MS: 600 [M+H]

Application Example 1

A glass substrate with 120 nm-thick indium-tin-oxide (ITO) transparent electrode (manufactured by Geomatec Co., Ltd.) used as an anode was first cleaned with isopropanol in an ultrasonic bath for 10 min. To eliminate any possible organic residues, the substrate was exposed to an ultraviolet light and ozone for further 30 min. This treatment also improved the hole injection properties of the ITO. The cleaned substrate was mounted on a substrate holder and loaded into a vacuum chamber. Thereafter, the organic materials specified below were applied by vapor deposition to the ITO substrate at a rate of approx. 0.2-1 Å/sec at about 10$^{-6}$-10$^{-8}$ mbar. As the first layer, 5 nm-thick of electron accepting Compound A was vapor-deposited. Then 210 nm-thick of aromatic amine Compound B was applied as a hole transporting layer and 10 nm-thick of Compound C. Then, a mixture of 2% by weight of an emitter compound (compound D), 98% by weight of a host (Compound 1) was applied to form a 40 nm-thick phosphorescent-emitting layer. On the emitting layer, a mixture of 50% by weight of an electron transporting compound (Compound E), 50% by weight of Liq (8-hydroxyquinolate lithium) was applied to form a 30 nm-thick as an electron transport layer. Finally, 1 nm-thick LiF is deposited as an electron injection layer and 80 nm-thick Al was then deposited as a cathode to complete the device. The device was sealed with a glass lid and a getter in an inert nitrogen atmosphere with less than 1 ppm of water and oxygen.

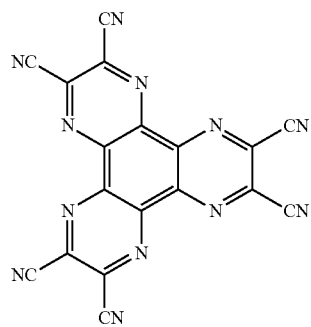
Compound A
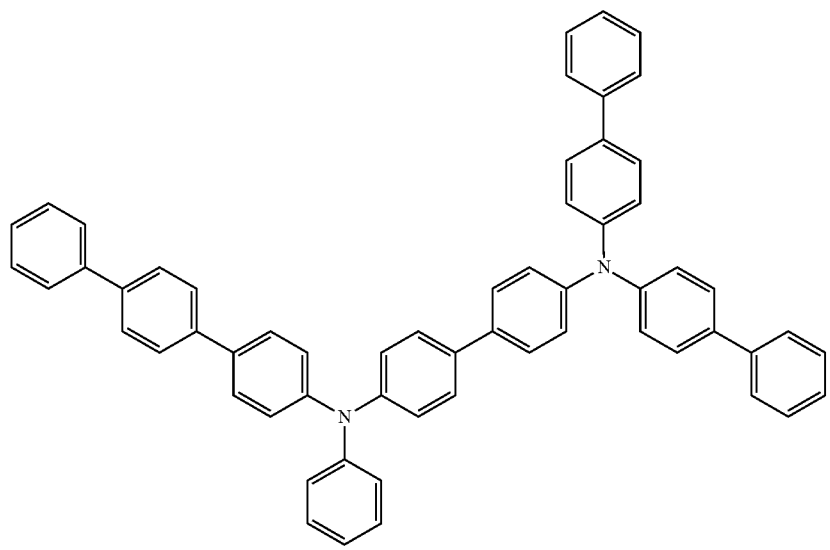
Compound B
Compound C
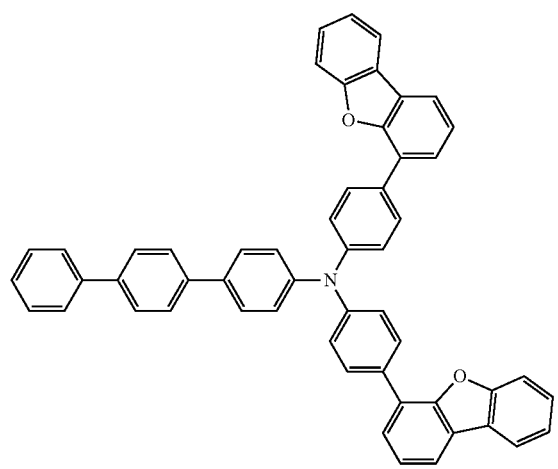
Compound D
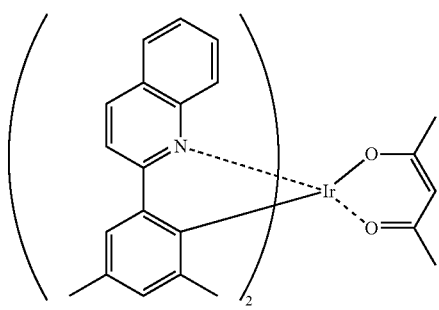

Compound E

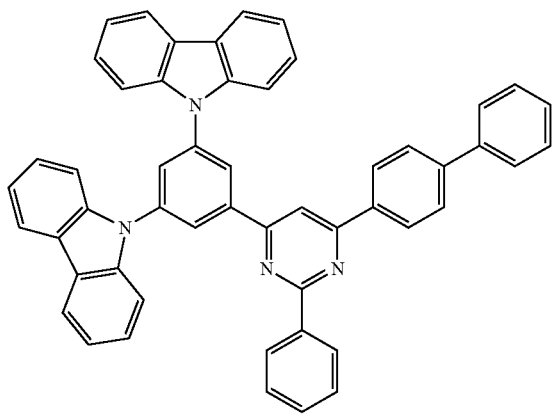

Compound 1

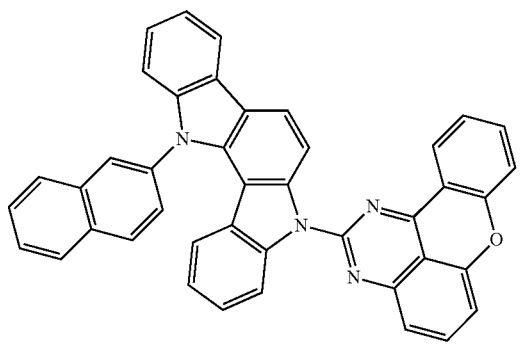

Application Examples 2 and 3

According to the process of Application Example 1, Application Examples 2 and 3 were repeated except that the host (Compound 1) was replaced by Compound 2 and Compound 3. The device results were shown in Table 1.

Comparative Application Examples 1 and 2

According to the process of Application Example 1, Comparative Application Examples 1 and 2 were repeated except that the host (Compound 1) was replaced by comparative compounds (Comparative 1 and 2). The device results were shown at Table 1.

Comparative 1

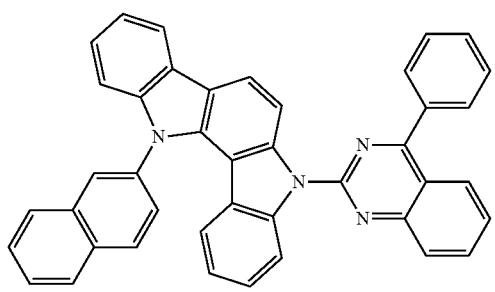

Comparative 2

OLED Characterization

To characterize the OLED, electroluminescence spectra are recorded at various currents and voltages. In addition, the current-voltage characteristic is measured in combination with the luminance to determine luminous efficiency. Driving voltage (Voltage) and Commission Interna-tionale de l'Éclairage (CIE) coordinate are given at 10 mA/cm$^2$ except otherwise stated.

TABLE 1

| Appl. Ex. | Host | Voltage (V) | CIE x, y |
|---|---|---|---|
| Appl. Ex. 1 | Compound 1 | 4.34 | 0.66, 0.34 |
| Appl. Ex. 2 | Compound 2 | 4.62 | 0.66, 0.34 |
| Appl. Ex. 3 | Compound 3 | 4.74 | 0.66, 0.34 |
| Comp. Appl. Ex. 1 | Comparative 1 | 5.21 | 0.66, 0.34 |
| Comp. Appl. Ex. 2 | Comparative 2 | 5.09 | 0.66, 0.34 |

The results are shown in Table 1. The CIE values show that the electroluminescence is origi-nated from the red emitter compound (Compound D). The Compounds 1, 2 and 3 show lower driving voltage than the comparative compounds (Comparative 1 and 2).

The invention claimed is:

1. A compound represented by one of formulae (IV-1), (IV-2), (IV-3), or (IV-4):

(IV-1)

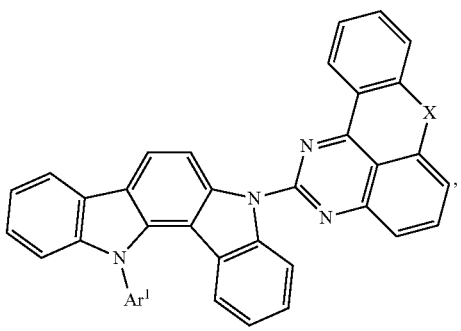

-continued (IV-2)

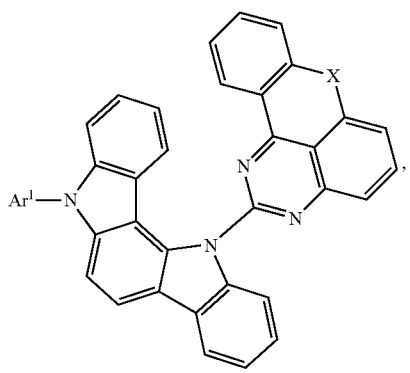

(IV-3)

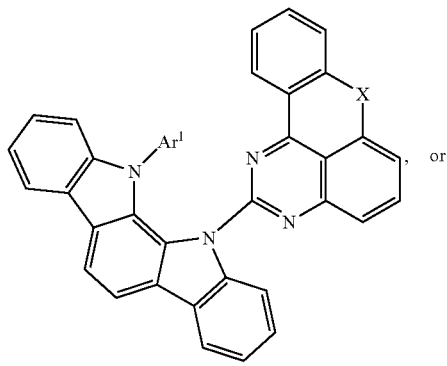
, or (IV-4)

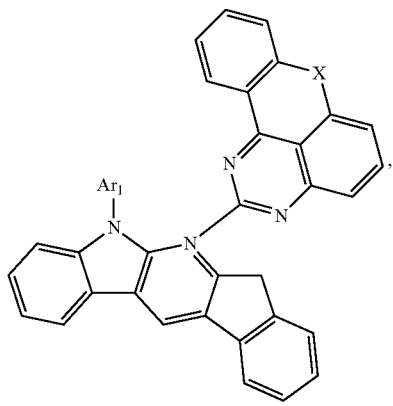

wherein X is O, S, NR$^{10}$ or CR$^{11}$R$^{12}$;

R$^{10}$, R$^{11}$ and R$^{12}$ are independently H, an unsubstituted or substituted C$_6$-C$_{24}$-aryl group, an unsubstituted or substituted C$_1$-C$_{30}$ heteroaryl group, an unsubstituted or substituted C$_1$-C$_{25}$ alkyl group, an unsubstituted or substituted C$_7$-C$_{25}$ aralkyl group, or an unsubstituted or substituted C$_5$-C$_{12}$ cycloalkyl group; and Ar$^1$ is an unsubstituted or substituted group selected from the group consisting of naphthyl, biphenyl, dibenzofuranyl, dibenzothiophenyl, quinazolinyl, and quionolinyl.

2. The compound of claim 1, wherein Ar$^1$ is represented by naphthyl, which is unsubstituted or biphenylyl, which is unsubstituted.

3. A process for preparing the compound of claim 1, the process comprising:

coupling of a compound of formula

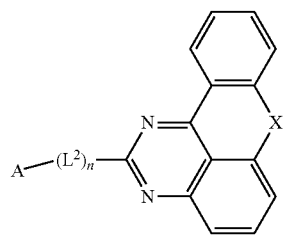

with a compound of formula (a) or (b) below (a)

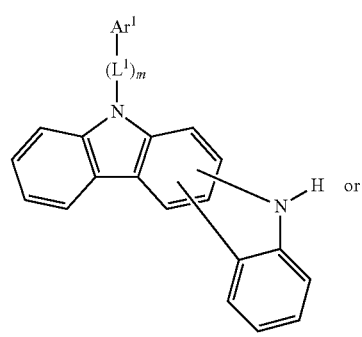

(b)

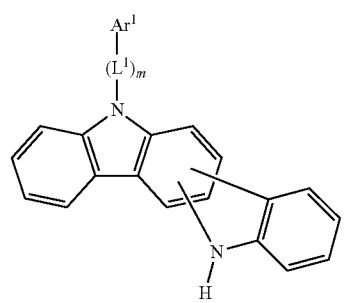

to obtain a compound of formula (Ia) or (Ib)

wherein A is a selected from Cl, Br, I, F, —OSO$_2$CH$_3$, .OSO$_2$CF$_3$, —OSO$_2$C$_6$H$_4$CH$_3$ or —CHO; and X is O, S, NR$^{10}$ or CR$^{11}$R$^{12}$;

a, c, and e independently represent 0;

b is 0;

d is 0;

R$^{10}$, R$^{11}$ and R$^{12}$ are independently of each other H, an unsubstituted or substituted C$_6$-C$_{24}$aryl group, an unsubstituted or substituted C$_1$-C$_{30}$heteroaryl group, an unsubstituted or substituted C$_1$-C$_{25}$alkyl group, an unsubstituted or substituted C$_7$-C$_{25}$aralkyl group or an unsubstituted or substituted C$_5$-C$_{12}$cycloalkyl group;

m and n represent 1;

L$^1$ and L$^2$ a direct bond:

Ar$^1$ is unsubstituted or substituted group selected from the group consisting of naphthyl, biphenyl, dibenzofuranyl, dibenzothiophenyl, quinazolinyl, and quionolinyl.

4. An electronic device comprising the compound of claim 1.

5. The electronic device of claim 4, comprising:
a cathode,
an anode, and
a plurality of organic thin film layers provided between the cathode and the anode,
wherein the organic thin film layers comprises an emitting layer comprising the compound of formula (IV-1) to (IV-4).

6. The electronic device of claim 4, wherein the emitting layer comprises a phosphorescent material, which is an ortho-metallated complex comprising a metal atom selected from the group consisting of iridium, osmium and platinum.

7. An electronic equipment comprising the organic claim 4.

8. An emitting layer comprising the compound of claim 1.

9. A host material, a charge transporting material, charge and/or exciton blocking material in an electronic device comprising the compound of claim 1.

10. A material for an organic electroluminescence device comprising the compound of claim 1.

11. The compound of claim 1, which is represented by formula (IV-1).

12. The compound of claim 1, which is represented by formula (IV-2).

13. The compound of claim 1, which is represented by formula (IV-3).

14. The compound of claim 1, which is represented by formula (IV-4).

\* \* \* \* \*